(12) United States Patent
Kularatne et al.

(10) Patent No.: US 10,308,606 B2
(45) Date of Patent: Jun. 4, 2019

(54) PSMA-TARGETED NIR DYES AND THEIR USES

(71) Applicant: On Target Laboratories, LLC, West Lafayette, IN (US)

(72) Inventors: Sumith A. Kularatne, West Lafayette, IN (US); Pravin Gagare, West Lafayette, IN (US)

(73) Assignee: On Target Laboratories, LLC, West Lafayette, IN (US)

( * ) Notice: Subject to any disclaimer, the term of this patent is extended or adjusted under 35 U.S.C. 154(b) by 0 days.

(21) Appl. No.: 15/699,124

(22) Filed: Sep. 8, 2017

(65) Prior Publication Data

US 2018/0099934 A1   Apr. 12, 2018

Related U.S. Application Data

(60) Provisional application No. 62/385,528, filed on Sep. 9, 2016.

(51) Int. Cl.

| | |
|---|---|
| *C07D 209/24* | (2006.01) |
| *C07D 209/20* | (2006.01) |
| *A61K 49/00* | (2006.01) |
| *G01N 21/64* | (2006.01) |
| *G01N 33/574* | (2006.01) |

(52) U.S. Cl.
CPC ............ *C07D 209/20* (2013.01); *A61K 49/00* (2013.01); *A61K 49/0032* (2013.01); *A61K 49/0052* (2013.01); *A61K 49/0054* (2013.01); *A61K 49/0056* (2013.01); *G01N 21/6428* (2013.01); *G01N 33/57434* (2013.01); *G01N 33/57492* (2013.01); *C07D 209/24* (2013.01); *G01N 2021/6439* (2013.01)

(58) Field of Classification Search
CPC ............................ C07D 209/24; C07D 209/20

USPC ......................................................... 548/491
See application file for complete search history.

(56) References Cited

U.S. PATENT DOCUMENTS

| | | |
|---|---|---|
| 9,254,341 B2 | 2/2016 | Kularatne et al. |
| 2010/0324008 A1 | 12/2010 | Low et al. |
| 2011/0064657 A1 | 3/2011 | Pomper et al. |
| 2014/0271482 A1 | 9/2014 | Low et al. |
| 2015/0366968 A1 | 12/2015 | Basilion |

OTHER PUBLICATIONS

PCT, International Search Report and Written Opinion Application No. PCT/US2017/050641, dated Nov. 8, 2017.
Chen, Ying, et al., NIH Public Access, Synthesis and Biological Evaulation of Low Molecular Weight Fluorescent Imaging Agents for the Prostate-Specific Membrane Antigen, 20 pages, Dec. 19, 2012.

*Primary Examiner* — Matthew P Coughlin
*Assistant Examiner* — Sagar Patel
(74) *Attorney, Agent, or Firm* — McAndrews, Held & Malloy, Ltd.

(57) ABSTRACT

The present disclosure relates to prostate specific membrane antigen (PSMA) targeted compounds conjugated to near-infra red (NIR) dyes and methods for a method for synthesizing a compound of the formula:

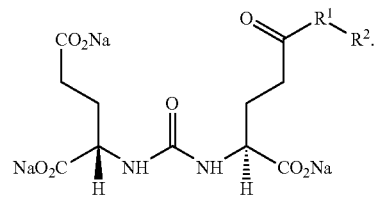

4 Claims, 80 Drawing Sheets

PSMA-TARGETED NIR DYES AND THEIR USES

RELATED APPLICATIONS

The present patent application claims the priority benefit of U.S. Provisional Patent Application No. 62/385,528 filed Sep. 9, 2016. The content of the aforementioned application is hereby incorporated by reference in its entirety into this disclosure.

FIELD OF THE INVENTION

The present disclosure is in the area of diagnostics. This disclosure provides methods of synthesizing and utilizing polyethylene glycol linking groups that are conjugated to a compound used for the targeted imaging of tumors including prostate specific membrane antigen (PSMA) such as prostate cancer and related diseases. Conjugation of amino acid groups to the fluorescent dyes increase specificity and detection of the compound. Methods of manufacture and synthesis of the compounds for use thereof in diagnostic imaging are contemplated.

BACKGROUND OF THE INVENTION

The prostate is one of the male reproductive organs found in the pelvis below the urinary bladder. It functions to produce and store seminal fluid which provides nutrients and fluids that are vital for the survival of sperm introduced into the vagina during reproduction. Like many other tissues, the prostate glands are also prone to develop either malignant (cancerous) or benign (non-cancerous) tumors. The American Cancer Society predicted that over 230,000 men would be diagnosed with prostate cancer and over 30,000 men would die from the disease in year 2005. In fact, prostate cancer is one of the most common male cancers in western societies, and is the second leading form of malignancy among American men. Current treatment methods for prostate cancer include hormonal therapy, radiation therapy, surgery, chemotherapy, photodynamic therapy, and combination therapy. The selection of a treatment generally varies depending on the stage of the cancer. However, many of these treatments affect the quality of life of the patient, especially those men who are diagnosed with prostate cancer over age 50. For example, the use of hormonal drugs is often accompanied by side effects such as osteoporosis and liver damage. Such side effects might be mitigated by the use of treatments that are more selective or specific to the tissue being responsible for the disease state, and avoid non-target tissues like the bones or the liver. As described herein, prostate specific membrane antigen (PSMA) represents a target for such selective or specific treatments.

Surgical removal of malignant disease constitutes one of the most common and effective therapeutic for primary treatment for cancer. Resection of all detectable malignant lesions results in no detectable return of the disease in approximately 50% of all cancer patients' and may extend life expectancy or reduce morbidity for patients in whom recurrence of the cancer is seen. Not surprisingly, surgical methods for achieving more quantitative cytoreduction are now receiving greater scrutiny.

Resection of all detectable malignant lesions results in no detectable return of the disease in approximately 50% of all cancer patients and may extend life expectancy or reduce morbidity for patients in whom recurrence of the cancer is seen. Given the importance of total resection of the malignant lesions, it is beneficial to ensure that the malignant lesions are accurately and completely identified. Identification of malignant tissue during surgery is currently accomplished by three methods. First, many tumor masses and nodules can be visually detected based on abnormal color, texture, and/or morphology. Thus, a tumor mass may exhibit variegated color, appear asymmetric with an irregular border, or protrude from the contours of the healthy organ. A malignant mass may also be recognized tactilely due to differences in plasticity, elasticity or solidity from adjacent healthy tissues. Finally, a few cancer foci can be located intraoperatively using fluorescent dyes that flow passively from the primary tumor into draining lymph nodes. In this latter methodology, fluorescent (sentinel) lymph nodes can be visually identified, resected and examined to determine whether cancer cells have metastasized to these lymph nodes.

PSMA is named largely due to its higher level of expression on prostate cancer cells; however, its particular function on prostate cancer cells remains unresolved. PSMA is overexpressed in the malignant prostate tissues when compared to other organs in the human body such as kidney, proximal small intestine, and salivary glands. PSMA also express in the neo-vasculature of most of the solid tumors. Though PSMA is expressed in brain, that expression is minimal, and most ligands of PSMA are polar and are not capable of penetrating the blood brain barrier. PSMA is a type II cell surface membrane-bound glycoprotein with −110 kD molecular weight, including an intracellular segment (amino acids 1-18), a transmembrane domain (amino acids 19-43), and an extensive extracellular domain (amino acids 44-750). While the functions of the intracellular segment and the transmembrane domains are currently believed to be insignificant, the extracellular domain is involved in several distinct activities. PSMA plays a role in central nervous system, where it metabolizes N-acetyl-aspartyl glutamate (NAAG) into glutamic and N-acetyl aspartic acid. Accordingly, it is also sometimes referred to as an N-acetyl alpha linked acidic dipeptidase (NAALADase). PSMA is also sometimes referred to as a folate hydrolase I (FOLH I) or glutamate carboxypeptidase (GCP II) due to its role in the proximal small intestine where it removes γ-linked glutamate from poly-γ-glutamated folate and a-linked glutamate from peptides and small molecules.

PSMA also shares similarities with human transferrin receptor (TfR), because both PSMA and TfR are type II glycoproteins. More specifically, PSMA shows 54% and 60% homology to TfRI and TfR2, respectively. However, though TfR exists only in dimeric form due to the formation of inter-strand sulfhydryl linkages, PSMA can exist in either dimeric or monomeric form.

Unlike many other membrane-bound proteins, PSMA undergoes rapid internalization into the cell in a similar fashion to cell surface bound receptors like vitamin receptors. PSMA is internalized through clathrin-coated pits and subsequently can either recycle to the cell surface or go to lysosomes. It has been suggested that the dimer and monomer form of PSMA are inter-convertible, though direct evidence of the interconversion is being debated. Even so, only the dimer of PSMA possesses enzymatic activity, and the monomer does not.

Though the role of the PSMA on the cell surface of the prostate cancer cells remains unknown, it has been recognized that PSMA represents a viable target for the selective and/or specific delivery of biologically active agents, including diagnostic agents, imaging agents, and therapeutic agents to such prostate cancer cells.

The radio-immunoconjugate of the anti-PSMA monoclonal antibody (mAb) 7E11, known as the PROSTASCINT® scan, is currently being used to diagnose prostate cancer metastasis and recurrence. However, this agent tends to produce images that are challenging to interpret (Lange, P. H. PROSTASCINT scan for staging prostate cancer. Urology 2001, 57, 402-406; Haseman, M. K.; et al. Cancer Biother Radiopharm 2000, 15, 131-140; Rosenthal, S. A.; et al. Tech Urol 2001, 7, 27-37). It binds to an intracellular epitope of PSMA in necrotic prostate cancer cells. More recently, monoclonal antibodies have been developed that bind to the extracellular domain of PSMA and have been radiolabeled and shown to accumulate in PSMA-positive prostate tumor models in animals. However, diagnosis and tumor detection using monoclonal antibodies has been limited by the low permeability due to their large size [Molecular Weight (MW)~150, 000 Da] and slow clearance from non-targeted tissue. Moreover, the selective targeting of radio- or optical imaging agents either for imaging or therapeutic purposes is challenging due to their long half-life (~30 days). Especially, patients have to be stay in the hospital for longer days and spend more money on medical bills.

Two promising approaches to fluorescence-guided surgery are currently under intense investigation for use in the clinic. In one method, an activatable NIR fluorescent probe, which is minimally fluorescent in the steady state due to its proximity to an attached quencher, becomes highly fluorescent upon release of the quencher in malignant tissue. One of the most commonly used release mechanisms involves incorporation of a peptide sequence between the dye and the quencher that can be specifically cleaved by a tumor-enriched protease (i.e. cathepsins, caspases and matrix metalloproteinases). A major advantage of this strategy lies in the absence of fluorescence in tissues that lack the activating enzyme, allowing tissues along the excretion pathway (e.g. kidneys, bladder, liver) to remain nonfluorescent unless they fortuitously express the cleaving enzyme. Such tumor-activated NIR dyes can also generate substantial fluorescence in the tumor mass as long as the malignant lesion is enriched in the cleaving protease and the released dye is retained in the tumor. The major disadvantage of this methodology arises from the poor tumor specificities of many of the relevant hydrolases (most of which are also expressed in healthy tissues undergoing natural remodeling or experiencing inflammation). Moreover, the abundance of the desired proteases may vary among tumor masses, leading to slow or no activation of fluorescence in some malignant lesions and rapid development of fluorescence in others. Most of the time, these activatable peptides contain over 20 amino acids linked via peptide bonds that could lead to higher molecular weights, longer lead time (24 h), cleavage of peptide bonds by peptidase in the circulation, high false positive results and very high manufacturing costs.

Other release mechanisms that activatable dyes use are pH difference between circulation and within the tumor or change in redox potential.

In the second, a fluorescent dye is conjugated to a tumor-specific targeting ligand that causes the attached dye to accumulate in cancers that over-express the ligand's receptor. While PSMA-targeted antibody-NIR dye conjugates have not yet been entered to clinical trials for fluorescence-guided surgery of cancer, several types of NIR dyes have been conjugated to monoclonal antibodies such as Her-2 with the intent of clinical development. Unfortunately, most of these dyes are tethered to antibodies non-specifically via amide, disulfide, or maleimide chemistry using either lysine or cysteine residues in the protein leading to heterogeneous chemical entities which result in variable affinities, efficacies, PK and safety profiles. Moreover, maleimide and disulfide bonds are known to be unstable in the circulation (half-life-≤2 h). On the other hand, lack of precise structural definition may limit progression of these conjugates into the clinical use due to challenges associated with the production process and safety. Moreover, production of these antibodies (MW ~150, 000 Da) is highly expensive when compared to small molecular ligands. In contrast, small molecule ligand (MW>0.5 Da), can penetrate solid tumors rapidly, and clears from PSMA-negative tissues in <2 h, shows high tumor-to-background ratios, easy of synthesis, and stable during the synthesis and storage.

Despite all the advantages those small molecular ligands have, development of NIR dye that maintains or enhances the properties of the small molecule is challenging. Recently, a variety of low molecular weight inhibitors of PSMA have been conjugated to visible light wave length dyes (400-600 nm) such as fluorescein and rhodamine and tested in in animal models [Kularatne S A, Wang K, Santhapuram H K, Low P S. Mol Pharm. 2009 May-June; 6(3):780-9] or in cells in culture [ Liu T, Nedrow-Byers J R, Hopkins M R, Berkman C E. Bioorg Med Chem Lett. 2011 Dec. 1; 21(23)] or in human blood samples (He W, Kularatne S A, Kalli K R, Prendergast F G, Amato R J, Klee G G, Hartmann L C, Low P S. Int J Cancer. 2008 Oct. 15; 123(8):1968-73).

The visible light wave length dyes are not optimal for intra-operative image-guided surgery as these dyes are associated with a relatively high level of nonspecific background light due to the presence of collagen in the tissues. Hence the signal to noise ratio from these conventional compounds is low. Moreover, the absorption of visible light by biological chromophores, in particular hemoglobin, limits the penetration depth to a few millimeters. Thus tumors that are buried deeper than a few millimeters in the tissue typically remain undetected. Furthermore ionization equilibrium of fluorescein (pKa=6.4) leads to pH-dependent absorption and emission over the range of 5 to 9. Therefore, the fluorescence of fluorescein-based dyes is quenched at low pH (below pH 5).

Therefore, NIR dyes conjugated to small molecule ligands that target PSMA [(a) Humblet V, Lapidus R, Williams L R, Tsukamoto T, Rojas C, Majer P, Hin B, Ohnishi S, De Grand A M, Zaheer A, Renze J T, Nakayama A, Slusher B S, Frangioni J V. Mol Imaging. 2005 October-December; 4(4):448-62.; (b) Thomas M, Kularatne S A, Qi L, Kleindl P, Leamon C P, Hansen M J, Low P S.; (c) Chen Y, Dhara S, Banerjee S R, Byun Y, Pullambhatla M, Mease R C, Pomper M G. Biochem Biophys Res Commun. 2009 Dec. 18; 390(3):624-9; (d) Nakajima T, Mitsunaga M, Bander N H, Heston W D, Choyke P L, Kobayashi H. Bioconjug Chem. 2011 Aug. 17; 22(8):1700-5.; (e) Chen Y, Pullambhatla M, Banerjee S R, Byun Y, Stathis M, Rojas C, Slusher B S, Mease R C, Pomper M G. Bioconjug Chem. 2012 Dec. 19; 23(12):2377-85.; (f) Laydner H, Huang S S, Heston W D, Autorino R, Wang X, Harsch K M, Magi-Galluzzi C, Isac W, Khanna R, Hu B, Escobar P, Chalikonda S, Rao P K, Haber G P, Kaouk J H, Stein R J. Urology. 2013 February; 81(2):451-6; (g) Kelderhouse L E, Chelvam V, Wayua C, Mahalingam S, Poh S, Kularatne S A, Low P S. Bioconjug Chem. 2013 Jun. 19; 24(6)1075-80.] have been tested as imaging agents in murine models of prostate cancer.

While these PSMA-targeted NIR dyes showed some labeling of prostate cancer cells in culture, they had very weak fluorescence in PSMA-expressing prostate tumor xenograft animal models. For example, the molecules described by, Humblet et al have shown very low tumor accumulation and florescence in the tumor xenograft models. It may be due the lack of proper linker between the ligand the NIR dye may have hindered the binding of ligand to the binding pocket in PSMA. On the other hand, phosphorous based ligands have less affinity for PSMA when compared to DUPA. Moreover, phosphorous based ligands are difficult to synthesize, involve multiple steps, and will be expensive to manufacture.

PSMA-targeted NIR agent reported in Chen et al has taken over 20 h to reach the tumor and 72 h clear from the non-targeted tissues. Also notably, this PSMA-targeted NIR dye has very slowly skin clearance. While binding epitope of PSMA in transfected cells that they used can be artificial, it had very low uptake and low fluorescence in PSMA transfected prostate cancer cell tumor. Furthermore, there is substantial non-specific uptake of this molecule in all other tissues and there is accumulation and fluorescence in PSMA-negative cells indicating non-specific and non-targeted nature of NIR conjugate reported by Chen et al.

Chen et al and Laydner et al have conjugated a small molecule ligand to IR800CW (a NIR dye). IR800CW is asymmetrical dye with activated carboxylic acid with n-hydroxysuccinimide ester (NHS). This is an extremely expensive molecule to synthesize and even more to purchase from commercially available resources (1 g is over $60,000). IR800CW also has the disadvantage that it is not stable during the synthesis due to two reasons: (a) hydrolysis of NHS ester, (b) hydrolysis of vinyl ether. The lack of stability of IR800CW conjugates during synthesis leads to formation of over 60% of undesired byproducts. This requires complex purification techniques indicating path for higher production cost, higher waiting period for clinical translation, and surgeons and patients will not have access to the drug.

Laydner et al conjugated a PSMA ligand to IR800CW via a long peptide space (6 amino acids) and bifunctional linker with NHS and maleimide. In addition to all the disadvantages caused by IR800CW, this PSMA-targeted IR800CW conjugate has a complicated synthesis scheme requiring synthesis in five stages (synthesis of ligand, conjugation of ligand to bifunctional linker via maleimide functional group, synthesis of peptide linker, conjugation of peptide linker to IR800CW, conjugation of peptide linker-IR800CW to ligand-bifunctional linker via amide bond) in multiple steps. Therefore, the manufacturing costs hamper the effective production of this molecule for clinical purposes. The synthesis scheme for these molecules is further complicated due to multiple chiral centers in the molecule. Peptide linkers, however, possess multiple chiral centers (stereoisomers) typically necessitating the need for production and assessment of all stereoisomers for FDA clearance. For example, a peptide linker possessing only 3 amino acids (i.e. 3 chiral centers), would require toxicity profiles for 8 different drug products since these heterogeneous mixtures could result in different affinities, efficacies, PK and safety profiles.

The small molecule ligand used by Laydner et al is GluNHCONHCys-SH. The free thiol moiety in Cys tends to oxidize hence the molecule has to be handled under argon or nitrogen environment and generally leads to an unstable molecule. GluNHCONHCys-SH ligand is conjugated to bifunctional linker via maleimide reaction. It is well reported that reactions between thiols and maleimide are reversible and yield 50% of the desired product. Moreover, maleimide bonds are not stable in circulation in the human body, hence use of maleimide bonds risk the release of the non-targeted dye leading to non-specific uptake thereof.

Kelderhouse et al conjugated DUPA-linker-Cys to Alexa flour 647 and Dylight 750 to DUPA via maleimide group. Again, these molecules have all the disadvantages associated with maleimide. Moreover, these low wave length NIR dyes, while being commercially available are very expensive. While molecules were tested on experimental metastatic mouse model, images were inconclusive.

Liu et al also reported PSMA-targeted NIR dye and some in vitro data but no animal data were reported. The lack of a proper linker between the ligand and the NIR dye may have attributed to the lack of vivo data. Moreover, this dye has many drawbacks as other reported compounds. It is a phosphorous based ligand and asymmetrical dye. So, it has disadvantages described of both phosphorous based ligands as well as asymmetrical NIR dyes.

Nakajima et al reported anti-PSMA antibody (J591) conjugated to ICG. Unfortunately, this compound took 72 hours to clear from the other healthy tissues such as liver. In addition, the compound remained in circulation for 6 days indicating that it will remain the body for over 30 days in human body. Moreover, ICG was tethered to J591 non-specifically via amide using either lysine residues in the protein leading to heterogeneous chemical entities which result in variable affinities, efficacies, PK and safety profiles. Lack of precise structural definition may limit progression of these conjugates for clinical use due to challenges associated with the production process and safety.

Higher non-specificity and slow clearance from the skin of reported PSMA-targeted NIR dyes may be due to poor pharmacokinetic (PK) properties of these compounds.

Thus, there remains a need for a dye substance that can be used to specifically target PSMA expressing cancer cells or neo-vasculature of diseased tissue with increased stability, better PK properties, higher solubility, fast tumor accumulation, high fluorescence, fast skin clearance, and higher tumor-to-background ratios (TBR) for use in vivo tissue imaging and to use in image-guided surgery.

BRIEF SUMMARY OF THE INVENTION

This disclosure provides PSMA-targeted ligands linked to NIR dyes via different linkers to improve clinical properties (e.g. stability, PK properties, solubility, fast tumor accumulation, higher fluorescence, fast skin clearance, and higher tumor-to-background ratios) of the compounds. The disclosure provides uses of the compounds in image-guided surgery and methods for synthesizing the same. This disclosure further provides variation of the total charge of the Ligand-Linker-NIR dye conjugate by adding positive charges to the linker or reducing number of negative charges in the dye molecules. This disclosure also provides novel higher affinity ligands to improve in vivo affinity and PK properties of NIR conjugates. This disclosure also provides compounds for use in the targeted imaging of tumors expressing PSMA, including but not limited to prostate cancer, and methods of use, for example, in imaging and surgery involving PSMA positive tissues and tumors.

In certain embodiments, compounds of the present invention have the form:

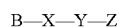

wherein B is a PSMA-targeted molecule;
X is a linker;
Y is an amino acid linker; and
Z is a NIR dye.

In some embodiments, the PSMA-targeted molecule is chosen from the group consisting of a small molecule, a ligand, an inhibitor, an agonist or a derivative thereof. In some embodiments, the PSMA-targeted compound is a ligand. In some embodiments, the PSMA-targeted compound is DUPA. In other embodiments, the PSMA-targeted compound is a small molecule that binds PSMA.

In some embodiments, X is a hydrophobic linker. In some embodiments, X is selected from the group consisting of a polyethylene glycol (PEG) sequence including 1, 2, 3, or 4 PEG monomers, a chain of 7 atoms, a linker 7 atoms in length, a chain from 7 to 24 atoms in length; a peptide comprising two aryl or aryl alkyl groups, each of which is optionally substituted, and where one aryl or aryl alkyl group is about 7 to about 11, or about 7 to about 14 atoms, and the other aryl or aryl alkyl group is about 10 to about 14, or about 10 to about 17 atoms. In another embodiment, the linker ccomprises about 1 to about 30 atoms, or about 2 to about 20 atoms. In some embodiments, the linker is 7 atoms in length. In some embodiments, the linker comprises $PEG_2$. In some embodiments, the linker is variably charged. In some embodiments, X has a positive charge. In other embodiments, X has a negative charge.

In some embodiments, Y is selected from the group consisting of: acidic (negatively charged) amino acids, such as aspartic acid and glutamic acid and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof; neutral nonpolar (hydrophobic) amino acids, such as alanine, leucine, isoleucine, valine, proline, phenylalanine, tryptophan, and methionine; and derivatives thereof. In some embodiments, Y is an aromatic amino acid and derivative thereof. In some embodiments, Y has a positive charge. In other embodiments, Y has a negative charge.

In some embodiments, Z is selected from the group consisting of near-infra red dyes, including but not limited to,

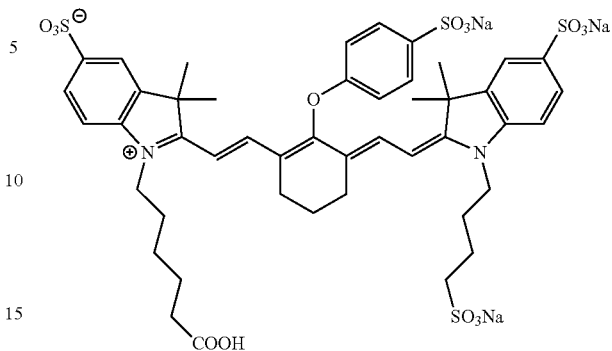

IR800

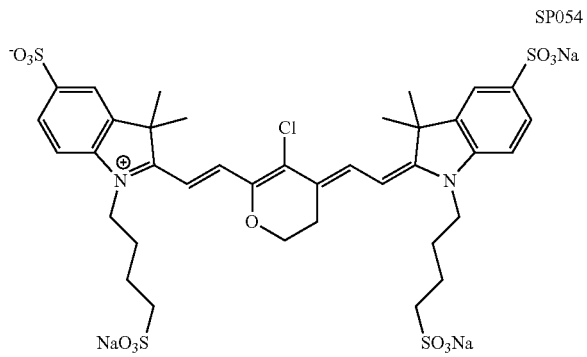

SP054

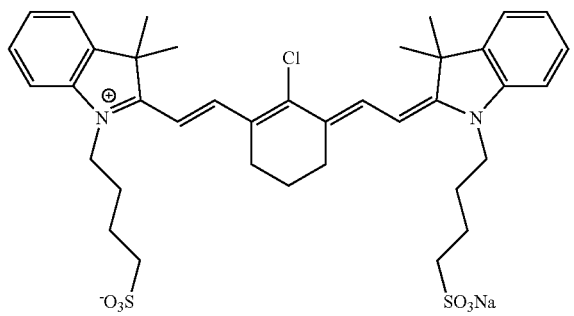

S0121

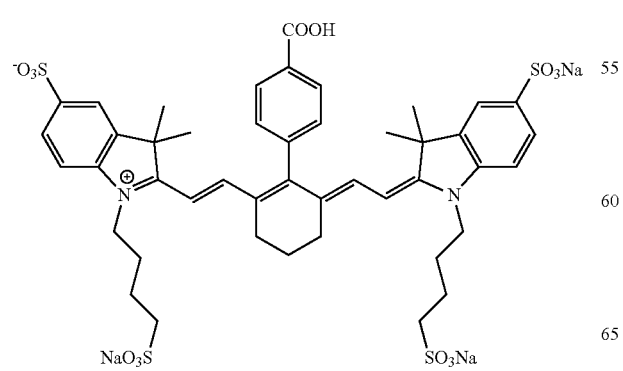

LS288

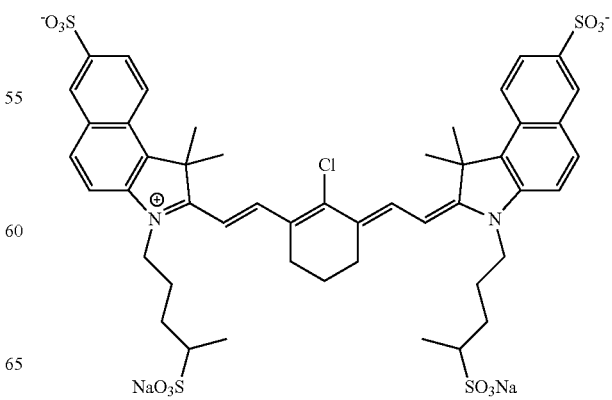

S2076

-continued
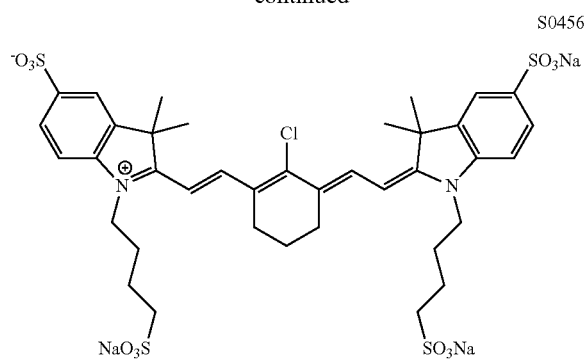
S0456
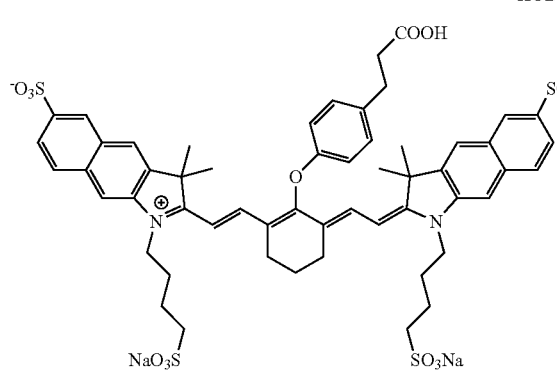
KODAK
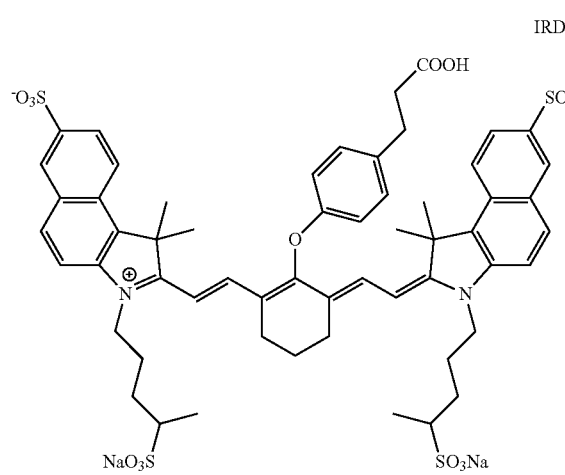
IRD28
and/or the dyes selected from group consisting of:
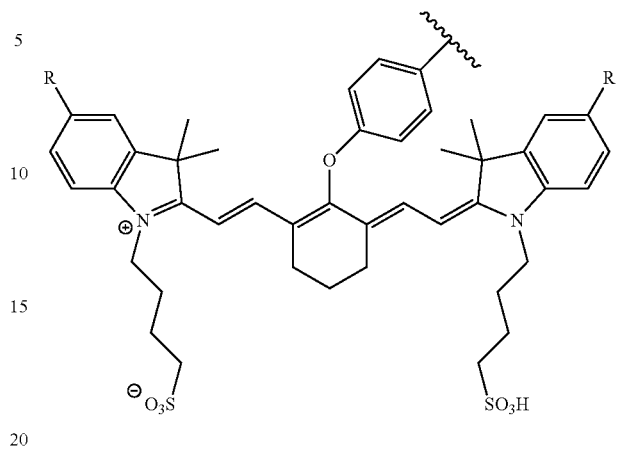
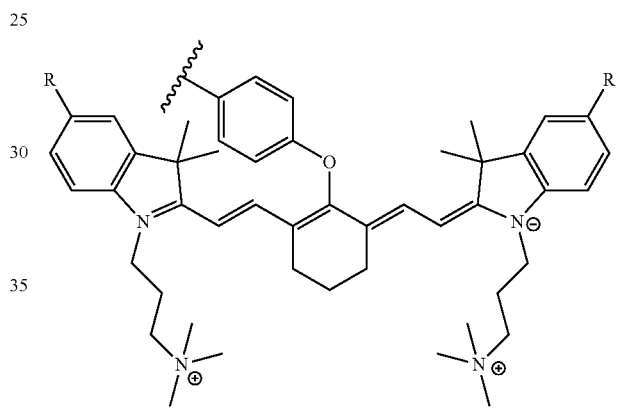
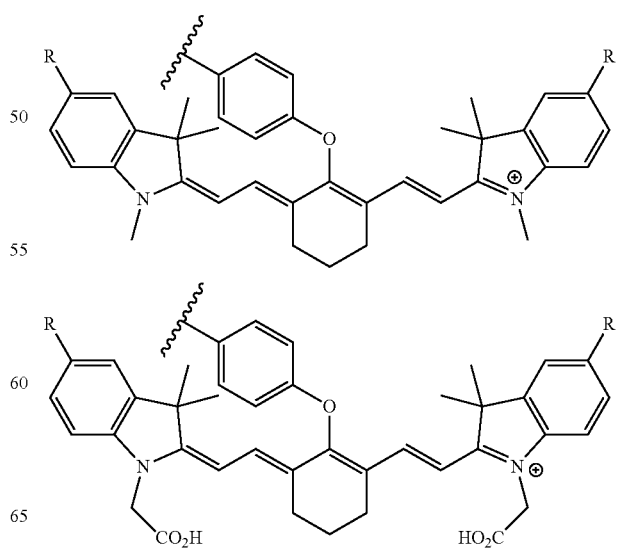

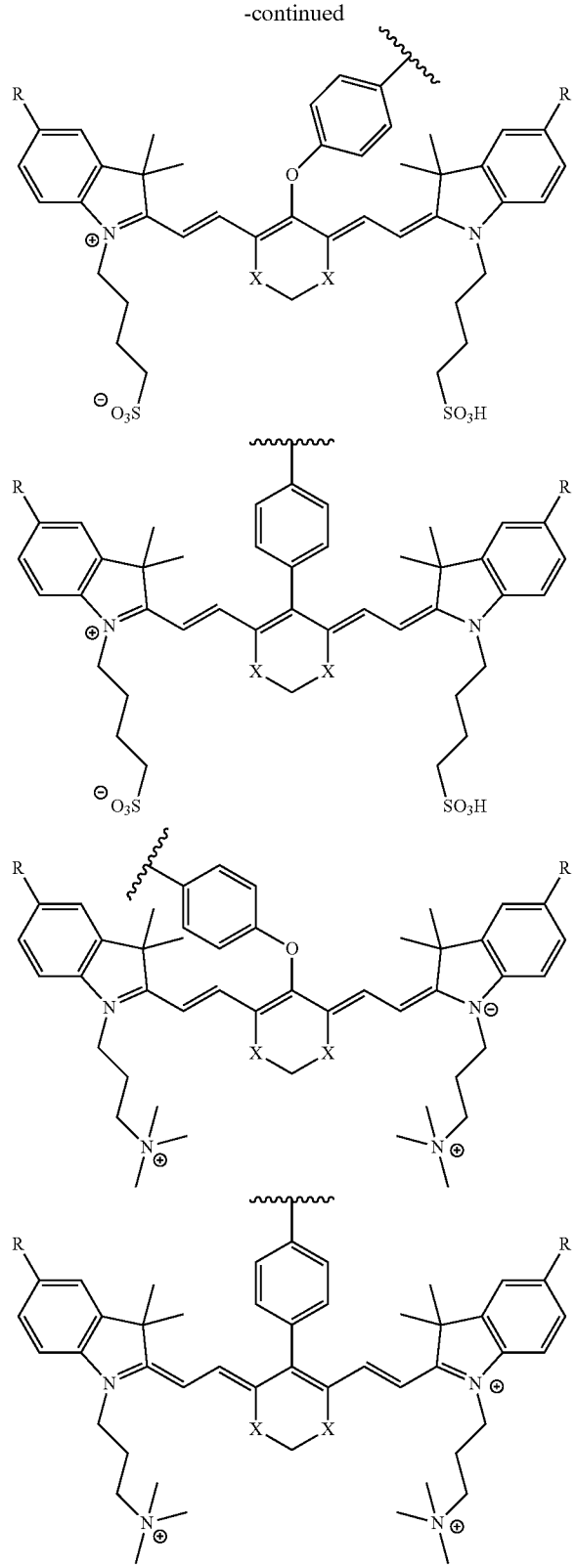

R = H or R = SO₃H; X = O, S, N

In certain embodiments, the Z is variably charged. In some embodiments, Z has a positive charge. In other embodiments, Z has a negative charge.

In certain embodiments, compounds of the present invention have the formula:

B—X—Y—Z wherein B is a PSMA-targeted compound; X is a linker; Y is an amino acid linker with a sulfur-containing side chain group; and Z is an NIR dye. In some embodiments, the amino acid linker with a sulfur-containing side group is cysteine. In some embodiments, the amino acid linker with a sulfur-containing side group is methionine. In some embodiments, the amino acid linker with a sulfur-containing side group is molecule containing thiophenol moiety.

In some embodiments, compounds of the present invention have the form:

B—X—Y—Z wherein B is a PSMA-targeted compound; X is a linker; Y is an amino acid linker with a chalcogen-containing side chain group; and Z is an NIR dye.

In some embodiments the present invention provides compounds of the form:

B—X—Y—Z

Wherein, B is a PSMA-targeted compound; X is a linker; Y is an amino acid chosen from the group consisting of tyrosine, cysteine, lysine, or a derivative thereof; and Z is an NIR dye. In some embodiments, Y comprises a tyrosine or tyrosine derivative. In some embodiments, Y comprises a tyrosine and a carbon isotope is on the aromatic ring of tyrosine. In some embodiments, Y comprises an amino acid with an aromatic ring with a hydrogen isotope.

In some embodiments the invention includes the compound B—X—Y—Z wherein B comprises DUPA or a derivative thereof, X comprises an EAOA, Y comprises tyrosine, and Z comprises S0456.

The present invention also relates to a compound having the formula:

(I)

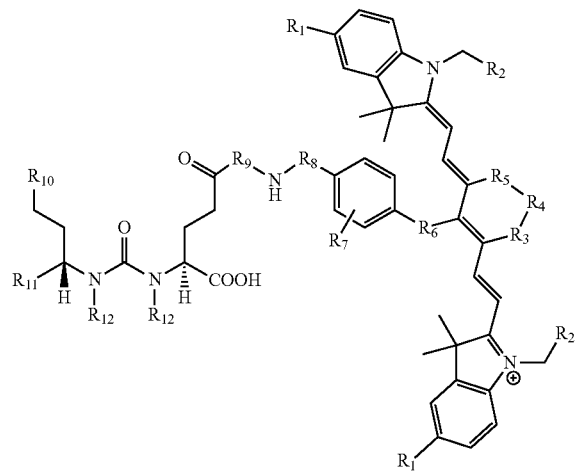

or a pharmaceutically acceptable salt thereof, or isotopes thereof, wherein:
$R_1$ represents a hydrogen or $SO_3H$;
$R_2$ represents a hydrogen, $CH_3$, $C_3H_6SO_3^-$, $C_3H_6SO_3H$ or $C_4H_8SO_3^-$, or $C_4H_8SO_3H$ or $C_3H_6N^+(CH_3)_3$;
$R_3$, and $R_5$ each represents a carbon, optionally one or more sharing bonds, $R_4$ represents a carbon with optionally one or more sharing bonds;

$R_6$ represents nitrogen, oxygen, or sulfur or no atom (direct C—C bond between aromatic ring and vinyl ring);

$R_7$ is optional and when present represents aromatic substitution group to enhance the spectral properties such as increase brightness and stability of the vinyl ether bridge;

$R_8$ is optional and when present represents linkers with aromatic amino acids such as Phe, Trp, His or derivative thereof, cationic amino acids such Arg, Lys, or derivative thereof, anionic amino acids such as Asp, Glu or derivative of them, unnatural amino acids of aromatic/cationic/anionic acids or derivative thereof;

$R_9$ is optional and when present represents a linear carbon chain, or polyethylene glycol linker, cationic linker, or derivative thereof;

$R_{10}$ represents a $CO_2H$, $PO_3H_2$, $SO_3H$, $CH_2SO_3H$, $CH_2CONHCH_2SO_3H$, $CH_2CONHCH_2CH_2SO_3H$;

$R_{11}$ represents $CO_2H$, $SO_3H$, $CH_2CONHCH_2SO_3H$, $CH_2CONHCH_2CH_2SO_3H$; and $R_{12}$ represents a hydrogen, a methyl group, a $CH_2$ and may optionally represent each a $CH_2$ sharing a bond.

In some embodiments compounds of the present invention have an absorption and emission maxima between about 500 nm and about 900 nm. In some embodiments compounds of the present invention have an absorption and emission maxima between about 600 nm and 800 nm.

In some embodiments compounds of the present invention are made to fluoresce after distribution thereof in the tissue cells. In some embodiments compounds of the present invention are made to fluoresce by subjecting the compounds to excitation light of near infrared wavelength. In some embodiments compounds of the present invention have a binding affinity to PSMA that is similar to the binding affinity of DUPA. In some embodiments compounds of the present invention are highly selective for targeting to a tumor cell. In particularly preferred embodiments, the compounds of the present invention are targeted to prostate cancer cells.

In certain embodiments compounds of the present invention are administered to a subject in need thereof and in some embodiments the administered composition comprises, in addition to the compound, a pharmaceutically acceptable carrier, excipient or diluent.

Some embodiments of the present invention provide a kit comprising a PSMA-targeting NIR dye compound. In some embodiments, the kit is used for the imaging of PSMA-expressing cells. In some embodiments the PSMA-expressing cells are tumor cells. In some embodiments the PSMA-expressing cells are non-prostate cancer cells. In certain embodiments the PSMA-expressing cells are prostate tumor cells. In certain embodiments the PSMA-expressing cells are cancer cells. In certain embodiments the PSMA-expressing area is neo-vasculature of tumor cells. In some embodiments the present invention is used for detection of metastatic disease. In some embodiments compounds of the present invention are used for improved surgical resection and/or improved prognosis. In some embodiments methods of the present invention provide cleaner surgical margins than non-NIR conjugated fluorescing dyes. In some embodiments PSMA-targeted NIR dye compounds of the present invention have an improved tumor-to-background ratio.

In another embodiment, methods for treating diseases and disease states, diagnosing diseases or disease states, and/or imaging tissues and/or cells that are associated with pathogenic populations of cells expressing or over expressing PSMA are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing PSMA.

DEFINITIONS

Figure 1:
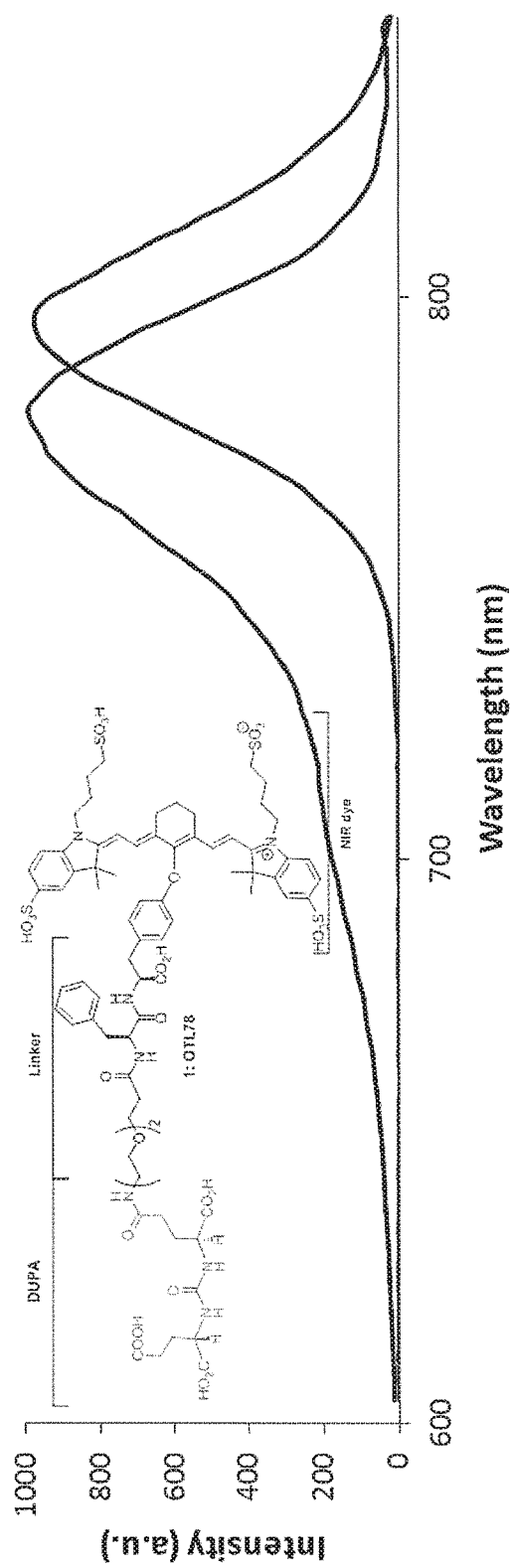
FIG. 1 depicts the chemical structure, excitation and emission spectra of 1: OTL78.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "prostate specific membrane antigen ligand" "PSMA ligand" is a reference to one or more such ligands and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

With respect to PSMA-targeted NIR conjugates of the present invention, the term "antigenically specific" or "specifically binds" refers to PSMA-targeting compounds that bind to one or more epitopes of PSMA, but which do not substantially recognize and bind other molecules in a sample containing a mixed population of antigens.

The term "epitope" as used herein refers to a site on PSMA that is recognized by DUPA. An epitope may be a linear or conformationally formed sequence or the shape of amino acids.

As used herein, "PSMA-targeting compound" or "PSMA-targeted compound" shall include those small molecules, ligands, polypeptides and proteins that have at least the biological activity of specific binding to PSMA or an epitope of PSMA. These compounds include ligands, receptors, peptides, or any amino acid sequence that binds to PSMA or to at least one PSMA epitope.

Compounds of the present invention comprise a PSMA-targeting compound, they may bind a portion of PSMA itself, or they may bind a cell surface protein or receptor that is associated with PSMA.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission.

The present invention addresses, among other things, problems associated with the early diagnosis and surgical treatment of PSMA-expressing cells involved in disease and/or cancer, and in particular PSMA-targeted dye conjugates with improved imaging, diagnostic, biological properties including, as non-limiting examples, higher specificity, decreased background signal and increased tumor fluorescence.

DETAILED DESCRIPTION

Surgery cures 50% of patients with solid tumors in the US, while chemo- and radiotherapy cure less than 5% of all cancer patients. Over 700,000 patients undergo cancer surgery every year in the US and 40% of surgical patients have a recurrence of locoregional disease within 5 years. Despite major advances in the field of oncology there remains a need for early detection, methods to overcome hurdles to complete surgical resection of the primary tumor with negative margins, and removal of metastatic cancer cells and identification of satellite disease. Achieving these three goals not only improves disease clearance but also guides decisions regarding postoperative chemotherapy and radiation. While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, fluorescein-based dyes have the disadvantages that of low shelf-life stability. Thiourea bridge formed by Fluorescence isothiocynate (FITC) compounds easily decomposes making unstable compound. In addition, as EC17 uses fluorescein which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. Therefore, conventional dyes cannot readily detect tumors that may be buried deeper than a few millimeters in the tissue. Furthermore, fluorescence from fluorescein is quenched at low pH (below pH 5).

In order for a dye material to be useful in detecting and guiding surgery or providing detection of early, metastatic, and other tissue imaging it is important to overcome these drawbacks. The present invention provides PSMA-targeted conjugates of near infrared dyes that are stable, fluoresce in the infrared range, penetrate deep within targeted tissue to produce a specific and bright identification of areas of tissue that express PSMA, fast clearance from tissues that do not express PSMA to obtain high tumor-to-background ratio, and fast skin clearance. More specifically, the PSMA-targeted conjugates are linked to the near infrared dyes through a linker consisting of one or more atomic linkers, amino acids, amino acid derivatives. Even more specifically, it has been found that where the atomic linker is hydrophobic 7-atom linker with neutral or charged atoms and amino acid linker is aromatic amino acid or a derivative of aromatic amino acid, or negative or positive charge amino acid and tyrosine or a derivative of tyrosine. Charge of the linker can be varied to obtain fast skin clearance and fast tumor accumulation to obtain higher tumor-to-background ratio. Moreover, the fluorescence intensity of the NIR dye is maintained or even enhanced by having the aromatic amino acid or tyrosine or derivative of tyrosine and charge of the NIR dye can be varied to accomplish fast skin clearance.

This disclosure provides PSMA-targeted ligands linked to NIR dyes and methods for synthesizing the same. This disclosure also provides compounds for use in the targeted imaging of tumors expressing PSMA, including but not limited to prostate cancer, and methods of use, for example, in imaging and surgery involving PSMA positive tissues and tumors.

In certain embodiments, compounds of the present invention have the form:

B—X—Y—Z wherein B is a PSMA-targeted compound;

X is a linker;

Y is an amino acid linker; and

Z is an NIR dye.

In some embodiments, the PSMA-targeted compound is chosen from the group consisting of a small molecule, a ligand, or a derivative thereof. In some embodiments, the PSMA-targeted compound is a ligand. In some embodiments, the PSMA-targeted compound is DUPA. In other embodiments, the PSMA-targeted compound is a small molecule that binds PSMA.

In some embodiments, X is a hydrophobic linker. In some embodoiments, X is selected from the group consisting of an eight aminooctonoic acid (EAOA), a chain of 7 atoms, polyethylene glycol linker, a linker 7 atoms in length, cationic linker, chain of 7 atoms, a chain from 7 to 24 atoms in length; a peptide comprising two aryl or aryl alkyl groups, each of which is optionally substituted, and where one aryl or aryl alkyl group is about 7 to about 11, or about 7 to about 14 atoms, and the other aryl or aryl alkyl group is about 10 to about 14, or about 10 to about 17 atoms. In another embodiment, the linker ccomprises about 1 to about 30 atoms, or about 2 to about 20 atoms. In some embodiments, the linker is 7 atoms in length. In some embodiments, the linker comprises EAOA. In some embodiments, the linker is variably charged. In some embodiments, X has a positive charge. In other embodiments, X has a negative charge.

In some embodiments, Y is selected from the group consisting of: acidic (negatively charged) amino acids, such as aspartic acid and glutamic acid; basic (positively charged) amino acids such as arginine, histidine, and lysine; neutral polar amino acids, such as glycine, serine, threonine, cysteine, tyrosine, asparagine, and glutamine; neutral nonpolar (hydrophobic) amino acids, such as alanine, leucine, isoleucine, valine, proline, phenylalanine, tryptophan, and methionine; and derivatives thereof. In some embodiments, Y is an aromatic amino acid. In some embodiments, Y has a positive charge. In other embodiments, Y has a negative charge.

In some embodiments, Z is selected from the group consisting of near-infra red dyes, including but not limited to,

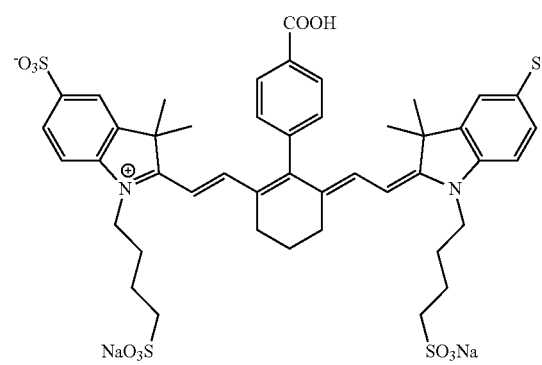
LS288
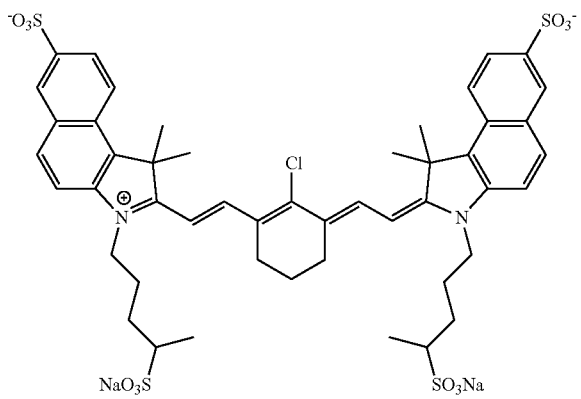
S2076
IR800
S0456
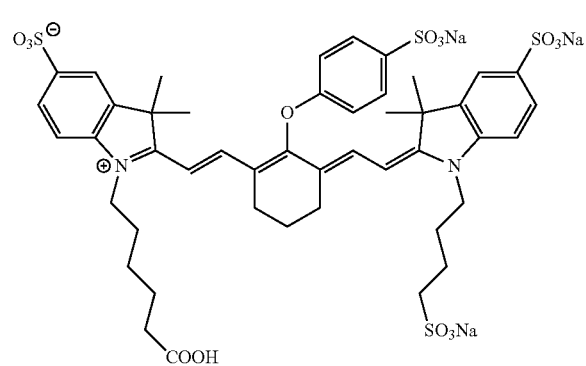
SP054
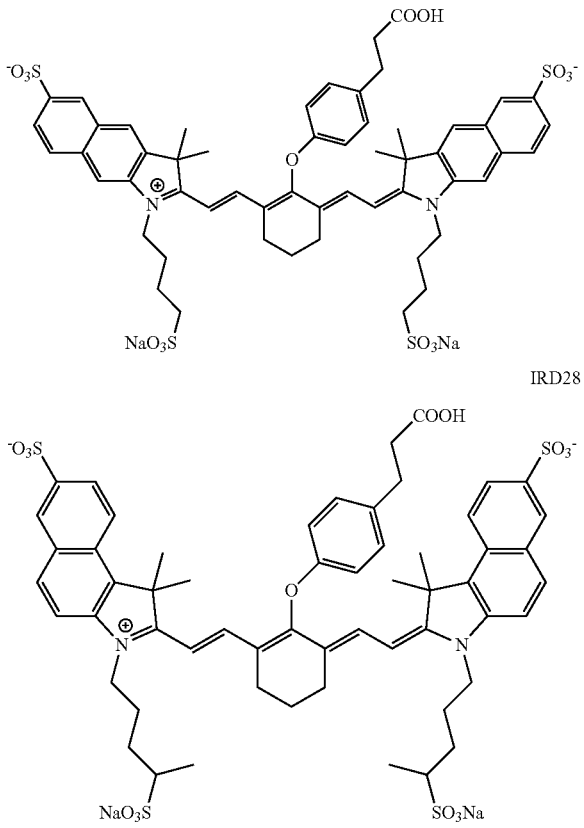
KODAK
S0121
IRD28 and/or the dyes selected from group consisting of
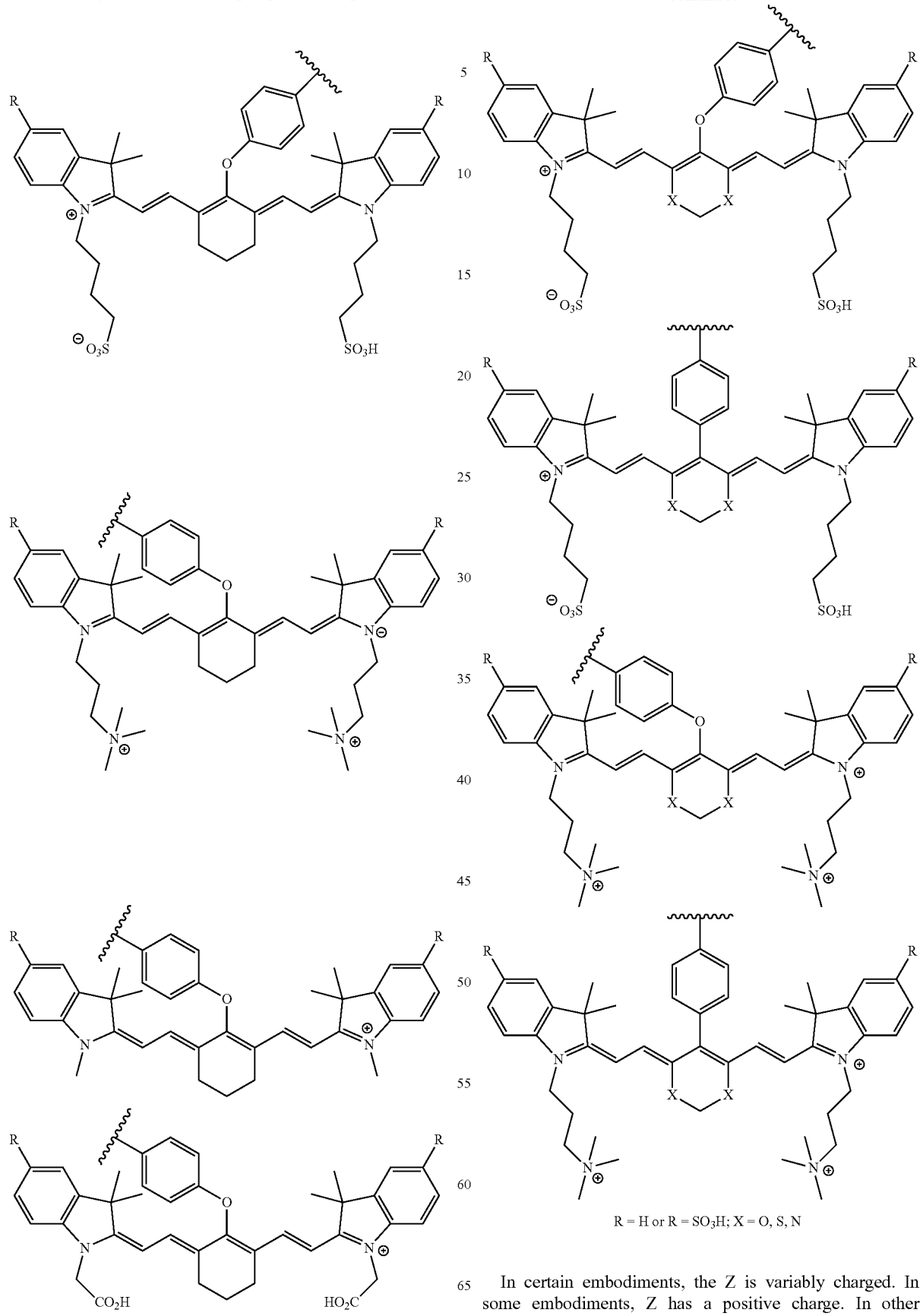
R = H or R = SO$_3$H; X = O, S, N
In certain embodiments, the Z is variably charged. In some embodiments, Z has a positive charge. In other embodiments, Z has a negative charge.

In certain embodiments, compounds of the present invention have the form:

B—X—Y—Z wherein B is a PSMA-targeted compound; X is a linker; Y is an amino acid linker with a sulfur-containing side chain group; and Z is an NIR dye. In some embodiments, the amino acid linker with a sulfur-containing side group is cysteine. In some embodiments, the amino acid linker with a sulfur-containing side group is methionine. In some embodiments, the amino acid linker with a sulfur-containing side group is molecule containing thiophenol moiety. In some embodiments, compounds of the present invention have the form:

B—X—Y—Z wherein B is a PSMA-targeted compound; X is a linker; Y is an amino acid linker with a chalcogen-containing side chain group; and Z is an NIR dye. In some embodiments the present invention provides compounds of the form:

B—X—Y—Z wherein B is a PSMA-targeted compound; X is a linker; Y is an amino acid chosen from the group consisting of tyrosine, cysteine, lysine, or a derivative thereof; and Z is an NIR dye. In some embodiments, Y comprises a tyrosine or tyrosine derivative. In some embodiments, Y comprises a tyrosine and a carbon isotope is on the aromatic ring of tyrosine. In some embodiments, Y comprises an amino acid with an aromatic ring with a hydrogen isotope.

In some embodiments, compounds of the present invention have the form:

B—X—Y—Z wherein B is a PSMA-targeted compound; X is a linker; Z is an NIR dye; and Y comprises a derivative of tyrosine selected from the group consisting of:

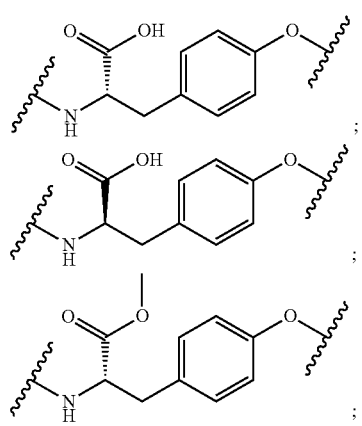

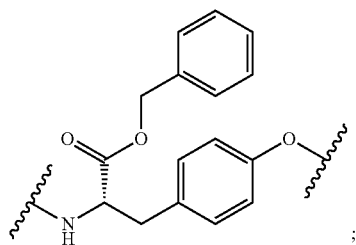

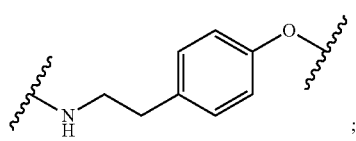

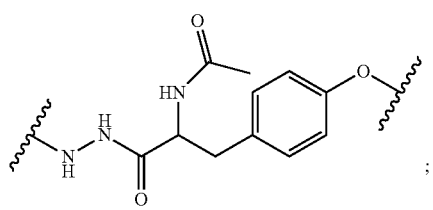

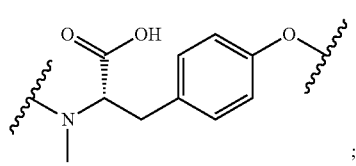

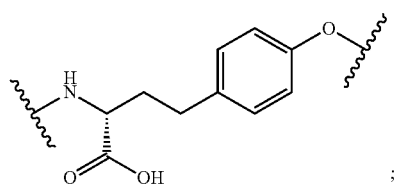
; and

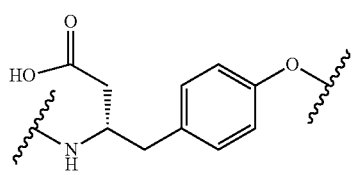

or racemic mixtures thereof.

In some embodiments the invention includes the compound B—X—Y—Z wherein B comprises DUPA or a derivative thereof, X comprises an EAOA, Y comprises tyrosine, and Z comprises S0456.

In some embodiments the present invention a compound that has the formula:

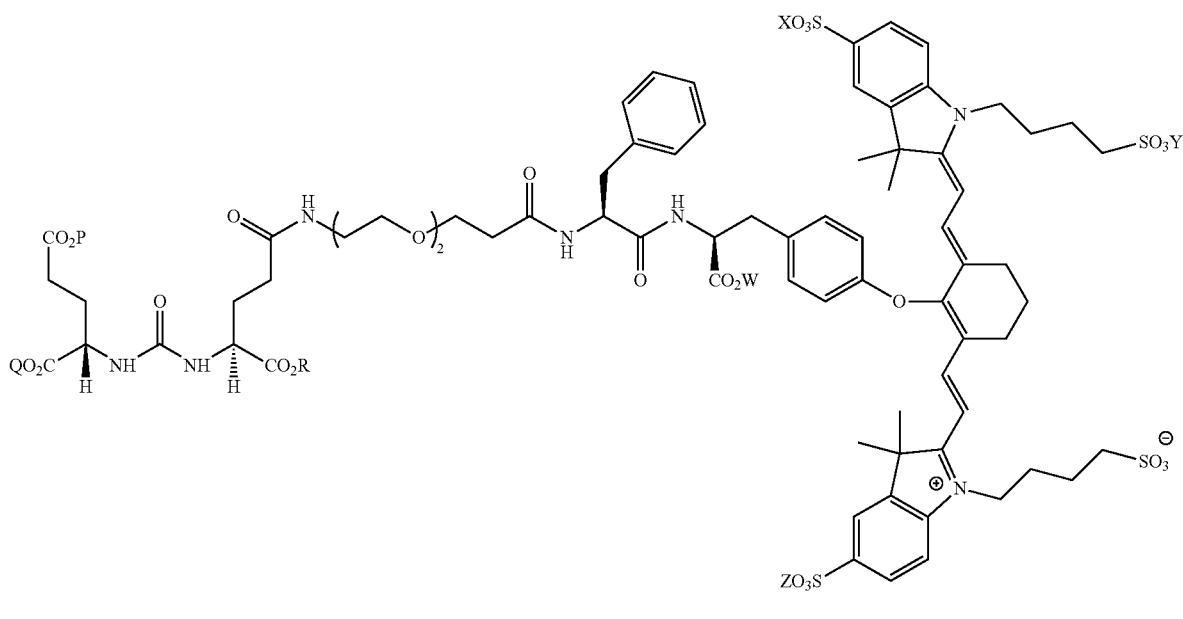

P, Q, R, W, X, Y, Z can be H, Na, K, NH₄

In some embodiments compounds of the present invention have an absorption and emission maxima between about 500 nm and about 900 nm. In some embodiments compounds of the present invention have an absorption and emission maxima between about 600 nm and 800 nm.

In some embodiments compounds of the present invention are made to fluoresce after distribution thereof in the tissue cells. In some embodiments compounds of the present invention are made to fluoresce by subjecting the compounds to excitation light of near infrared wavelength. In some embodiments compounds of the present invention have a binding affinity to PSMA that is similar to the binding affinity of DUPA. In some embodiments compounds of the present invention are highly selective for targeting to a tumor cell.

In certain embodiments compounds of the present invention are administered to a subject in need thereof and in some embodiments the administered composition comprises, in addition to the compound, a pharmaceutically acceptable carrier, excipient or diluent.

Some embodiments of the present invention provide methods of optical imaging of PSMA-expressing biological tissue, said method comprising:
(a) contacting the biological tissue with a composition comprising a PSMA-targeted NIR dye compound,
(b) allowing time for the compound in the composition to distribute within the biological target;
(c) illuminating the tissue with an excitation light of a wavelength absorbable by the compound; and
(d) detecting an optical signal emitted by the compound.

In some embodiments, these methods are used in detection of diseases associated with high PSMA expression. In some embodiments, further comprising the step of constructing an image from the signal emitted in (d). In some embodiments, the invention provides the aforementioned method wherein step (a) includes two or more fluorescent compounds whose signal properties are distinguishable are contacted with the tissue, and optionally the tissue is in a subject. In some embodiments the present invention provides use of an endoscope, catheter, tomographic system, hand-held optical imaging system, surgical goggles, or intraoperative microscope for the illuminating and/or detecting method steps.

In some embodiments, compositions and methods of the present invention are used to treat cancer. In some embodiments, the cancer is selected from the group consisting of prostate cancer, bladder cancer, pancreatic cancer, liver cancer, lung cancer, kidney cancer, sarcoma, breast cancer, brain cancer, neuroendocrine carcinoma, colon cancer, testicular cancer or melanoma. In some embodiments, PSMA-targeted NIR dye compounds of the present invention are used for imaging of PSMA-expressing cells. In certain embodiments those cells are chosen from the group consisting of prostate cells, prostate cancer cells, bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells;

The present invention also provides methods of targeting a cell type in a biological sample comprising: a) contacting the biological sample with a PSMA-targeted NIR dye compound for a time and under conditions that allow for binding of the compound to at least one cell of the target cell type; and b) optically detecting the presence or absence of the compound of in the biological sample, wherein presence of the compound in detecting step c) indicates that the target cell type is present in the biological sample. In some embodiments the present invention provides methods for optical detection of PSMA-expressing cells comprising administering PSMA-targeting NIR dye compounds of the present invention and subjecting the compound to an excitation light source and detecting fluorescence from the compound. In some embodiments, the excitation light source is near-infrared wavelength light. In some embodiments the excitation light wavelength is within a range from about 600 to 1000 nanometers. In some embodiments the excitation light wavelength is within a range from about 670 to 850 nanometers.

In certain embodiments the present invention provides methods of performing image guided surgery on a subject comprising:
a) administering a composition comprising a PSMA-targeting NIR dye compound under conditions and for a time sufficient for the compound to accumulate at a given surgical site;
b) illuminating the compound to visualize the compound using infrared light; and
c) performing surgical resection of the areas that fluoresce upon excitation by the infrared light.

In some embodiments methods of the present invention the infrared light wavelength is within a range from about 600 to 1000 nanometers. In some embodiments methods of the present invention use an infrared light wavelength is within a range from about 670 to 850 nanometers.

Some embodiments of the present invention provide a method of diagnosing a disease in a subject comprising:
a) administering to a subject in need of diagnosis an amount of a PSMA-targeted NIR dye compound for a time and under conditions that allow for binding of the compound to at least one PSMA-expressing cell or tissues (PSMA also express in neo-vasculature of most of the solid tumors);
b) measuring the signal from the compound of present in the biological sample;
c) comparing the signal measured in b) with at least one control data set, wherein the at least one control data set comprises signals from the compound of claim 1 contacted with a biological sample that does not comprise the target cell type; and
d) providing a diagnosis of disease wherein the comparison in step c) indicates the presence of the disease.

Some embodiments of the present invention provide a kit comprising a PSMA-targeting NIR dye compound. In some embodiments, the kit is used for the imaging of PSMA-expressing cells or tissues. In some embodiments the PSMA-expressing cells are tumor cells. In some embodiments the PSMA-expressing cells are non-prostate cancer cells. In certain embodiments the PSMA-expressing cells are prostate tumor cells. In certain embodiments the PSMA-expressing cells are cancer cells. In some embodiments the present invention is used for detection of metastatic disease. In some embodiments compounds of the present invention are used for improved surgical resection and/or improved prognosis. In some embodiments methods of the present invention provide cleaner surgical margins than non-NIR conjugated fluorescing dyes. In some embodiments PSMA-targeted NIR dye compounds of the present invention have an improved tumor-to-background ratio.

In other embodiments compounds of the present invention are used to image, diagnose, or detect non-prostate cancer cells chosen from the group consisting of bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells. In other embodiments, the cells being detected are more than 5 mm below the skin. In some embodiments, the tissue being detected is more than 5 mm below the skin. In other embodiments, the tumor being detected is more than 5 mm below the skin. In some embodiments, the cells being detected are more than 6 mm, 7 mm, 8 mm, 9 mm, or 10 mm below the subject's skin. In some embodiments of the present invention dye probes that are detectable outside of the visible light spectrum. In some embodiments dye probes greater than the visible light spectrum are used. In some embodiments compounds of the present invention comprise dye probes sensitive to wavelengths between 650 nm and 900 nm. In some embodiments the PSMA-targeted NIR dye compounds of the present invention have maximum light absorption wavelengths in the near infrared region of between about 650 nm and 1000 nm, for example and in one embodiment, at approximately 800 nm.

In still another embodiment of the methods provided, the non-prostate cancer is bladder cancer, pancreatic cancer, liver cancer, lung cancer, kidney cancer, sarcoma, breast cancer, brain cancer, neuroendocrine carcinoma, colon cancer, testicular cancer or melanoma.

In some embodiments the present disclosure relates to prostate specific membrane antigen (PSMA) targeted compounds conjugated to near-infra red (NIR) dyes and methods for their therapeutic and diagnostic use. More specifically, this disclosure provides compounds and methods for diagnosing and treating diseases associated with cells expressing prostate specific membrane antigen (PSMA), such as prostate cancer and related diseases. The disclosure further describes methods and compositions for making and using the compounds, methods incorporating the compounds, and kits incorporating the compounds. It has been discovered that a PSMA-targeted compound, such as DUPA or conjugating PSMA-targeting ligand to an NIR dye via a linker (L) may be useful in the imaging, diagnosis, and/or treatment of prostate cancer, and related diseases that involve pathogenic cell populations expressing or over-expressing PSMA. PSMA is a cell surface protein that is internalized in a process analogous to endocytosis observed with cell surface receptors, such as vitamin receptors. PSMA also express in the neo-vasculature of most of solid tumors. Accordingly, it has been discovered that certain conjugates that include a linker having a predetermined length, and/or a predetermined diameter, and/or preselected functional groups along its length may be used to treat, image, and/or diagnose such diseases.

In one illustrative embodiment, the linker L may be a releasable or non-releasable linker. In one aspect, the linker L is at least about 7 atoms in length. In one variation, the linker L is at least about 10 atoms in length. In one variation, the linker L is at least about 14 atoms in length. In another variation, the linker L is between about 7 and about 22 , between about 7 and about 24, or between about 7 and about 20 atoms in length. In another variation, the linker L is between about 14 and about 31, between about 14 and about 24, or between about 14 and about 20 atoms in length.

In an alternative aspect, the linker L is at least about 10 angstroms (A) in length.

In one variation, the linker L is at least about 15 A in length. In another variation, the linker L is at least about 20 A in length. In another variation, the linker L is in the range from about 10 A to about 30 A in length.

In an alternative aspect, at least a portion of the length of the linker L is about 5 A in diameter or less at the end connected to the binding ligand B. In one variation, at least a portion of the length of the linker L is about 4 A or less, or about 3 A or less in diameter at the end connected to the binding ligand B. It is appreciated that the illustrative embodiments that include a diameter requirement of about 5 A or less, about 4 A or less, or about 3 A or less may include that requirement for a predetermined length of the linker, thereby defining a cylindrical-like portion of the linker. Illustratively, in another variation, the linker includes a cylindrical portion at the end connected to the binding ligand that is at least about 7 Å in length and about 5 Å or less, about 4 Å or less, or about 3 Å or less in diameter.

In another embodiment, the linker L includes one or more hydrophilic linkers capable of interacting with one or more residues of PSMA, including amino acids that have hydrophilic side chains, such as Ser, Thr, Cys, Arg, Orn, Lys, Asp, Glu, Gln, and like residues. In another embodiment, the linker L includes one or more hydrophobic linkers capable of interacting with one or more residues of PSMA, including amino acids that have hydrophobic side chains, such as Val, Leu, Phe, Tyr, Met, and like residues. It is to be understood that the foregoing embodiments and aspects may be included in the linker L either alone or in combination with each other. For example, linkers L that are at least about 7 atoms in length and about 5 Å, about 4 Å or less, or about 3 Å or less in diameter or less are contemplated and described herein, and also include one or more hydrophilic linkers capable of interacting with one or more residues of PSMA, including Val, Leu, Phe, Tyr, Met, and like residues are contemplated and described herein.

In another embodiment, one end of the linker is not branched and comprises a chain of carbon, oxygen, nitrogen, and sulfur atoms. In one embodiment, the linear chain of carbon, oxygen, nitrogen, and sulfur atoms is at least 5 atoms in length. In one variation, the linear chain is at least 7 atoms, or at least 10 atoms in length. In another embodiment, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (L) comprising the dipeptide Phe-Phe may include a piperazin-1,4-diyl structure by cyclizing two nitrogens with an ethylene fragment, or substituted variation thereof.

In another embodiment, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing PSMA. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing PSMA are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing PSMA.

In some embodiments, it is shown herein that such PSMA-targeted NIR dye conjugates bind to PSMA expressing tumor cells within a tissue. Moreover, the intensity of the fluorescence in greater than the intensity of previously observed with other near infrared dyes that are targeted with folate for folate receptor positive tumors. This increased intensity allows the targeting and clear identification of smaller areas of biological samples (e.g., smaller tumors) from a tissue being monitored. In addition, the increased intensity of the compounds of the present invention provides the added advantage that lower doses/quantities of the dye can be administered and still produces meaningful results.

Thus, the compounds of the present invention lead to more economical imaging techniques. Moreover, there is an added advantaged that a lower dose of the compounds of the invention as compared to conventional imaging compounds minimizes the toxicity and other side effects that are attendant with administration of foreign materials to a body.

Furthermore, identification of small tumors will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

In specific embodiments, it is contemplated that in addition to tyrosine and tyrosine derivatives, a PSMA-targeted conjugate of a near infrared dye with cysteine or cysteine derivatives also may be useful. Furthermore, it is contemplated that a direct linkage of the PSMA-targeted moiety to the dye or linkage of the dye to DUPA or a PSMA-targeted ligand through an amine linker also produces a loss of intensity of the fluorescence from the conjugate whereas the presence of the tyrosine or tyrosine derivative as the linking moiety between enhances the fluorescence of the conjugated compound as a result of the fact that the tyrosine-based compounds of the invention do not require an extra amine linker to conjugate the SO456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

In specific embodiments, the linker is less than ten atoms. In other embodiments, the linker is less than twenty atoms. In some embodiments, the linker is less than 30 atoms. In some embodiments, the linker is defined by the number of atoms separating the PSMA-targeting compound and the NIR dye. In another embodiment, linkers have a chain length of at least 7 atoms. In some embodiments, linkers have a chain length of at least 14 atoms. In another embodiment, linkers have a chain length in the range from 7 atoms to 20 atoms. In another embodiment, linkers have a chain length in the range of 14 atoms to 24 atoms.

PSMA-targeting compounds suitable for use in the present invention can be selected, for example, based on the following criteria, which are not intended to be exclusive: binding to live cells expressing PSMA; binding to neovasculature expressing PSMA; high affinity of binding to PSMA; binding to a unique epitope on PSMA (to eliminate the possibility that antibodies with complimentary activities when used in combination would compete for binding to the same epitope); opsonization of cells expressing PSMA; mediation of growth inhibition, phagocytosis and/or killing of cells expressing PSMA in the presence of effector cells; modulation (inhibition or enhancement) of NAALADase, folate hydrolase, dipeptidyl peptidase IV and/or γ-glutamyl hydrolase activities; growth inhibition, cell cycle arrest and/or cytotoxicity in the absence of effector cells; internalization of PSMA; binding to a conformational epitope on PSMA; minimal cross-reactivity with cells or tissues that do not express PSMA; and preferential binding to dimeric forms of PSMA rather than monomeric forms of PSMA.

PSMA-targeting compounds, PSMA antibodies and antigen-binding fragments thereof provided herein typically meet one or more, and in some instances, more than five of the foregoing criteria. In some embodiments, the PSMA-targeting compounds of the present invention meet six or more of the foregoing criteria. In some embodiments, the PSMA-targeting compounds of the present invention meet seven or more of the foregoing criteria. In some embodiments, the PSMA-targeting compounds of the present invention meet eight or more of the foregoing criteria. In some embodiments, the PSMA-targeting compounds of the present invention meet nine or more of the foregoing criteria. In some embodiments, the PSMA-targeting compounds of the present invention meet ten or more of the foregoing criteria. In some embodiments, the PSMA-targeting compounds of the present invention meet all of the foregoing criteria.

Examples of tumors that can be imaged with the PSMA-targeted compounds of the present invention (e.g., PSMA-targeted NIR dye conjugates) provided herein, include any tumor that expresses PSMA such as, e.g., prostate, bladder, pancreas, lung, colon, kidney, melanomas and sarcomas. A tumor that expresses PSMA includes tumors with neovasculature expressing PSMA.

In some embodiments, a PSMA-targeted molecules bind to PSMA and are internalized with PSMA expressed on cells. Thus, a PSMA ligand conjugate comprising a internalized with PSMA expressed on cells. The mechanism by which this internalization occurs is not critical to the practice of the present invention.

In some embodiments, the PSMA targeting compounds bind to a conformational epitope within the extracellular domain of the PSMA molecule. In other embodiments, a PSMA-targeting compound binds to a dimer-specific epitope on PSMA. Generally, the compound that binds to a dimer-specific epitope preferentially binds the PSMA dimer rather than the PSMA monomer. In some embodiments of the present invention, the PSMA-targeting compound preferentially binds to the PSMA dimer. In some embodiments of the present invention, the PSMA-targeting compound has a low affinity for the monomeric PSMA protein.

In some embodiments, the PSMA-targeting compound is a ligand. In some embodiments, the PSMA-targeting compound is 2-[3-(1,3-dicarboxypropyl)ureido] pentanedioic acid (DUPA). In some embodiments, the PSMA-targeting compound is DUPA or derivative of DUPA, ligand, inhibitor, or agonist that binds to PSMA-expressing live cells.

The PSMA-targeting NIR dye of the present invention produces a tumor-to-background signal ratio that is higher than the tumor-to-background signal ratio of the PSMA-targeting compound conjugated to a non-NIR dye or non-targeted NIR dye. In some embodiments, the improvement is 10-fold. In some embodiments, the tumor-to-background signal ratio is at least a 4-fold improvement. In some embodiments, the tumor-to-background ratio is increased by at least 1.5-fold. In some embodiments, the PSMA-targeted NIR dye background signal is half the background signal of the PSMA-targeted compound conjugated to a fluorescent dye reactive to light less than 600 nm in wavelength. In some embodiments of the present invention, methods using the PSMA-targeted NIR dye on live cells produces a background signal less than half the background signal of the PSMA-targeted compound conjugated to a fluorescent dye reactive to light less than 600 nm in wavelength. In some embodiments of the present invention, methods using the PSMA-targeted NIR dye on live cells produces a background signal less than half the background signal of the PSMA-targeted compound conjugated to a fluorescent dye reactive to light less than 500 nm in wavelength. In some embodiments of the present invention, methods using the PSMA-targeted NIR dye on live cells produces a background signal less than one third of the background signal of the PSMA-targeted compound conjugated to a fluorescent dye reactive to light less than 600 nm in wavelength. In some embodiments of the present invention, methods using the PSMA-targeted NIR dye on live cells produces a background signal less than one third of the background signal of the PSMA-targeted compound conjugated to a fluorescent dye reactive to light less than 500 nm in wavelength. In some embodiments of the present invention, methods using the PSMA-targeted NIR dye on live cells produces a background signal less than one fourth the background signal of the PSMA-targeted compound conjugated to a fluorescent dye reactive to light less than 600 nm in wavelength. In some embodiments of the present invention, methods using the PSMA-targeted NIR dye on live cells produces a background signal less than one fourth the background signal of the PSMA-targeted compound conjugated to a fluorescent dye reactive to light less than 500 nm in wavelength. In some embodiments of the present invention, methods using the PSMA-targeted NIR dye on live cells produces a background signal less than one fifth the background signal of the PSMA-targeted compound conjugated to a fluorescent dye reactive to light less than 600 nm in wavelength. In some embodiments of the present invention, methods using the PSMA-targeted NIR dye on live cells produces a background signal less than one fifth the background signal of the PSMA-targeted compound conjugated to a fluorescent dye reactive to light less than 500 nm in wavelength. In some embodiments of the present invention, methods using the PSMA-targeted NIR dye on live cells produces a background signal less than one eighth the background signal of the PSMA-targeted compound conjugated to a fluorescent dye reactive to light less than 600 nm in wavelength. In some embodiments of the present invention, methods using the PSMA-targeted NIR dye on live cells produces a background signal less than one eighth the background signal of the PSMA-targeted compound conjugated to a fluorescent dye reactive to light less than 500 nm in wavelength. In some embodiments of the present invention, methods using the PSMA-targeted NIR dye on live cells produces a background signal less than one tenth the background signal of the PSMA-targeted compound conjugated to a fluorescent dye reactive to light less than 600 nm in wavelength. In some embodiments of the present invention, methods using the PSMA-targeted NIR dye on live cells produces a background signal less than one tenth the background signal of the PSMA-targeted compound conjugated to a fluorescent dye reactive to light less than 500 nm in wavelength.

In some embodiments, the PSMA-targeting compound is a small molecule ligand that binds specifically PSMA. Such small molecule ligands may bind to the enzymatic site of PSMA in its native conformation. Also, such small molecule ligands may possess any one or more of the characteristics for PSMA antibody ligands.

This disclosure also provides methods for synthesizing amino acid linking groups that are conjugated to a PSMA-targeting compound used for the targeted imaging of PSMA-expressing cells, tissues, or tumors. In certain embodiments, this disclosure relates to a compound or a salt derivative thereof, that comprises a PSMA-targeting compound, a linking group, and an NIR dye. In certain embodiments, the linking group can be an amino acid, an isomer, a derivative, or a racemic mixture thereof. In some aspects, the dye is selected from the group consisting of
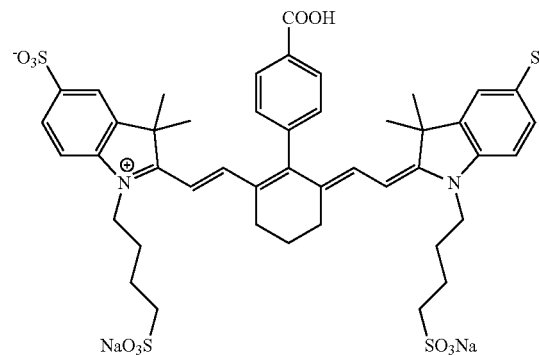
LS288
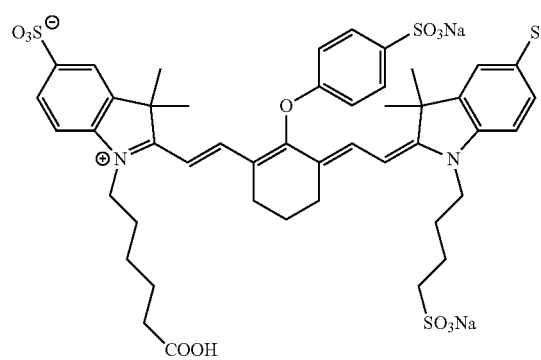
IR800
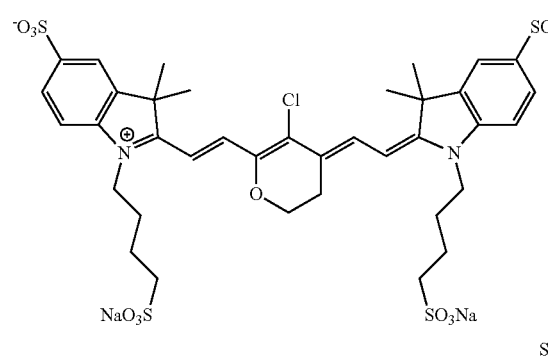
SP054
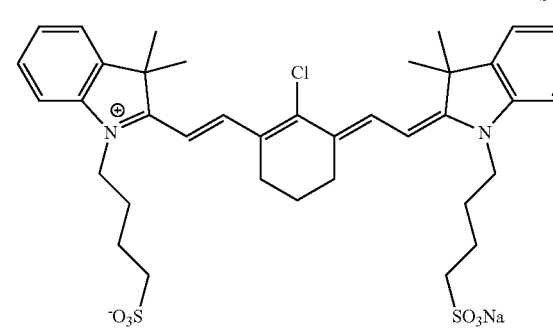
S0121
-continued
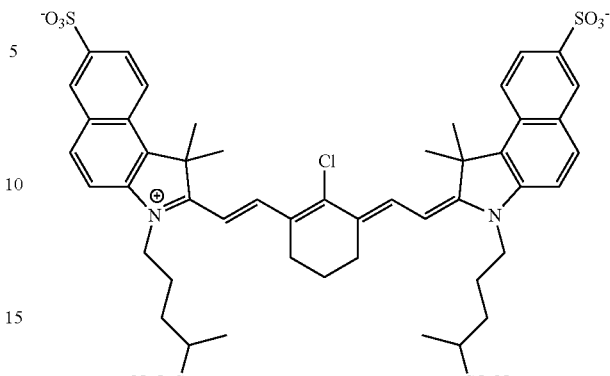
S2076
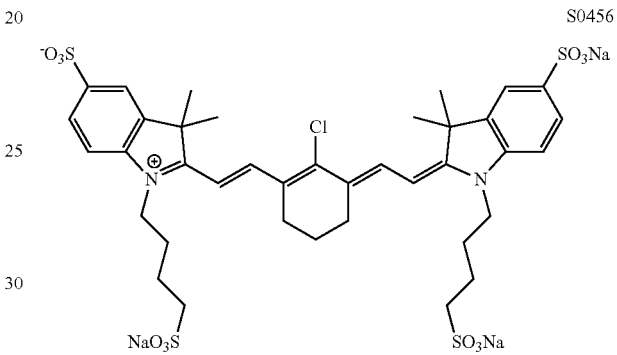
S0456
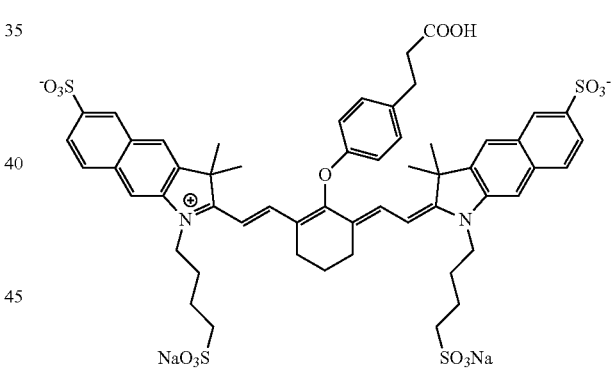
KODAK
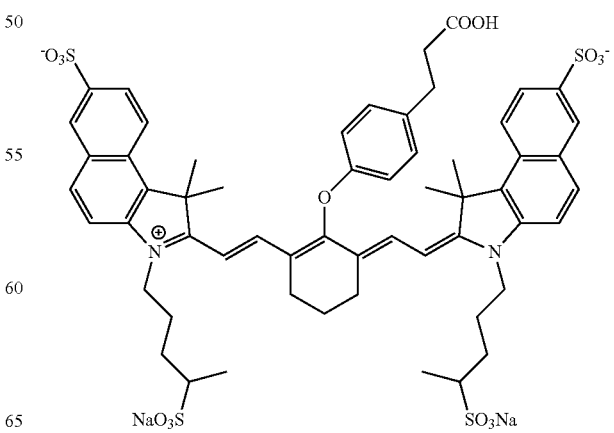
IRD28 and/or the dyes selected from group consisting of.
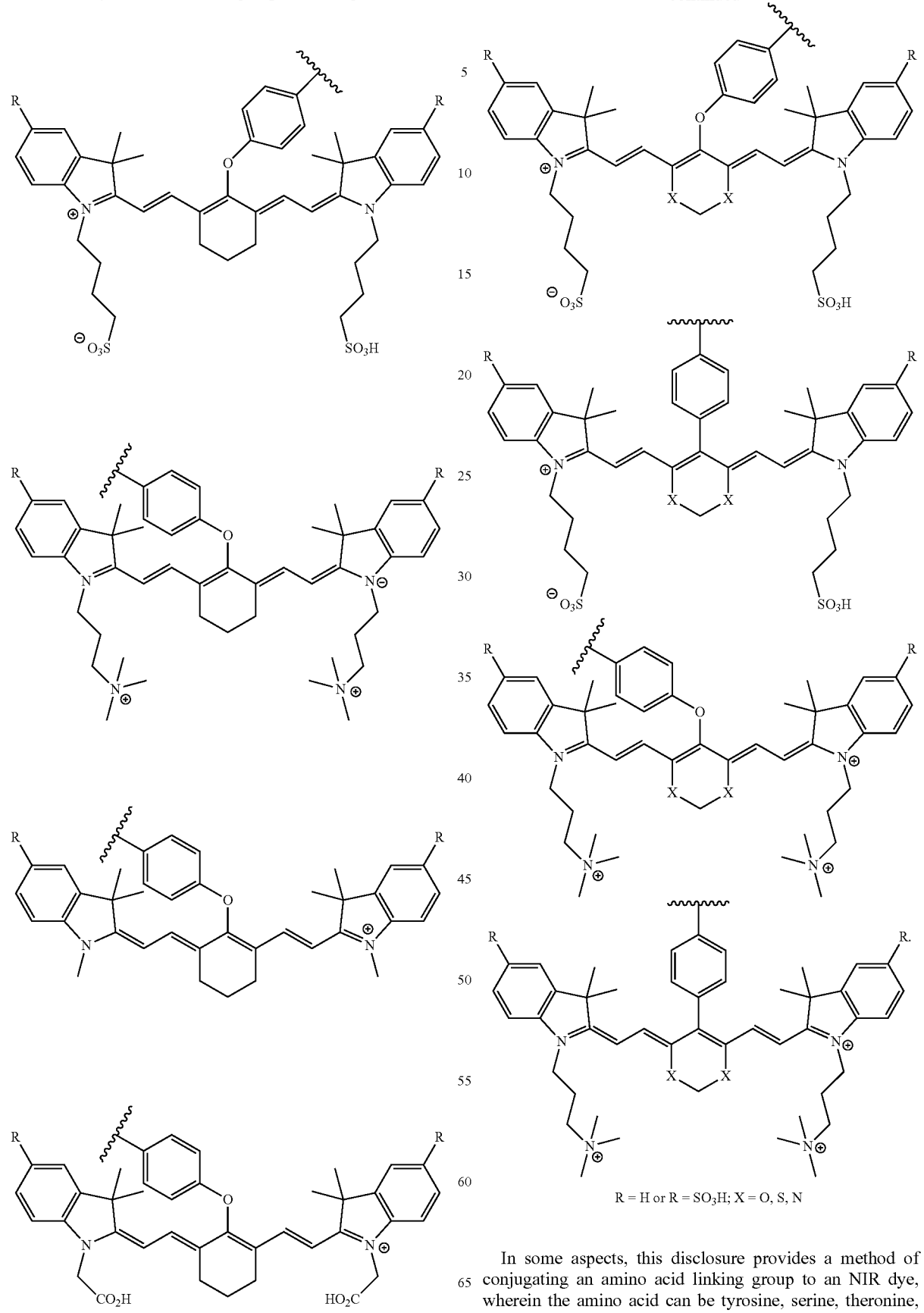
R = H or R = SO₃H; X = O, S, N
In some aspects, this disclosure provides a method of conjugating an amino acid linking group to an NIR dye, wherein the amino acid can be tyrosine, serine, threonine, lysine, arginine, asparagine, glutamine, cysteine, selenocysteine, isomers, and the derivatives thereof. In certain embodiments, the amino acid, isomers, or the derivatives thereof, contain an —OH, —NH$_2$, or —SH functional group that upon addition of the fluorescent dye in slight molar excess produces the conjugation of fluorescent group with the amino acid, isomer, or the derivatives thereof. In other embodiments, the amino acid, isomers, or the derivatives thereof, contains an —OH functional group that upon synthesis generates an ether bond with the dye that increases the brightness and detection of the compound. In some embodiments, this disclosure relates to the conjugation of the amino acid linking group with the NIR dye, wherein the amino acid, isomers, or the derivatives thereof, contains an —SH, —SeH, —PoH, or —TeH functional group that upon synthesis generates a C—S, C—Se, C—Po, or C—Te bond with the dye. In some aspects, this disclosure relates to the conjugation of the amino acid linking group to a dye that has an absorption and emission maxima between about 500 nm and about 900 nm. In other aspects, the amino acid linking group is conjugated to a fluorescent dye that has an absorption and emission maxima between about 600 nm and about 800 nm.

In additional embodiments, this disclosure provides a method for conjugating the amino acid linking group to a PSMA ligand, wherein the amino acid linking group is tyrosine, serine, threonine, lysine, arginine, asparagine, glutamine, cysteine, selenocysteine, isomers or the derivatives thereof, and is conjugated to folate through a dipeptide bond. In additional aspects, this disclosure provides a method of conjugating the linking group with a folate ligand, wherein the linking group is tyrosine, serine, threonine, lysine, arginine, asparagine, glutamine, cysteine, selenocysteine, isomers, or the derivatives thereof. In other embodiments, this disclosure relates to a method of conjugating a pteroyl ligand to an amino acid linking group, wherein the linking group is tyrosine, serine, threonine, lysine, arginine, asparagine, glutamine, cysteine, selenocysteine, isomers or the derivatives thereof. In certain aspects, the carboxylic acid of the linking group is bound to the alpha carbon of any amino acid, hence increasing the specificity of the compound for targeted receptors. In some embodiments, the charge of the linker contributes specificity to the compound, wherein the observed binding affinity of the compound to targeted receptors is at least 15 nM.

In other embodiments, this disclosure relates to the use of a compound designated, DUPA-EAOA-Tyr-S0456, wherein EAOA is eight aminooctonoic acid, for image guided surgery, tumor imaging, prostate imaging, PSMA-expressing tissue imaging, PSMA-expressing tumor imaging, infection diseases, or forensic applications. In other aspects, the compound is a DUPA-EAOA-Tyr-S0456 derivative selected from the group consisting of DUPA-EAOA-(D)Tyr-S0456, DUPA-EAOA-homoTyr-S0456, DUPA-EAOA-beta-homo-Tyr-S0456, DU PA-EAOA-(N Me)-Tyr-S0456, DU PA-EAOA-Tyr(OMe)-S0456, DUPA-EAOA-Tyr(OBn)-S0456, DUPA-EAOA-NHNH-Tyr-OAc-S0456, salts, and derivatives thereof.

In some embodiments, the PSMA-targeted compound of the present invention is a small molecule ligand of PSMA.

Some embodiments include a method for synthesizing a compound of the formula:

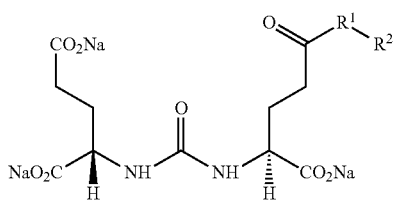

or a racemic mixture thereof, wherein:

R$^1$ is selected from the group consisting of:

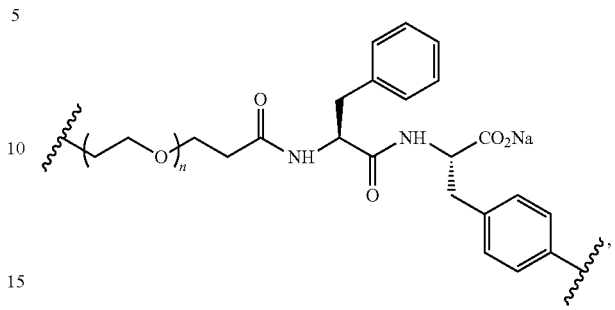

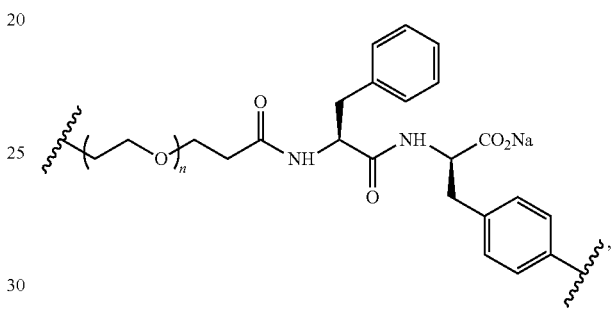

and a racemic mixture thereof: and

R$^2$ is represented by the formula:

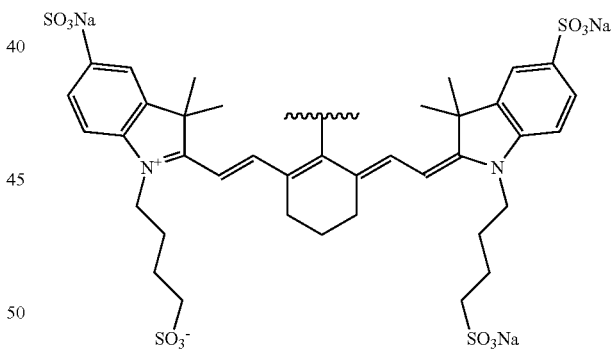

comprising the steps of:

(a) reacting a compound of formula I:

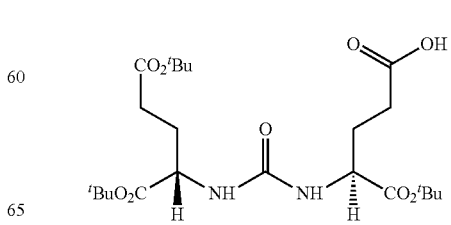

I with a compound of formula:
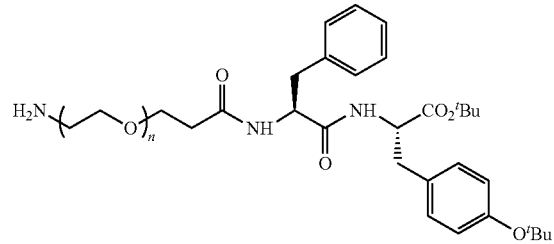
or
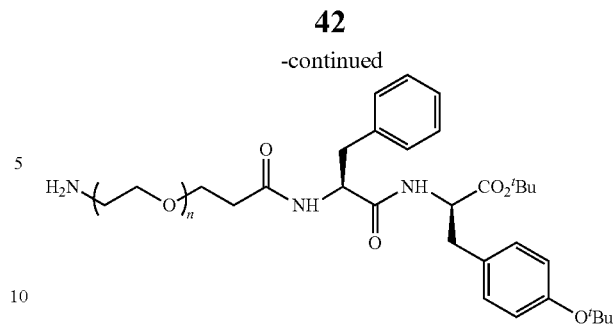
in the presence of a polar organic solvent, 1-[Bis(dimethylamino)methylene]-1H-1,2,3-triazolo[4,5-b]pyridinium 3-oxid hexafluorophosphate and N,N-Diisopropylethylamine under argon to provide a compound of the formula:
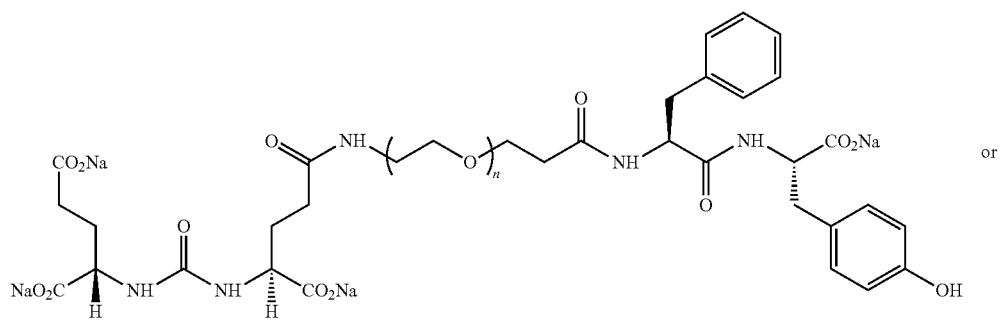
or
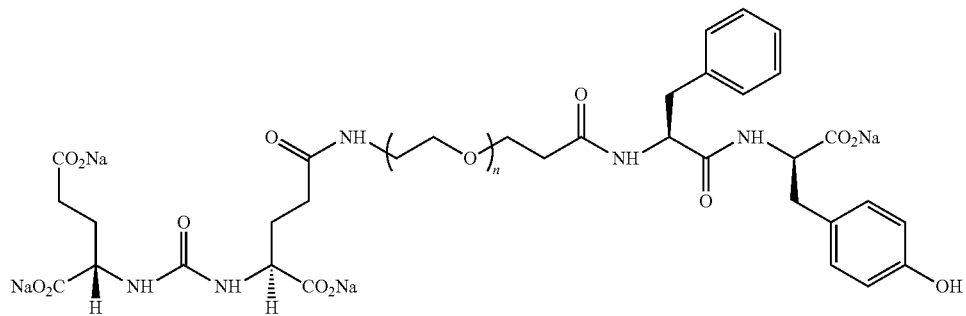
or a racemic mixture thereof;
(b) reacting the compound of formula:
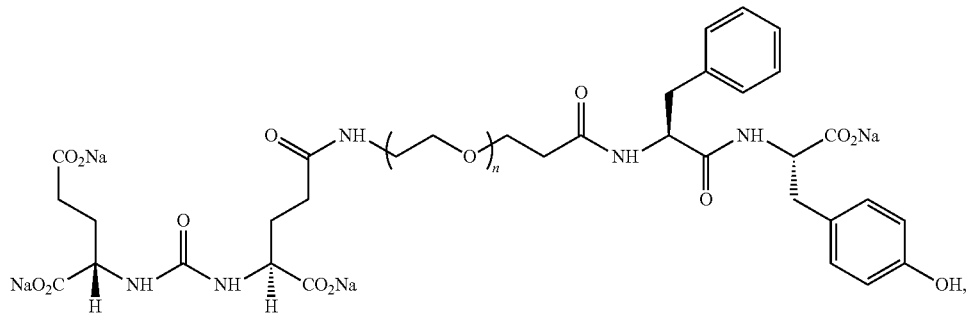

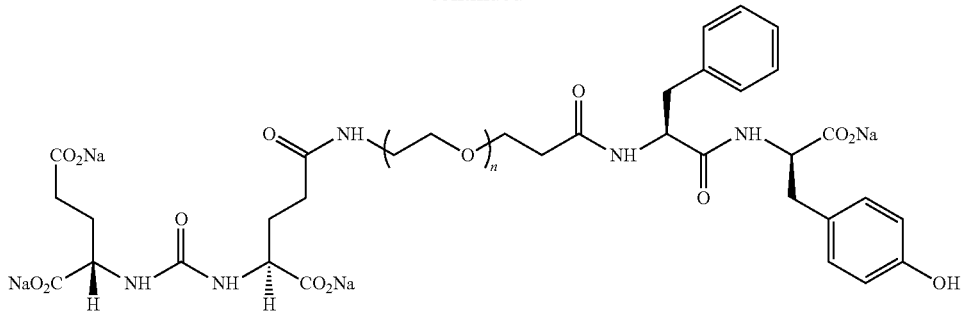
or a racemic mixture thereof,
with sodium carbonate and a dye compound of the formula:
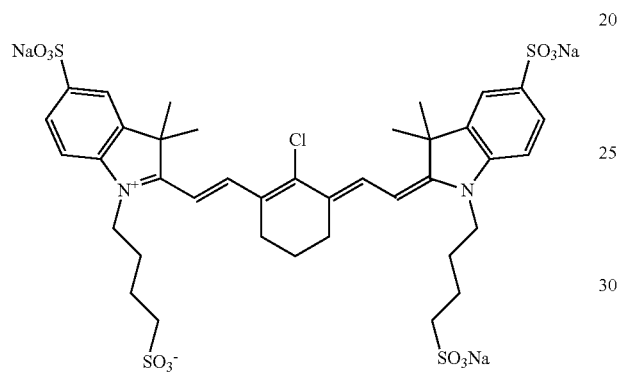
(c) isolating the compound of the formula:
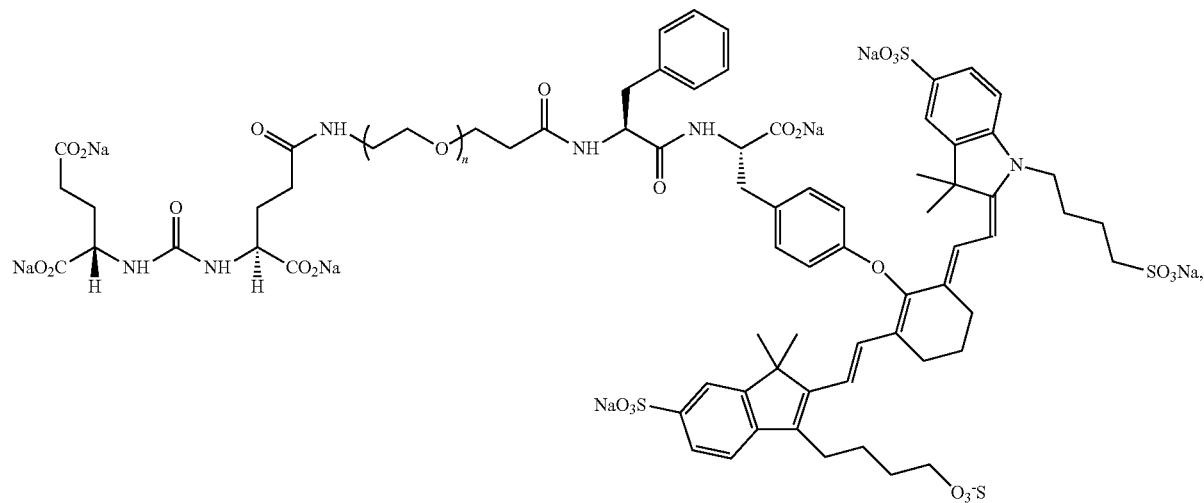
wherein n is 0, 1, 2, 3, or 4.
In some embodiments, the polar organic solvent is selected from the group consisting of dimethyl sulfoxide, dimethylformamide, and water.
Another embodiment includes a method for synthesizing a compound of the formula:

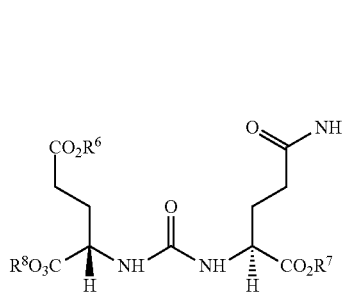
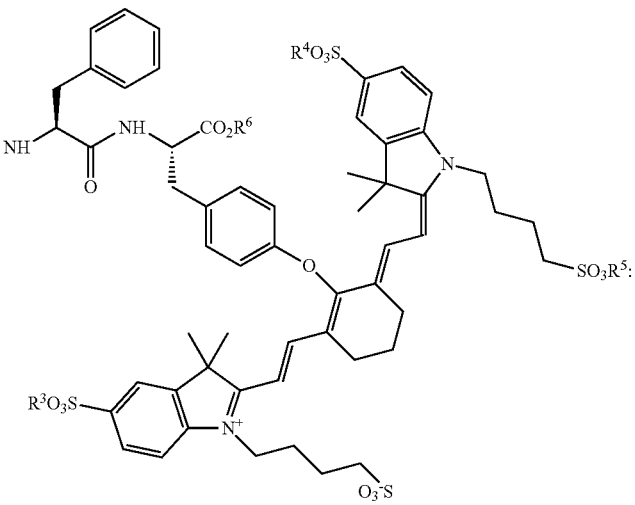
comprising the steps of:
(a) reacting a compound of formula I:
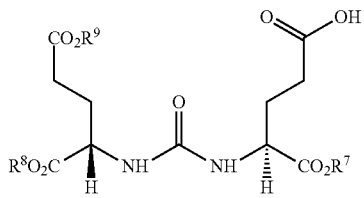
I
with a compound of formula:
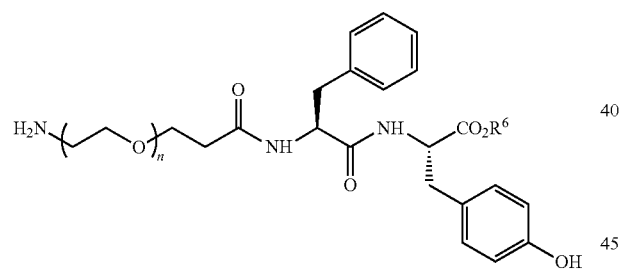
in the presence of a polar organic solvent, 1-[Bis(dimethylamino)methylene]-1H-1,2,3-triazolo[4,5-b]pyridinium 3-oxid hexafluorophosphate and N,N-Diisopropylethylamine under argon to provide a compound of the formula:
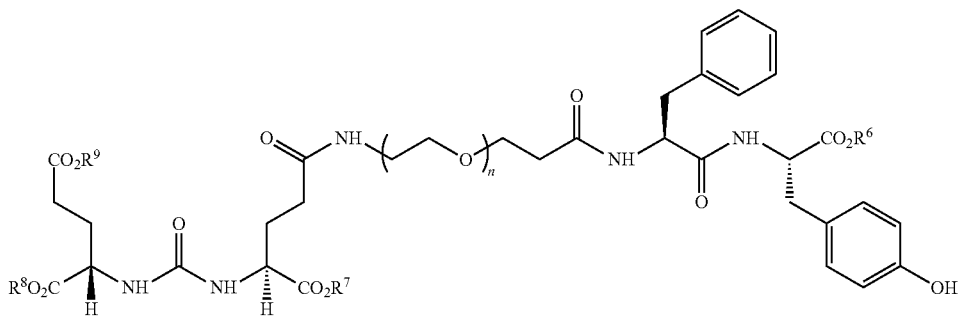

(b) reacting the compound of formula:

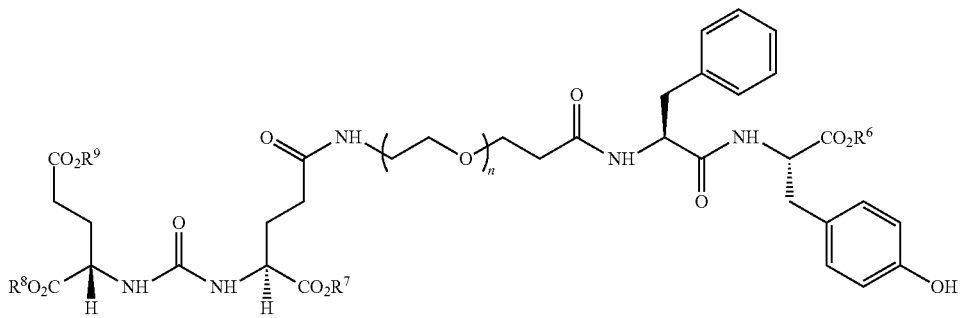

with sodium carbonate and a dye compound of the formula:

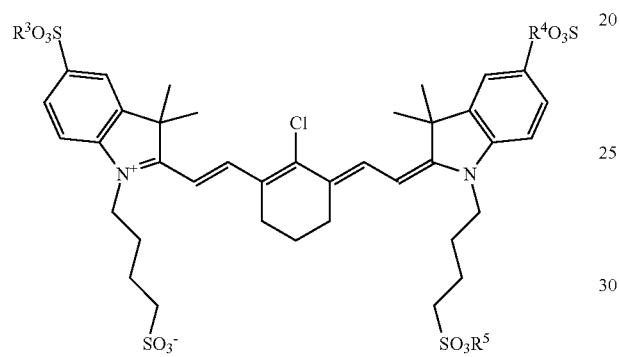

(c) isolating the compound of the formula:

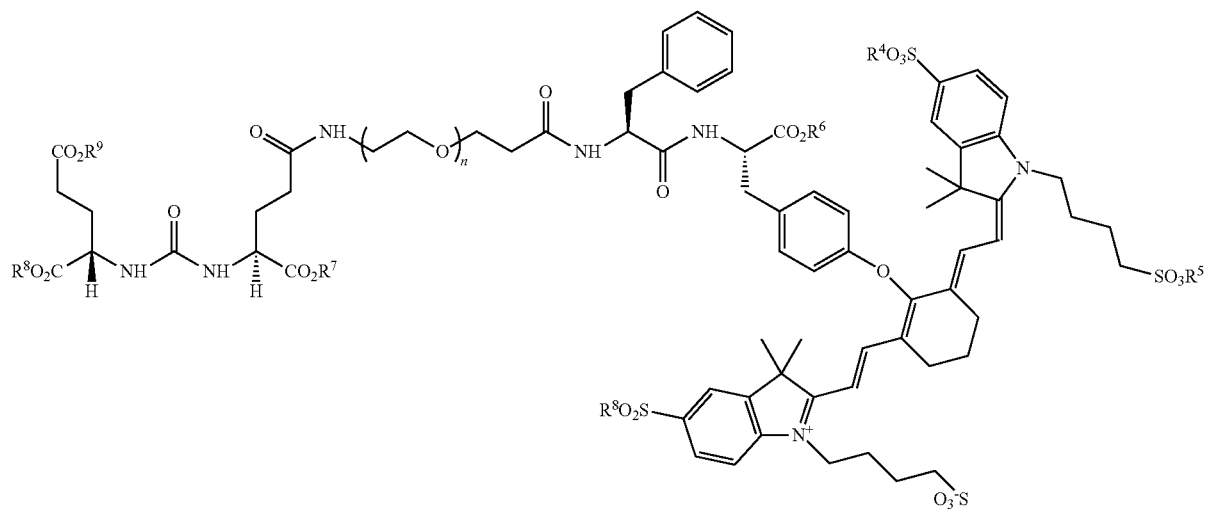

wherein n is 0, 1, 2, 3, or 4, and
wherein:
$R^3$, $R^4$, $R^5$, $R^6$, $R^7$, $R^8$, and $R^9$ are independently selected from the group consisting of $H^+$, $Na^+$, $K^+$, and $NH_4^+$.

Yet another embodiment includes a method for synthesizing an isotopic form of a compound of the formula:

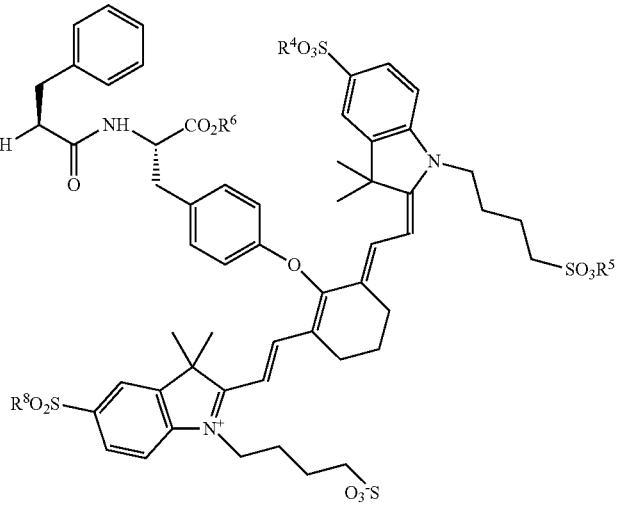

wherein said isotopic form comprises one or more carbon and/or hydrogen isotopes selected from the group consisting of $H^2$, $H^3$, $C^{13}$ and $C^{14}$, and further wherein $R^3$, $R^4$, $R^5$, $R^6$, $R^7$, $R^8$, and $R^9$ are independently selected from the group consisting of $H^+$, $Na^+$, $K^+$, and $NH_4^+$; comprising the steps of:

(a) reacting an isotopic form of a compound of formula:

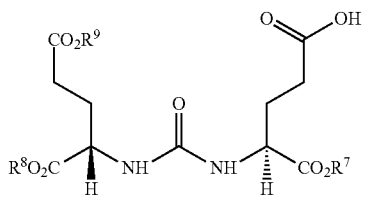

wherein said isotopic form comprises one or more carbon and/or hydrogen isotopes selected from the group consisting of $H^2$, $H^3$, $C^{13}$ and $C^{14}$, with an isotopic form of a compound of formula:

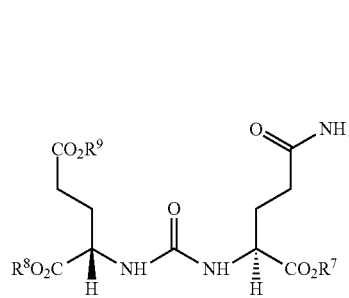

wherein said isotopic form comprises one or more carbon and/or hydrogen isotopes selected from the group consisting of $H^2$, $H^3$, $C^{13}$ and $C^{14}$, in the presence of a polar organic solvent, 1-[Bis(dimethylamino)methylene]-1H-1,2,3-triazolo[4,5-b]pyridinium 3-oxid hexafluorophosphate and N,N-Diisopropylethylamine under argon to provide an isotopic form of a compound of the formula:

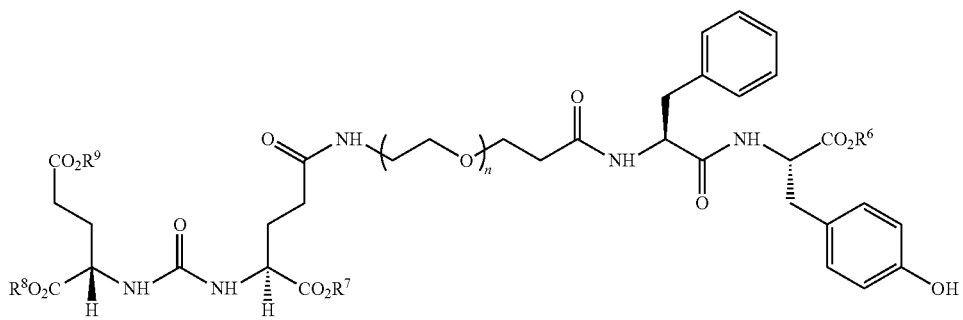

wherein said isotopic form comprises one or more carbon and/or hydrogen isotopes selected from the group consisting of $H^2$, $H^3$, $C^{13}$ and $C^{14}$, (b) reacting the isotopic form of the compound of formula:

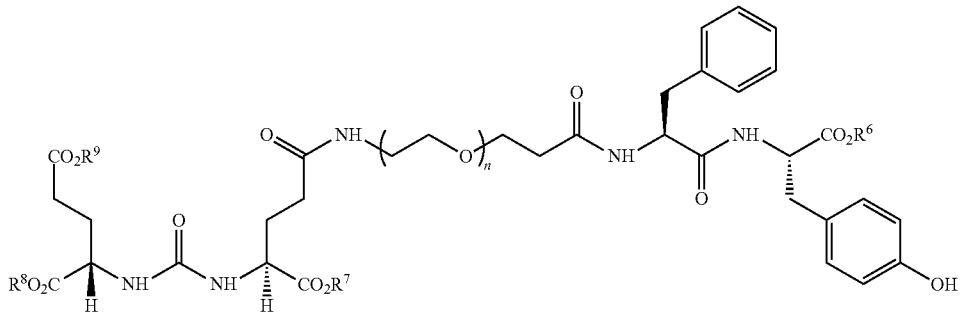

with sodium carbonate and an isotopic form of a dye compound of the formula:

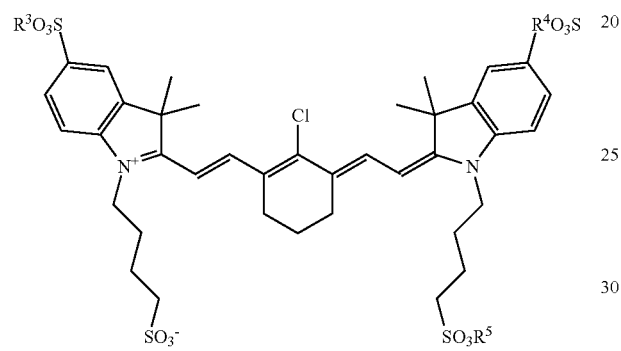

wherein said isotopic form comprises one or more carbon and/or hydrogen isotopes selected from the group consisting of $H^2$, $H^3$, $C^{13}$ and $C^{14}$, (c) isolating the isotopic form of the compound of the formula:

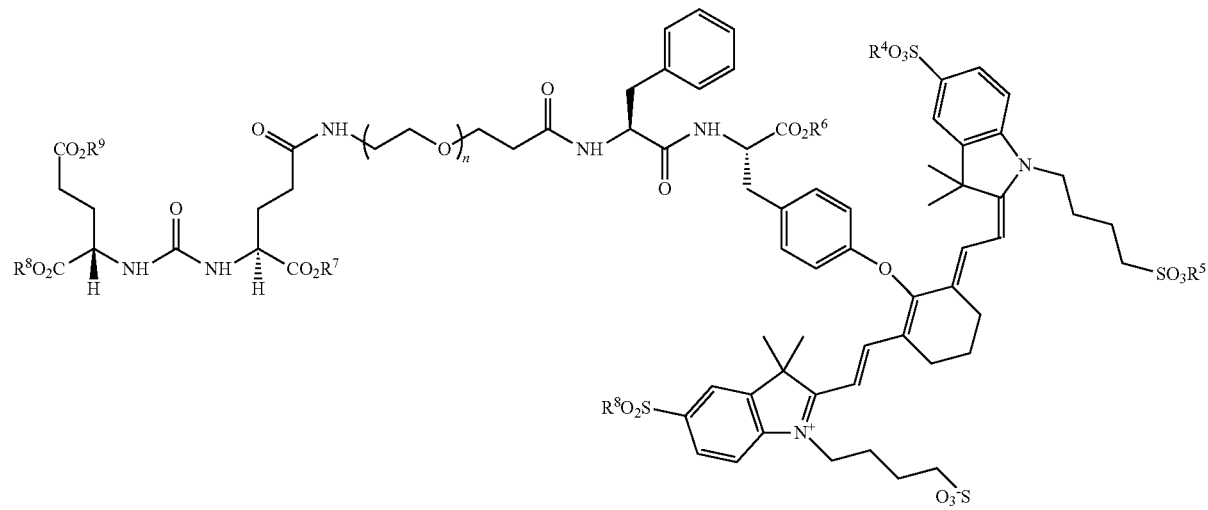

wherein n is 0, 1, 2, 3, or 4, and
wherein:
$R^3$, $R^4$, $R^5$, $R^6$, $R^7$, $R^8$, and $R^9$ are independently selected from the group consisting of $H^+$, $Na^+$, $K^+$, and $NH_4^+$.

PSMA-Targeted NIR Dye Conjugates and Their Synthesis
The following schemes show the synthesis of PSMA-targeted NIR dye conjugates of the present invention.
Scheme 1:
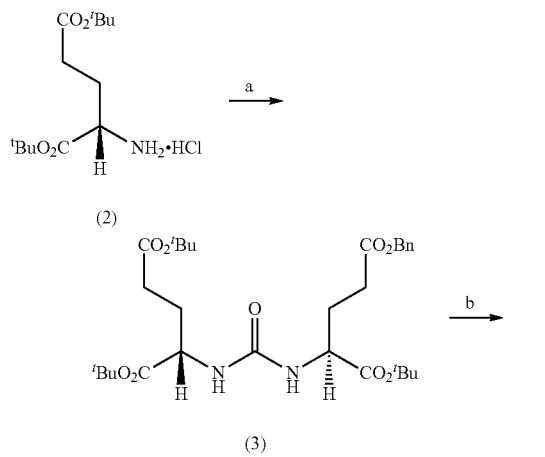
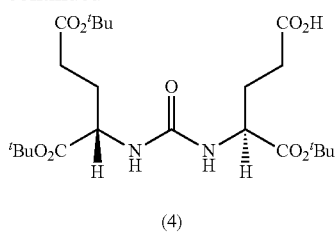
Reagents and conditions: (a) (i) triphosgene, TEA/DCM, -78° C.; (ii) H—L-Glu(OBn)—O′Bu•HCl; (b) H₂; Pd—C/DCM
(a) Solid Phase Synthesis
Scheme 2:
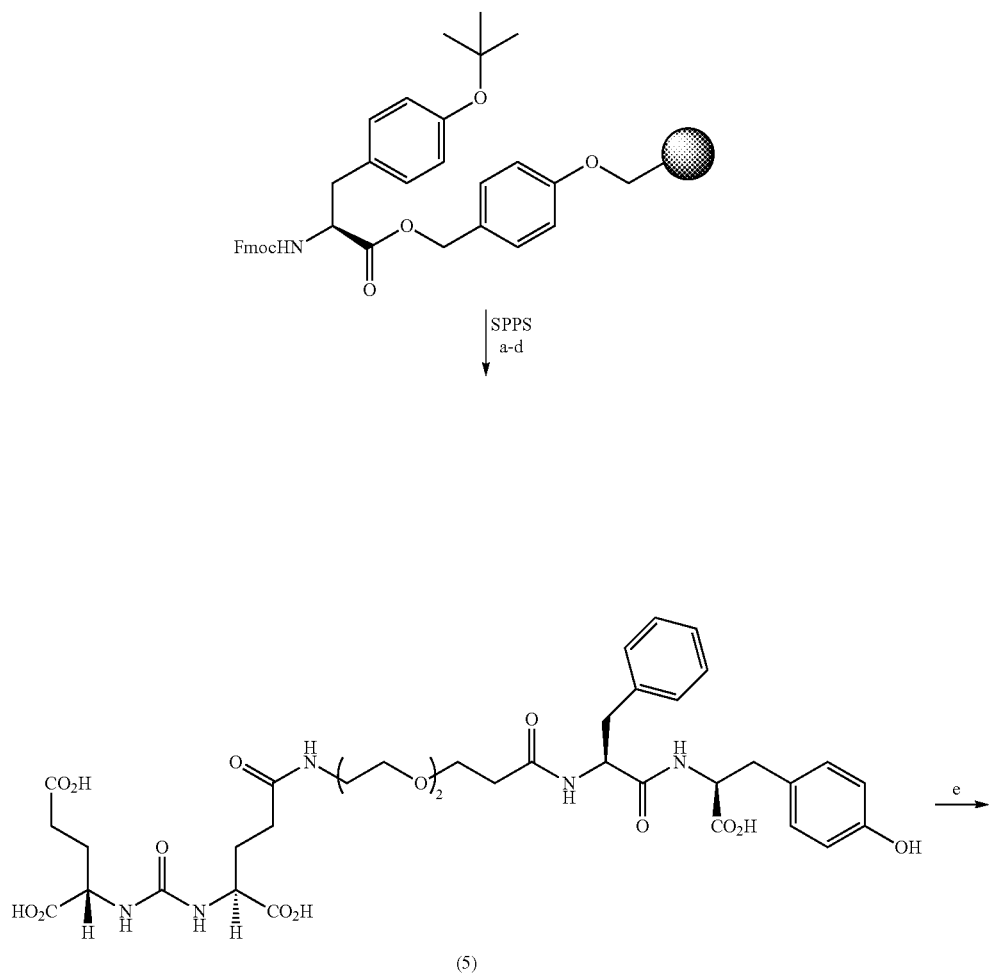

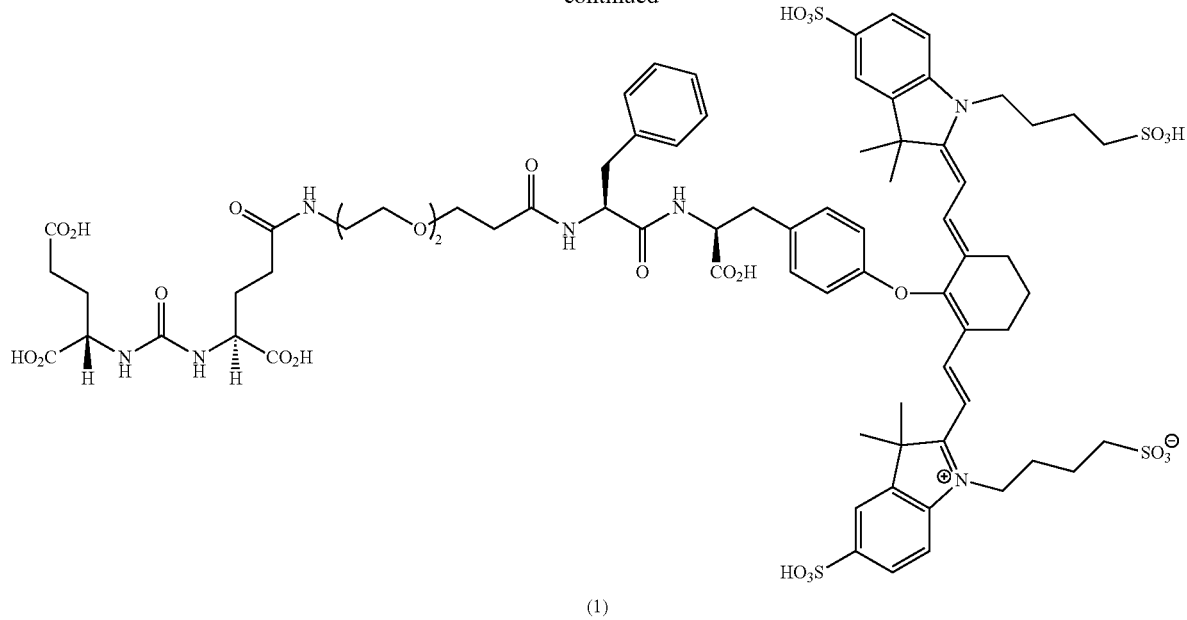
(1)
Reagents and conditions: (a) (i) 20% piperidine/DMF, r.t., 10 min; (ii) Fmoc-Phe-OH, HATU, DMF/DIPEA, 2 h; (b) (i) 20% piperidine/DMF, r.t., 10 min; (ii) Fmoc-Eightaminooctanoic acid-OH, HATU, DMF/DIPEA, 2 h; (c) (i) 20% piperidine/DMF, r.t., 10 min; (ii) 4, HATU, DMF/DIPEA, 2 h; d) TFA:H₂O:TIPS (95:2.5:2.5), 1 h; (e) (i) H₂O, aq. NaOH/pH = 9.5, r.t.; (ii) S0456, H₂O, 100° C., 15 min.
(b) Solution Phase Synthesis
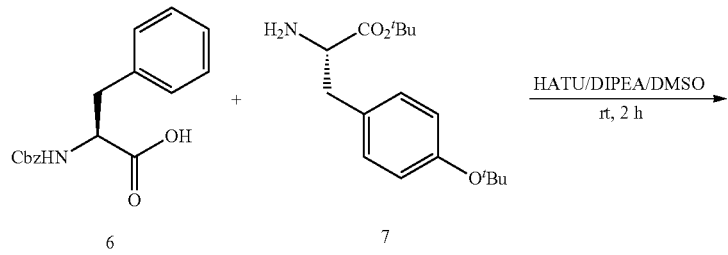
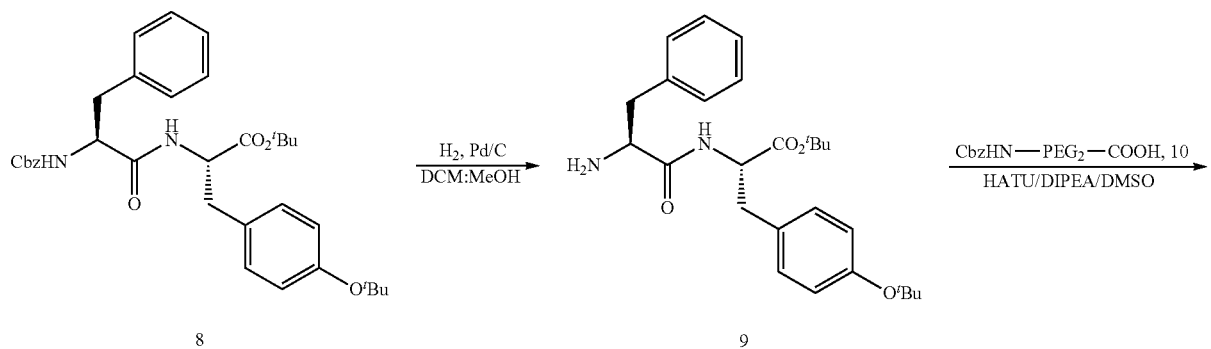

-continued
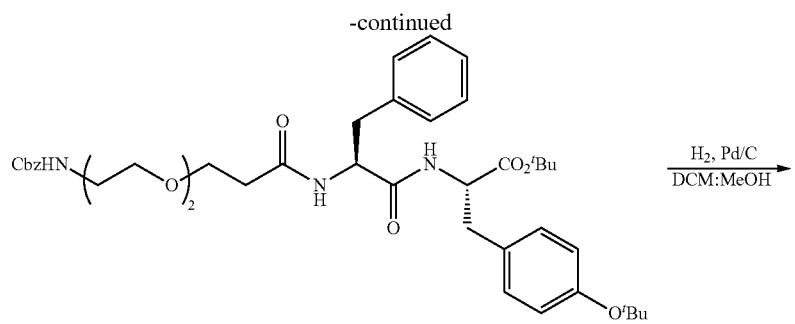
11
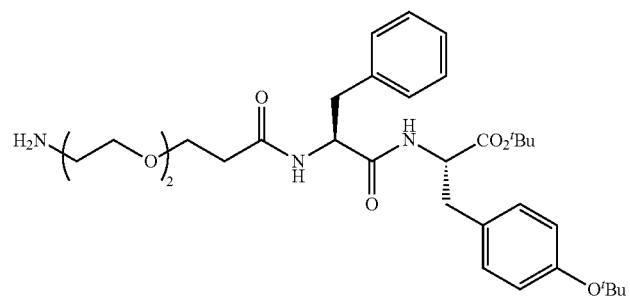
12
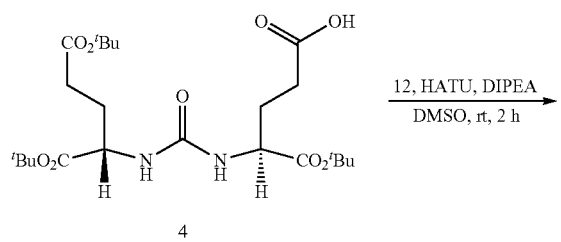
4
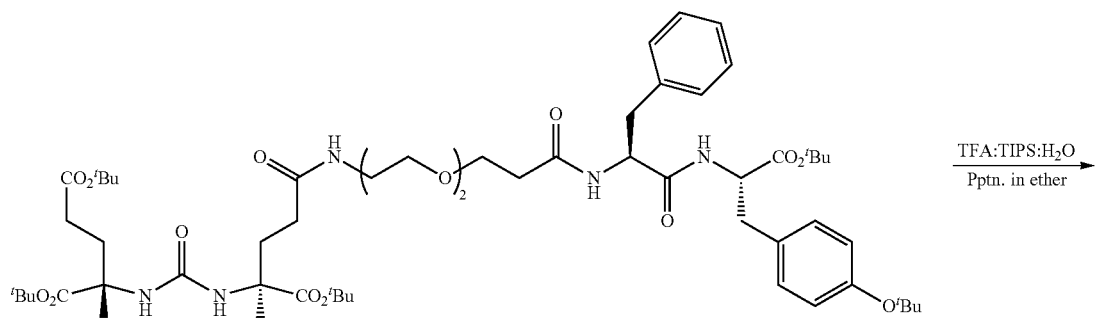
13
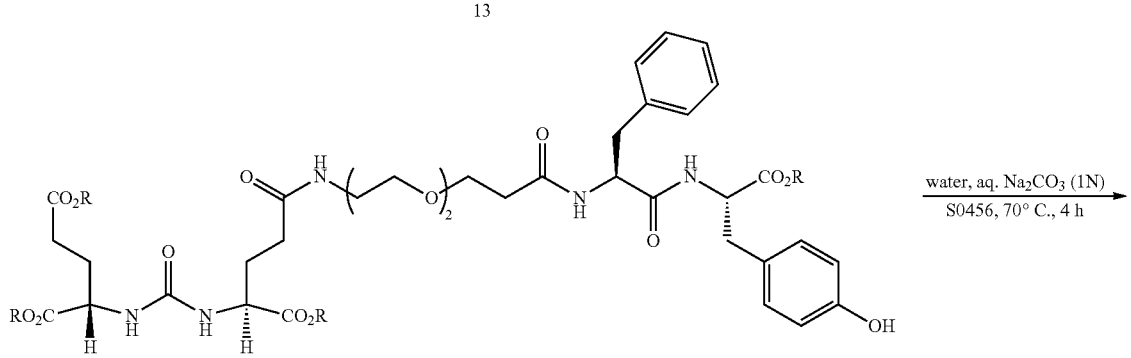
R = H, 5
R = Na, 14
HPLC purification
Na-phosphate buffer -continued

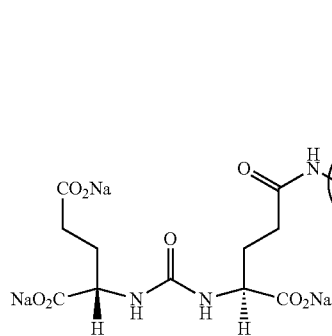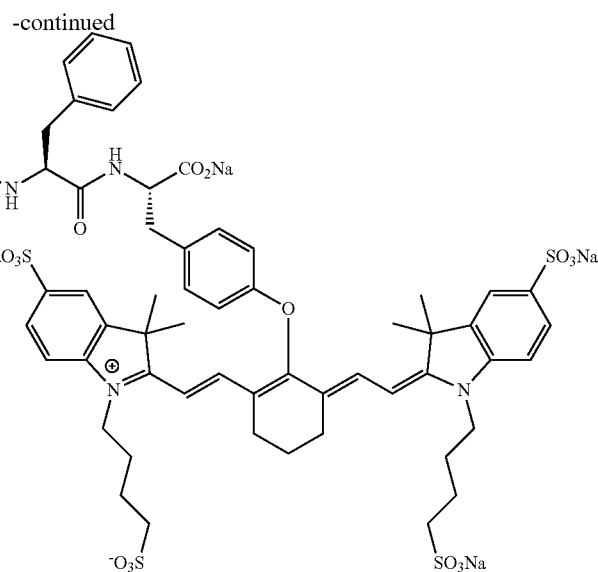

(1)
OTL78

EXAMPLES

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

General Methods: 22Rv1 cells (a human prostate cancer cells) were grown as a monolayer using RPMI medium (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic male nude (nu/nu) mice (7 weeks old, 18-20 g) were purchased from Envigo (Indianapolis, Ind.) and maintained on normal rodent diet (Teklad, WI). Animals were housed 5/cage in a barrier, pathogen-free cloaked rack. Autoclaved tap water and food were given as needed. The animals were housed in a sterile environment on a standard 12 hour light-dark cycle for the duration of the study. Mice were identified individually by ear punch. All animal procedures were approved by Purdue Animal Care and Use Committee. Animal care and studies were performed according to national and international guidelines for the humane treatment of animals.

In vitro binding and specificity: 22Rv1 cells were seeded into a T75 flask and allowed to form a monolayer over 24 h. After trypsin digestion, release cells were transferred into centrifuge tubes ($1 \times 10^6$ cells/tube) and centrifuged. The medium was replaced with fresh medium containing increasing concentration of requisite 1: OTL78 dye compound in the presence or absence of 100-fold excess the ligand, a high affinity PSMA inhibitor, and incubated for 1 h at 37° C. After rinsing with fresh medium ($2 \times 1.0$ mL) and PBS ($1 \times 1.0$ mL), cells were resuspended in PBS (1.0 mL) and cell bound fluorescence was analyzed (100,000 cells/sample) using a fluorometer (Cary, Agilent). The relative binding affinities were calculated using a plot of % cell bound fluorescence versus the log concentration of the test article using GraphPad Prism 4.

Whole-body imaging: seven-weeks-old male nu/nu mice were inoculated subcutaneously with 22Rv1 cells ($5.0 \times 10^6$/mouse in 50% high concentrated matrigel in RPMI medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 $mm^3$ in volume, animals (5 mice/group) were intravenously injected with 10 nmol of requisite 1: OTL78 in phosphate buffered saline (100 μL). For whole body imaging and biodistribution studies, animals were euthanized by $CO_2$ asphyxiation 2 hours after administration of the compound of interest.

Whole-body imaging (intact tumor) experiments were then performed using a Caliper IVIS Lumina II Imaging Station with Living Image 4.0 software (PerkinElmer Inc, MA).

Settings for imaging:—lamp level: medium; excitation: 745 nm; emission: ICG(830 nm); epi illumination; binning: 4 (M), FOV=12.5; f-stop=2; acquisition time=1 s. For time dependent studies, animals were imaged under anesthesia using isoflurane. Whole body imaging (intact tumor) experiments was then performed using a Caliper IVIS Lumina II Imaging Station with Living Image 4.0 software (PerkinElmer Inc, MA).

Tissue bio-distribution: Following Whole-body imaging, animals were dissected and selected tissues (heart, lung, liver, spleen, kidneys, stomach, small intestine, large intestine, muscle, skin, and tumor) were analyzed for fluorescence activity using IVIS imager as before. Settings for imaging:—lamp level: medium; excitation: 745 nm; emission: ICG; epi illumination; binning: 4 (M), FOV=12.5; f-stop=2; acquisition time=1 s.

Example (1)

Figure 2:
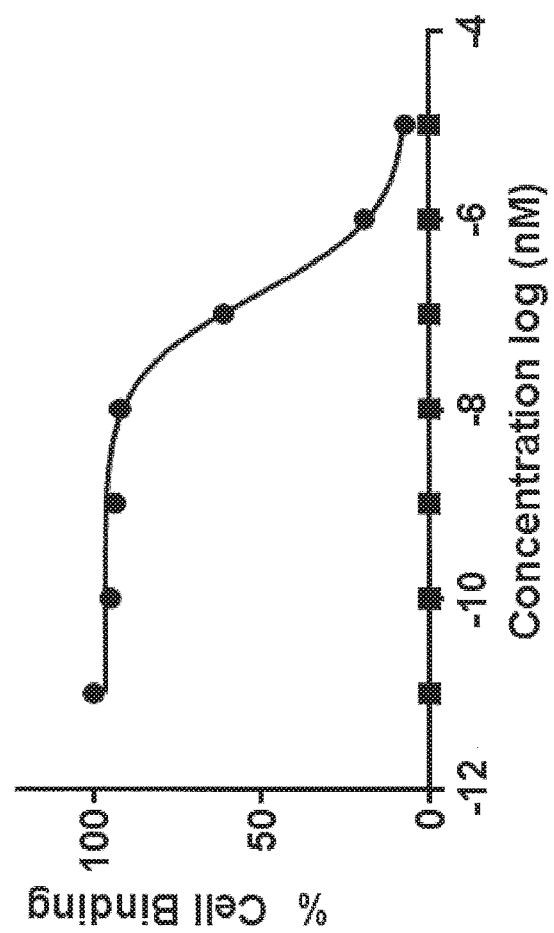
FIG. 2 illustrates the relative binding affinity of 1: OTL78 with respect to DUPA-FITC (14). PSMA-positive 22Rv1 human prostate cancer cells were incubated for 1 h at 37° C. in the presence of 100 nM DUPA-FITC with increasing concentrations of 1. Media was then removed, washed with fresh media three times, and replaced with PBS. Cell bound fluorescence was assayed as using flow cytometry.
Figure 3:
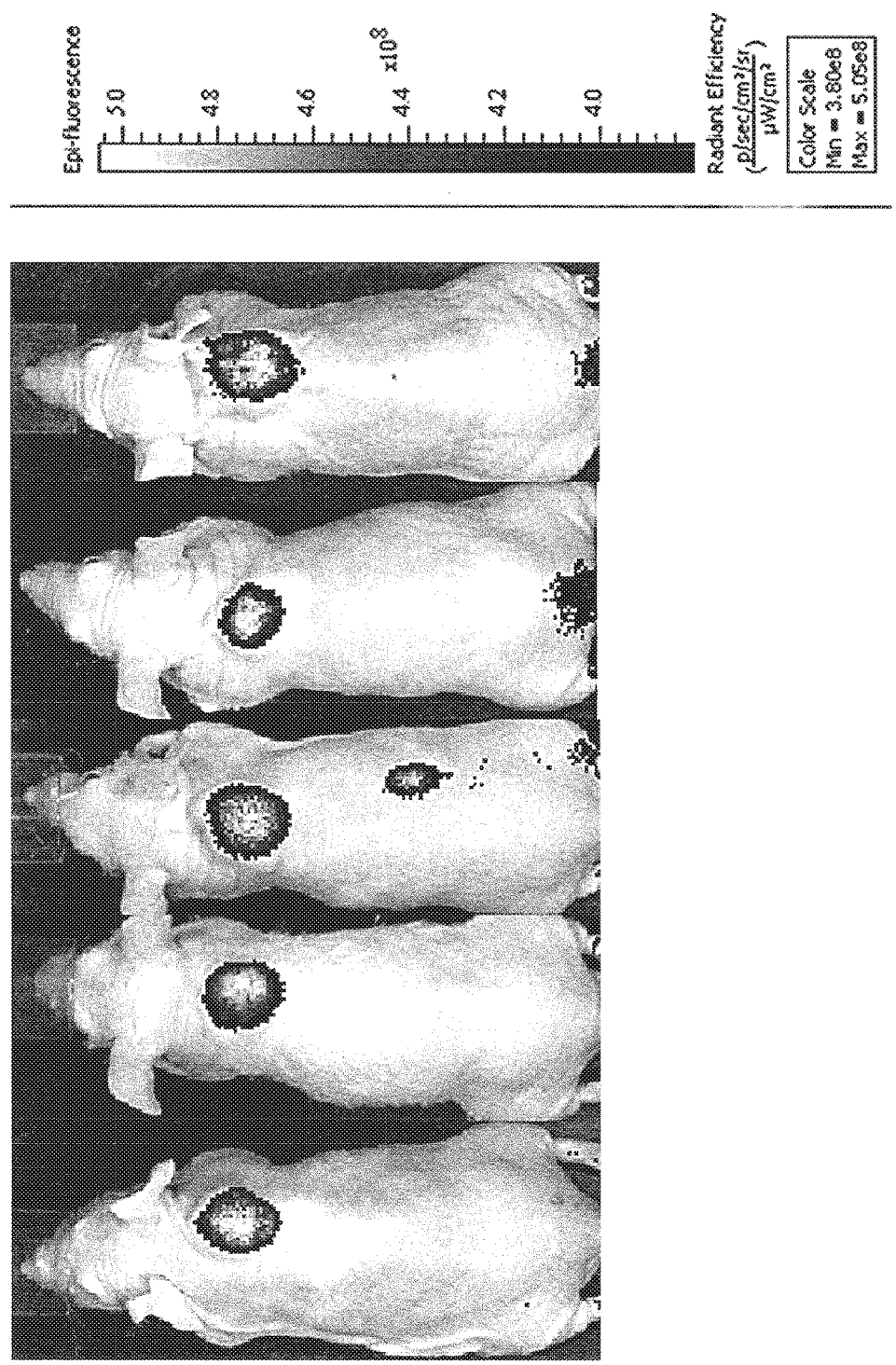
FIG. 3 shows the overlay of whole body fluorescence image over white light images after adjusting the threshold at 2 h time point after injecting with 1: OTL78 to mice bearing prostate tumor xenografts. 22Rv1 human prostate tumor xenograft bearing mouse was injected with 10 nmol of 1: OTL78 and imaged with IVIS imager (ex=745 nm, em=ICG, exposure time=1 s) at 2 h post injection
Figure 4:
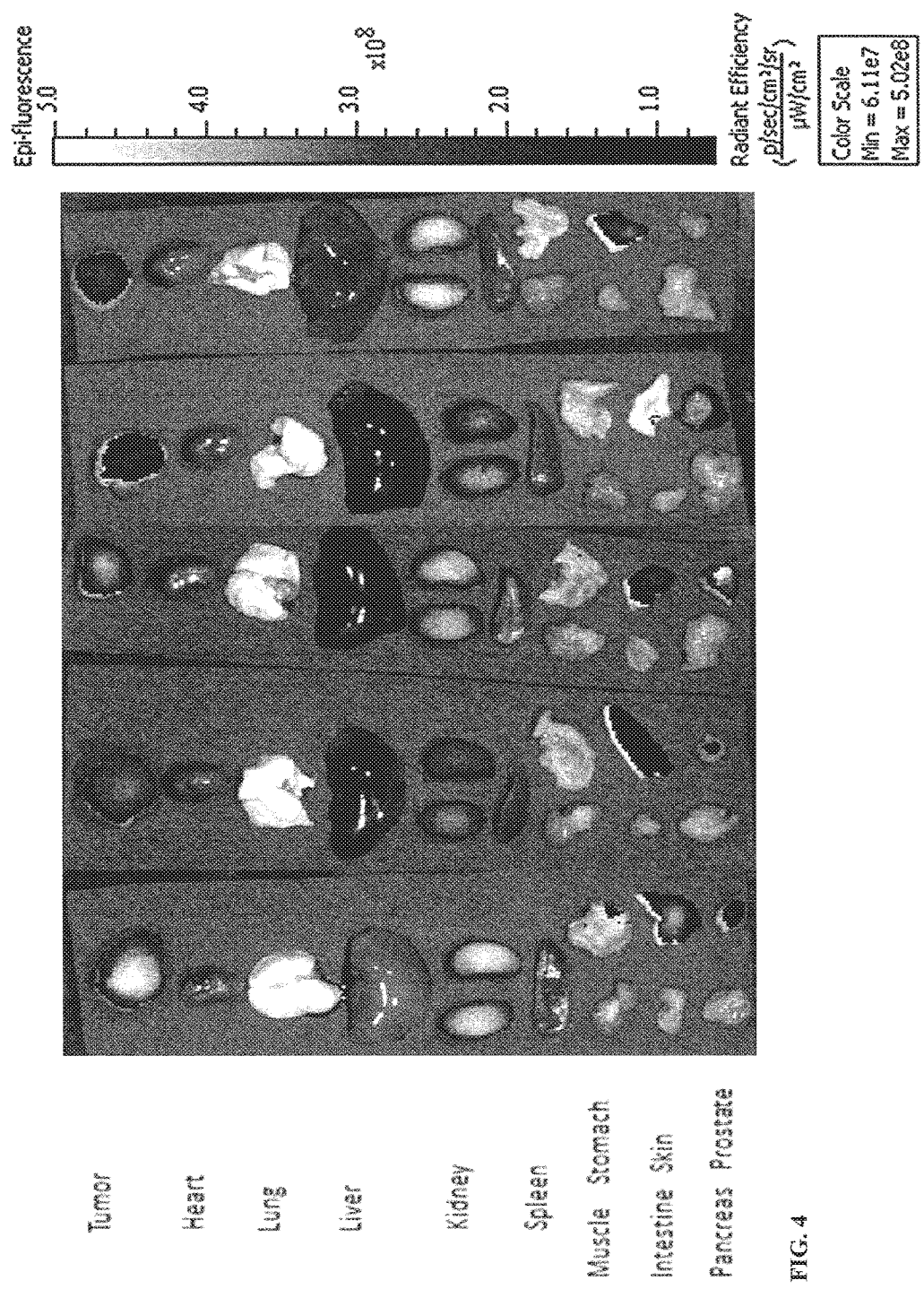
FIG. 4 depicts the ex vivo tissue biodistribution of 1: OTL78 in mice from the FIG. 3 dissecting after whole-body imaging.
Figure 5A:
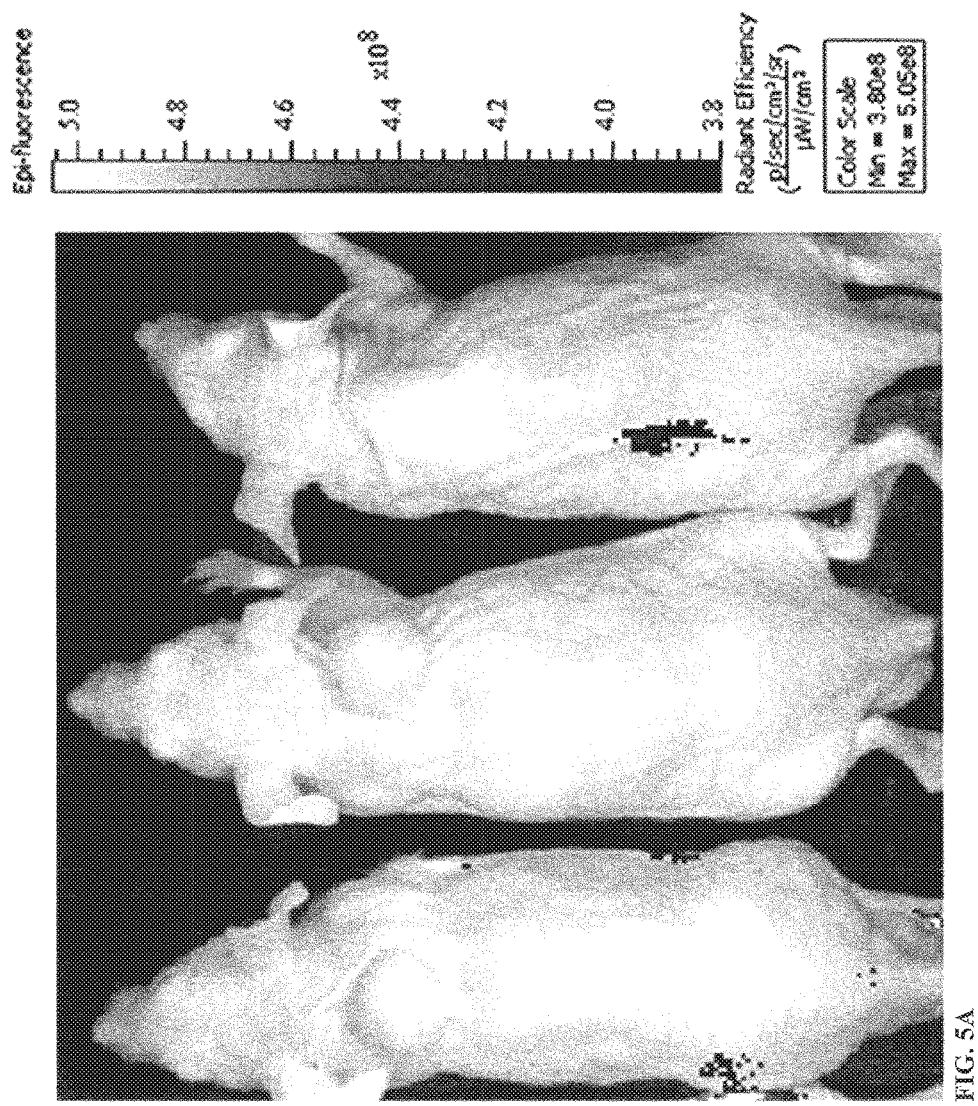
FIG. 5A demonstrates the in vivo specificity of 1: OTL78 using whole-body imaging with nude mice bearing PC3 tumors (PSMA-negative).
Figure 5B:
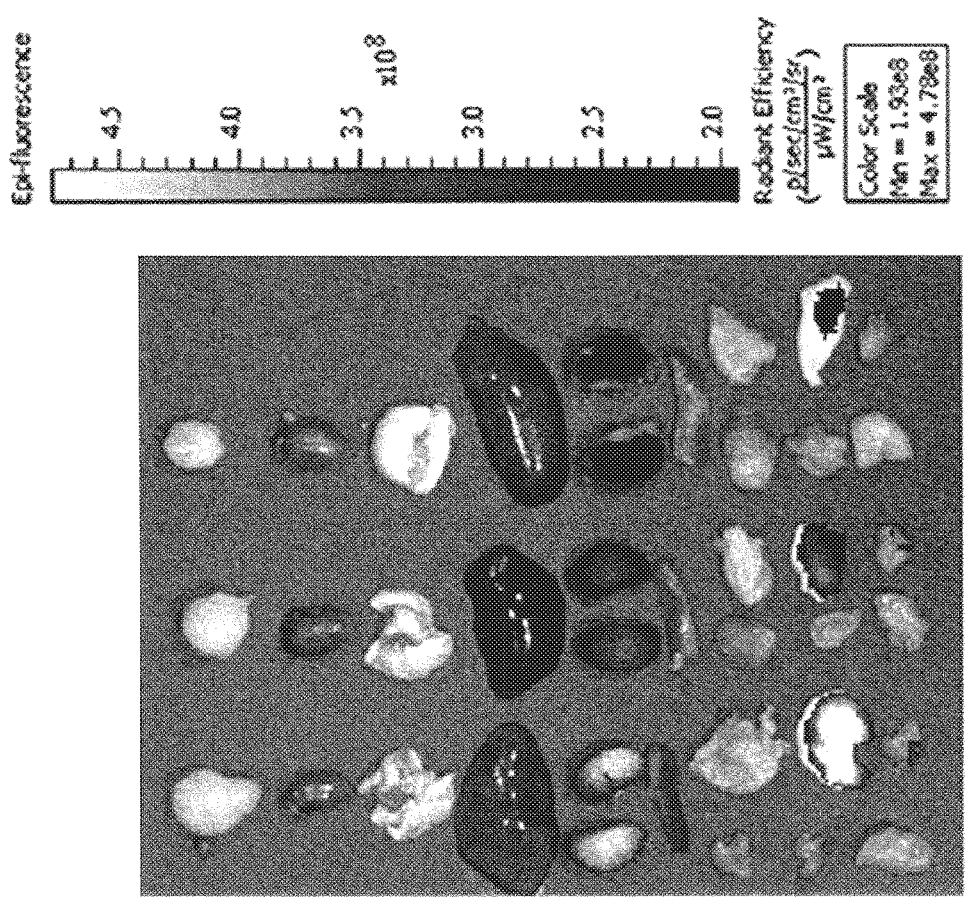
FIG. 5B demonstrates the in vivo specificity of 1: OTL78 using ex vivo tissue biodistribution of the mice in FIG. 5A.
Figure 6A:
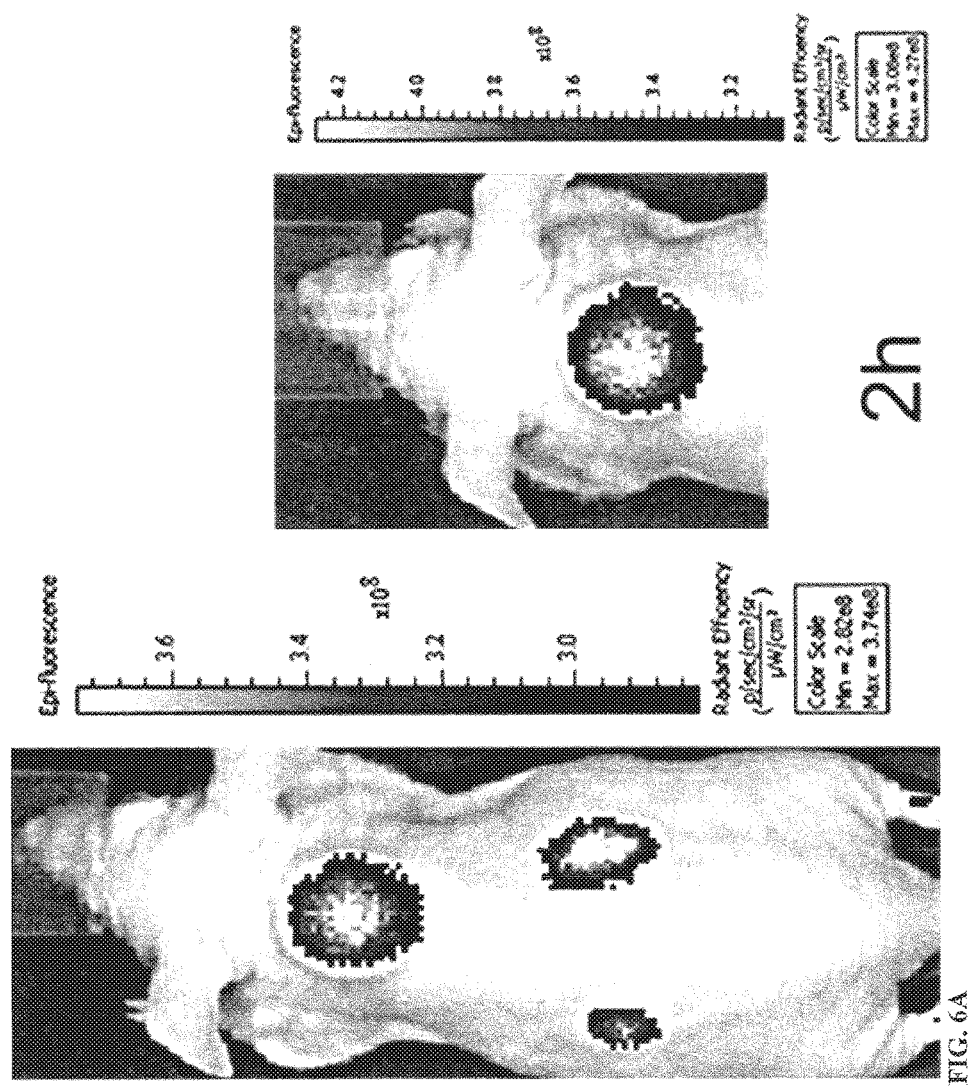
FIGS. 6A-6F: Overlay of whole body or half body fluorescence image over white light images after adjusting the threshold. 22Rv1 human prostate tumor xenograft bearing mouse was injected with 10 nmol of 1: OTL78 and imaged with IVIS imager (ex=745 nm, em=ICG, exposure time=1 s) at different time intervals.
Figure 6B:
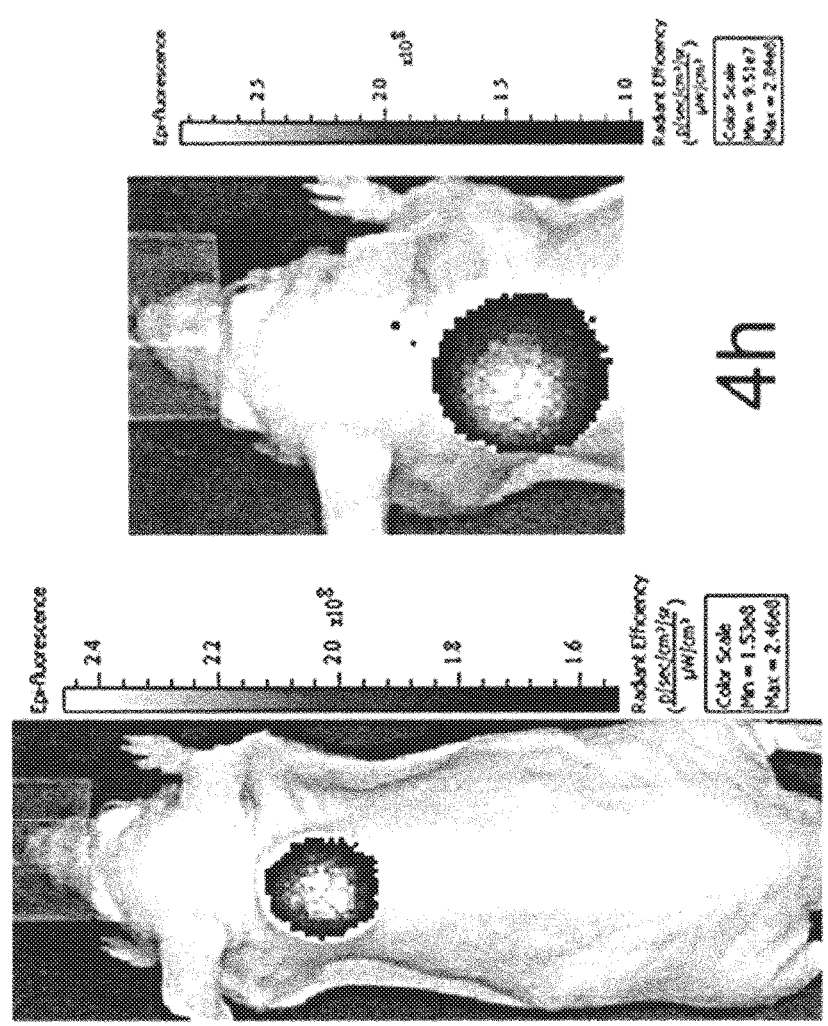
Figure 6C:
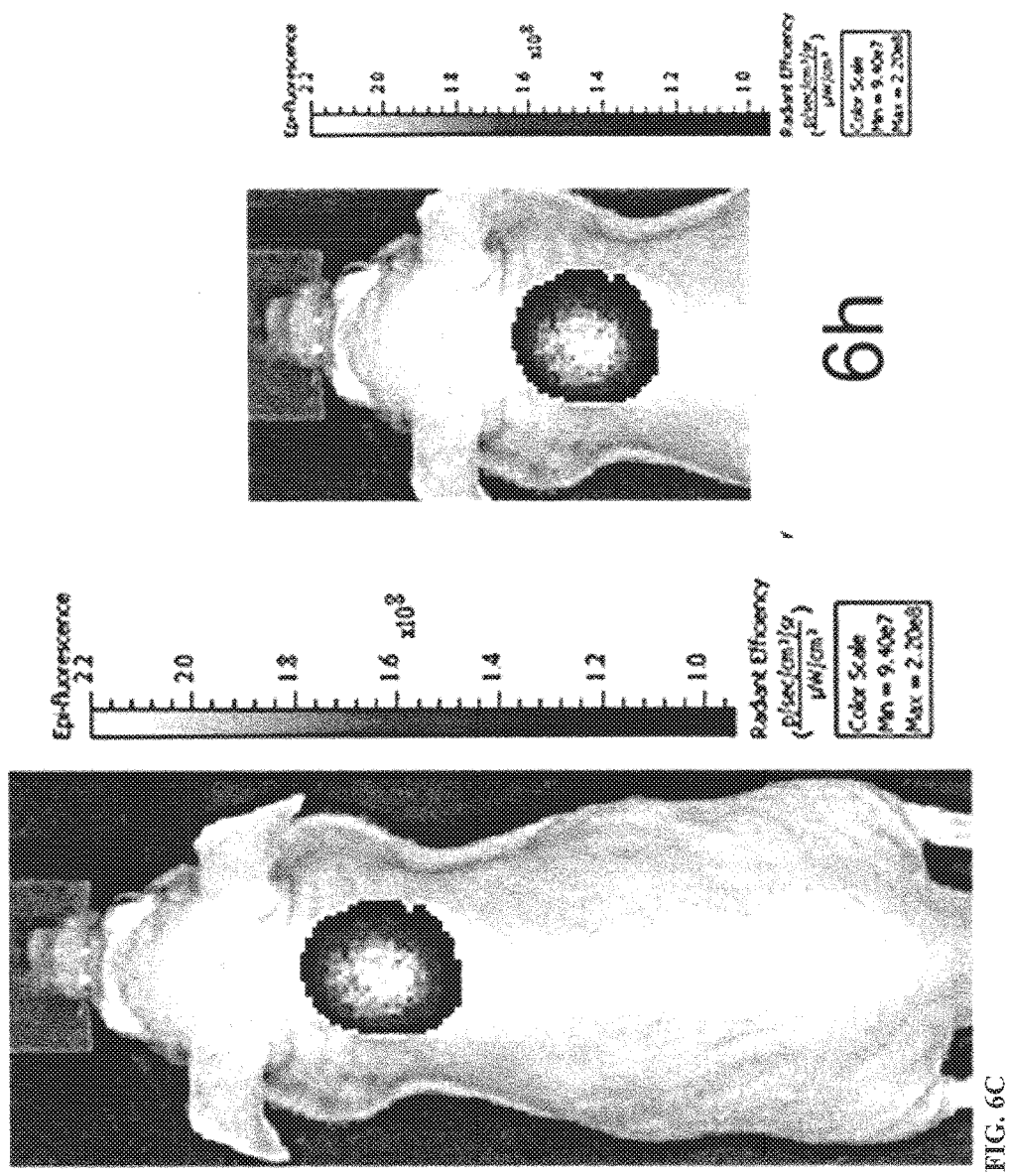
Figure 6D:
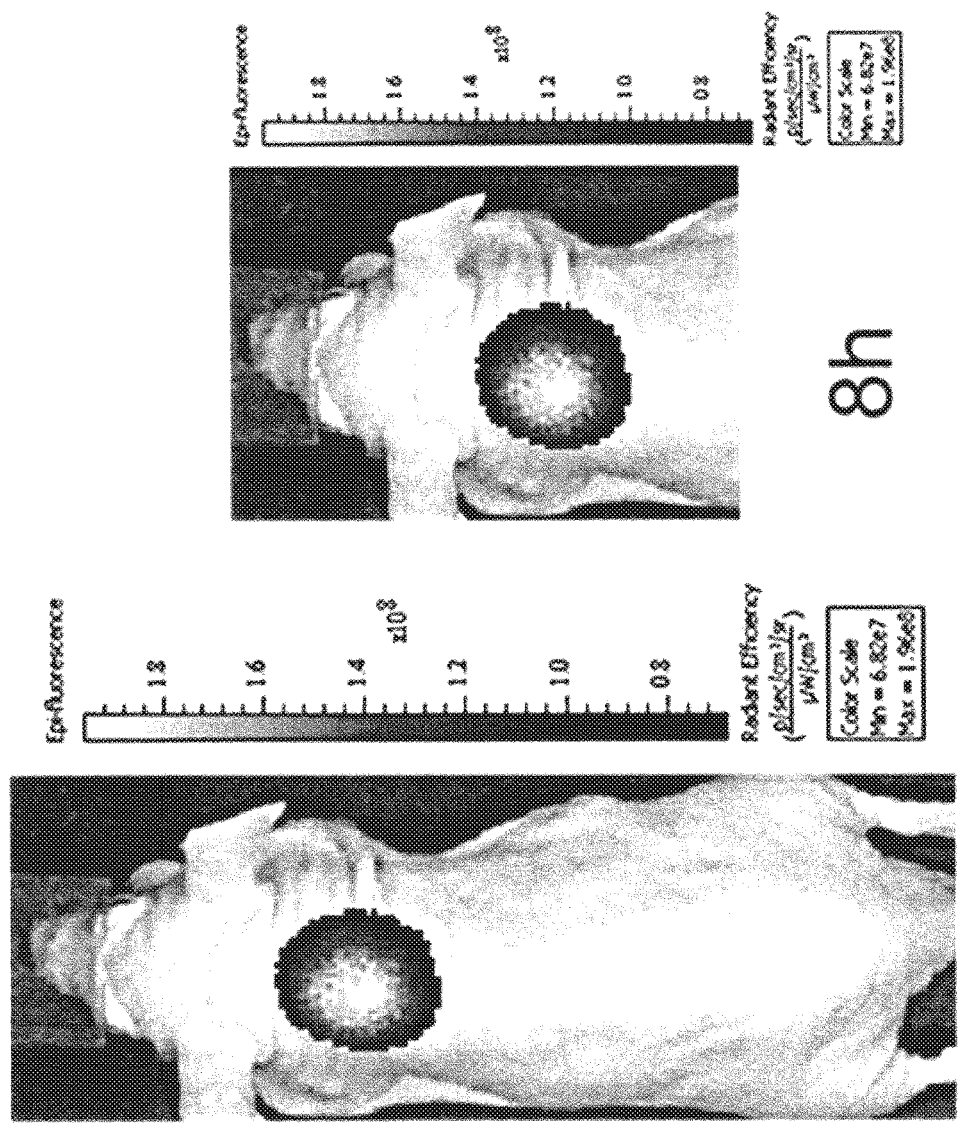
Figure 6E:
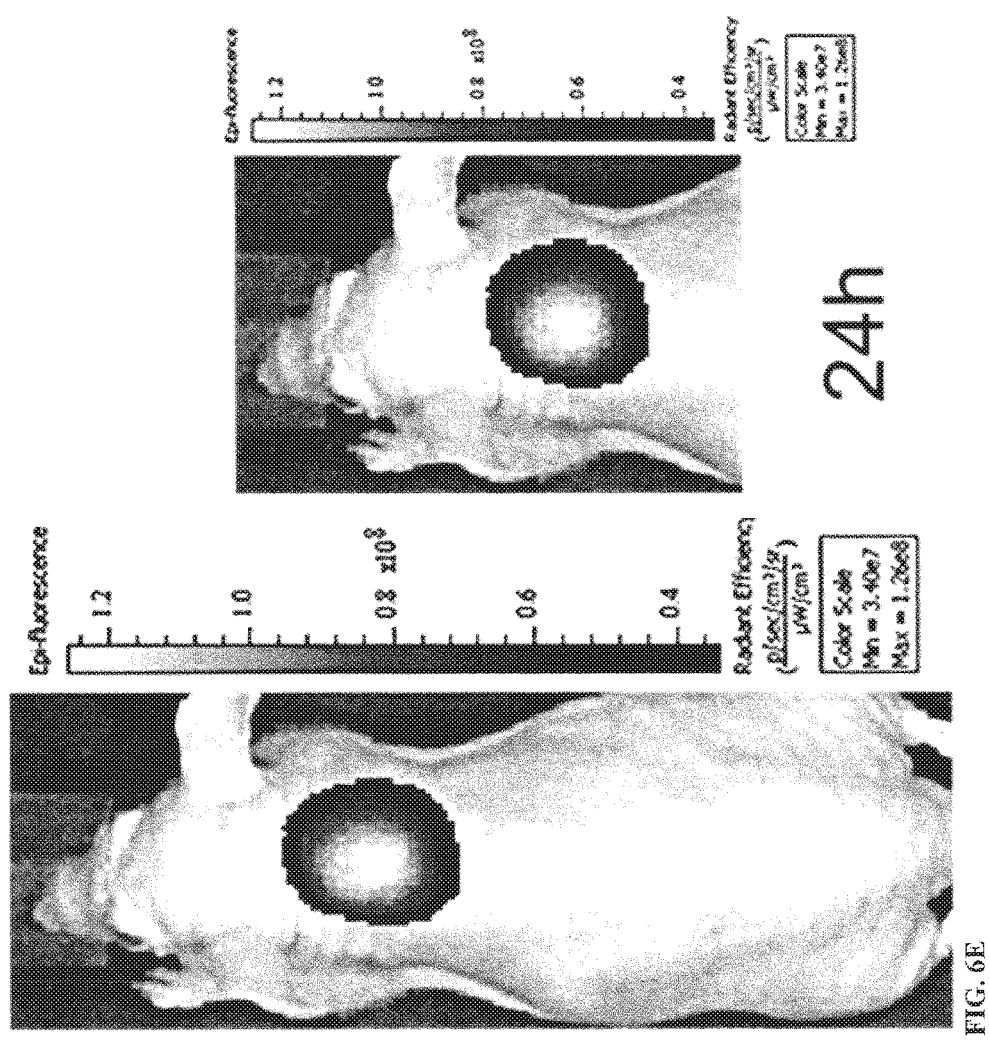
Figure 6F:
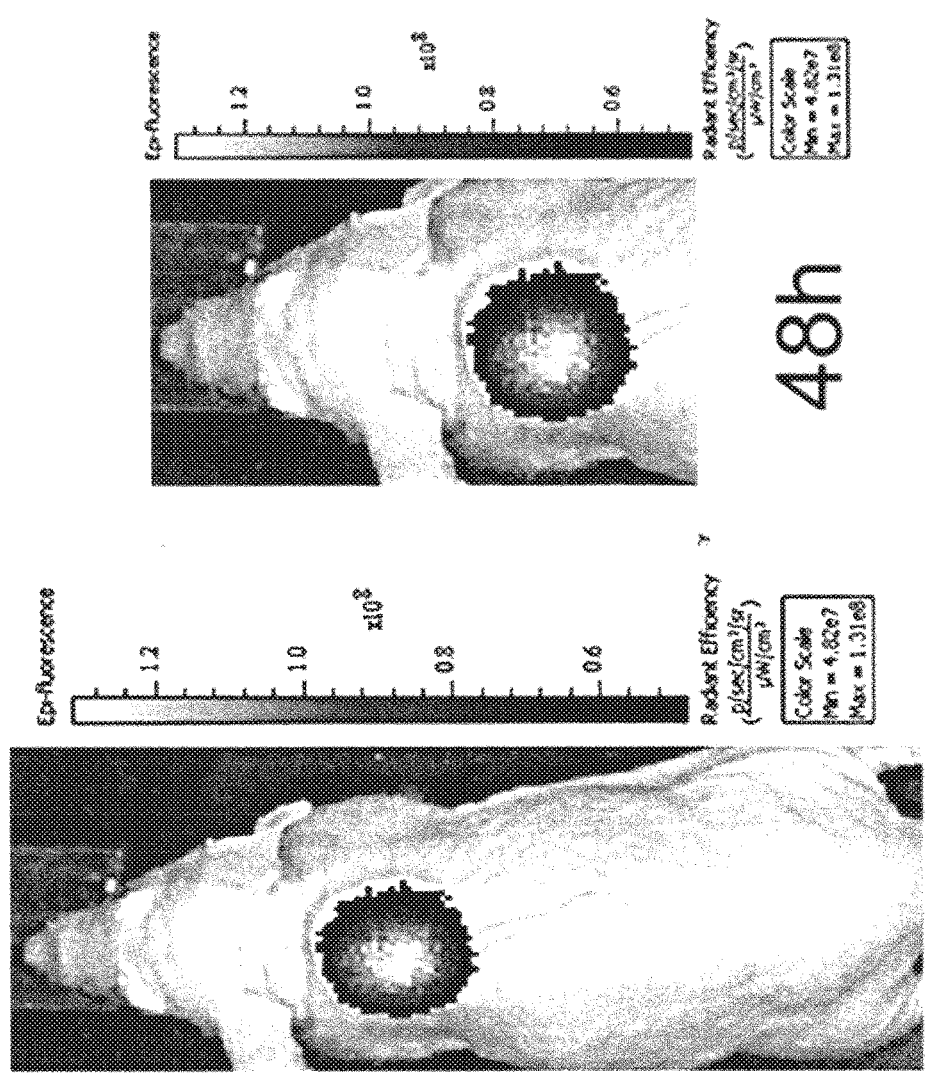

Pre-Clinical Evaluation of PSMA-Targeted NIR Dye Conjugates With Random Variation of Length of the Linker/Spacer Between the Ligand and the NIR Dye Conclusion: The compound 1: OTL78 is excited at 776 nm and emits at 796 nm (FIG. 1) demonstrating 20 nm Stokes shift with great NIR properties. The dissociation constant ($K_D$) of 5 derived from the studies was calculated to be 1 nM (FIG. 2) indicating very high affinity for PSMA. Whole-body imaging with mice bearing 22Rv1 tumor xenografts (FIG. 3) and their ex vivo tissue biodistribution (FIG. 4) indicated that the compounds 1: OTL78 was solely taken up in PSMA-positive tumors with no accumulation in other tissues, demonstrating a very high tumor-to-background ratio. As seen in FIGS. 5A & B, OTL78 did not accumulate in PSMA-negative PC3 prostate tumors demonstrating very high specificity for PSMA. Time dependent whole body imaging studies (FIG. 6) demonstrated that OTL78 saturated in the PSMA-positive tumors within 2 hours and remained in the tumor over 24 h.

Example (2)

General Synthesis of DUPA_PEG2_Phe_Tyr-50456 (1: OTL78)

Step I:

Molecular Weight: 299.32
6

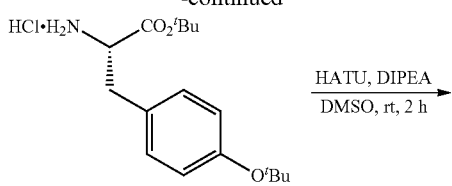

Molecular Weight: 329.86
7

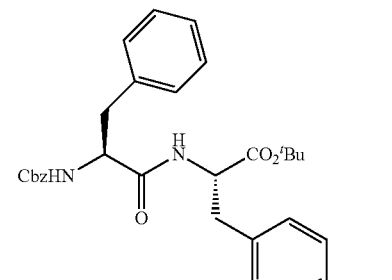

Molecular Weight: 574.71
8

Reactants for Step I:

| Chemicals | M. W. (g/mol) | Density (g/mL) | Equiv | Qty. (g) | Qty. (mL) | mmol |
|---|---|---|---|---|---|---|
| (L)-CbzNH-Phe-OH (6) | 299.33 | | 1.0 | 1.00 g | | 3.34 |
| (L)-NH$_2$-Tyr(—O$^t$Bu)—O$^t$Bu•HCl (7) | 329.87 | | 1.05 | 1.156 g | | 3.51 |
| HATU | 380.24 | | 1.05 | 1.334 g | | 3.51 |
| DIPEA | 129.24 | 0.742 | 2.5 | | 1.454 mL | 8.35 |
| DMSO | | | 0.33M | | 10 mL | |

A 50 mL round bottom flask was charged with a stirring bar, (L) phenylalanine with a carboxybenzyl (Cbz) protecting group on the amine ((L)-CbzNH-Phe-OH [(6), 1.0 g, 3.34 mmol, 1 equiv.)]), ((L)-Tyrosine with tert-butyl protecting groups on the carboxyl group and the phenyl oxygen ((L)-NH$_2$-Tyr(—O$^t$Bu)-O$^t$Bu.HCl [(7), 1.156 g, 3.51 mmol, 1.05 equiv.)], and HATU (1.334 g, 3.51 mmol, 1.05 equiv.). DMSO (10 mL) was then added to the round bottom flask to give a suspension [suspension I-A]. HATU is 1-[Bis(dimethylamino)methylene]-1H-1,2,3-triazolo[4,5-b]pyridinium 3-oxid hexafluorophosphate. DIPEA is N,N-Diisopropylethylamine. DMSO is dimethyl sulfoxide. DIPEA (1.454 mL, 8.35 mmol, 2.5 equiv.) was added slowly to suspension I-A at 23° C., over 5 minutes to form clear solution. The reaction mixture was stirred at 23° C. for 2 h. The progress of the reaction was monitored by LCMS. The reaction mixture was added drop wise to a stirred 60 mL of cold 5% citric acid-1 N NaCl solution (prepared by adding 5.85 g of NaCl to 100 mL of 5% Citric acid solution) to give precipitate of crude compound 8 ((CbzNH-(L)Phe-NH-(L)Tyr(—O$^t$Bu)-O$^t$Bu).HCl. The precipitate was filtered and dissolved in EtOAc (75 mL). The EtOAc layer was washed with water (25 mL) followed by brine (25 mL) and dried over anhyd. Na$_2$SO$_4$. The dried EtOAc layer was filtered and concentrated under vacuum. The crude compound 8 was analyzed by LC/MS (FIGS. 7A-7D) and used for the next step without further purification. Crude compound 8 was isolated with 95% yield.

Figure 7A:
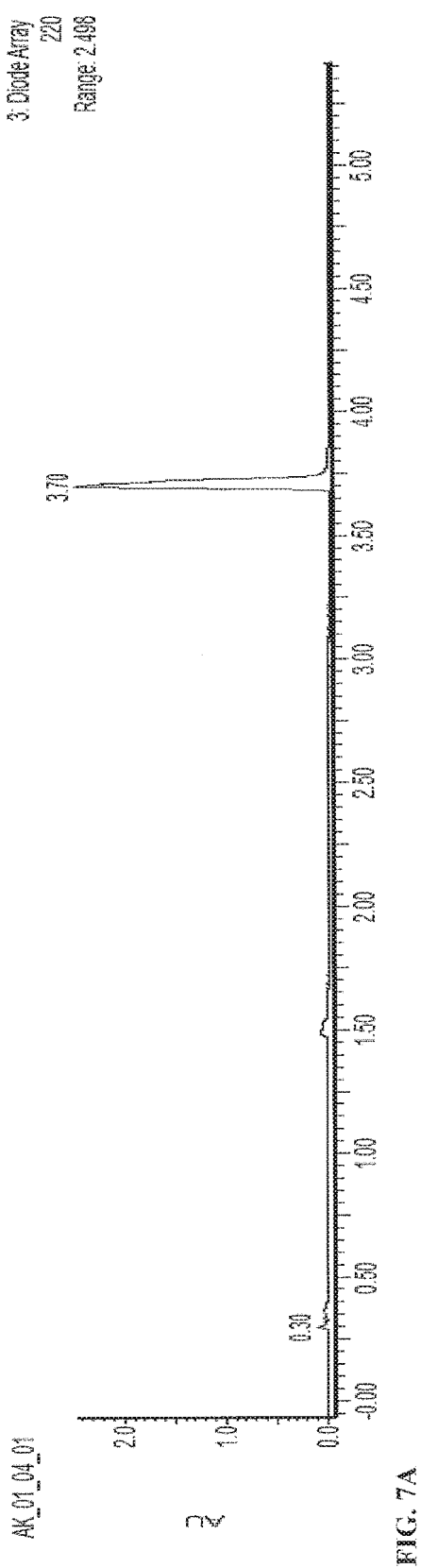
FIG. 7A depicts the LC/MS chromatogram for the crude compound 8: Instrument: Acquity UPLC, Waters Column: BEH C18, 1.7 μm, 2.1×50 mm. Eluent A: 20 mM aq. $NH_4OAc$; Eluent B: ACN. Gradient: 5% B-75% B in 2.2 min following the gradient program shown in Table #. Run time: 7 min. Flow rate: 0.35 mL/min. Detector: 220 nm UV detector.
Figure 7B:
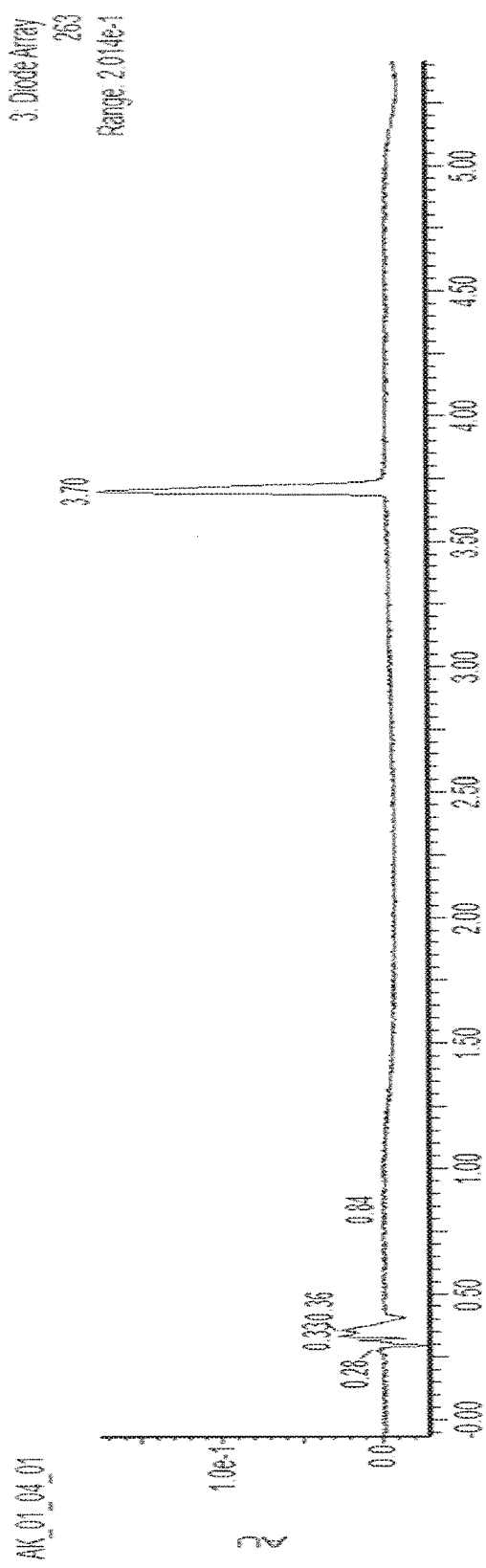
FIG. 7B illustrates the LC/MS chromatogram for the crude compound 8: Same conditions of FIG. 7A except detector is a 263 nm UV detector.
Figure 7C:
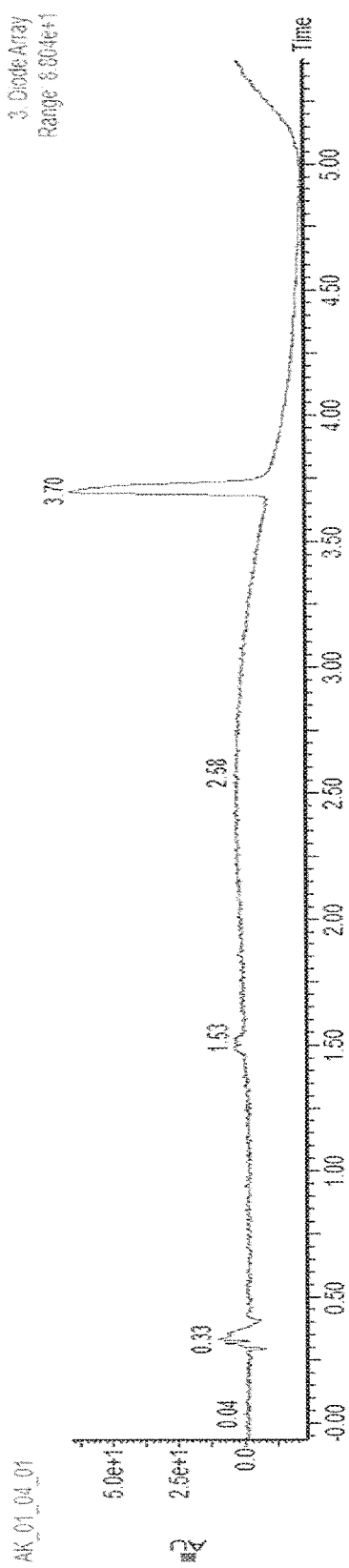
FIG. 7C shows the LC/MS chromatogram for the crude compound 8: Same conditions of FIG. 7A except detector is a diode array.
Figure 7D:
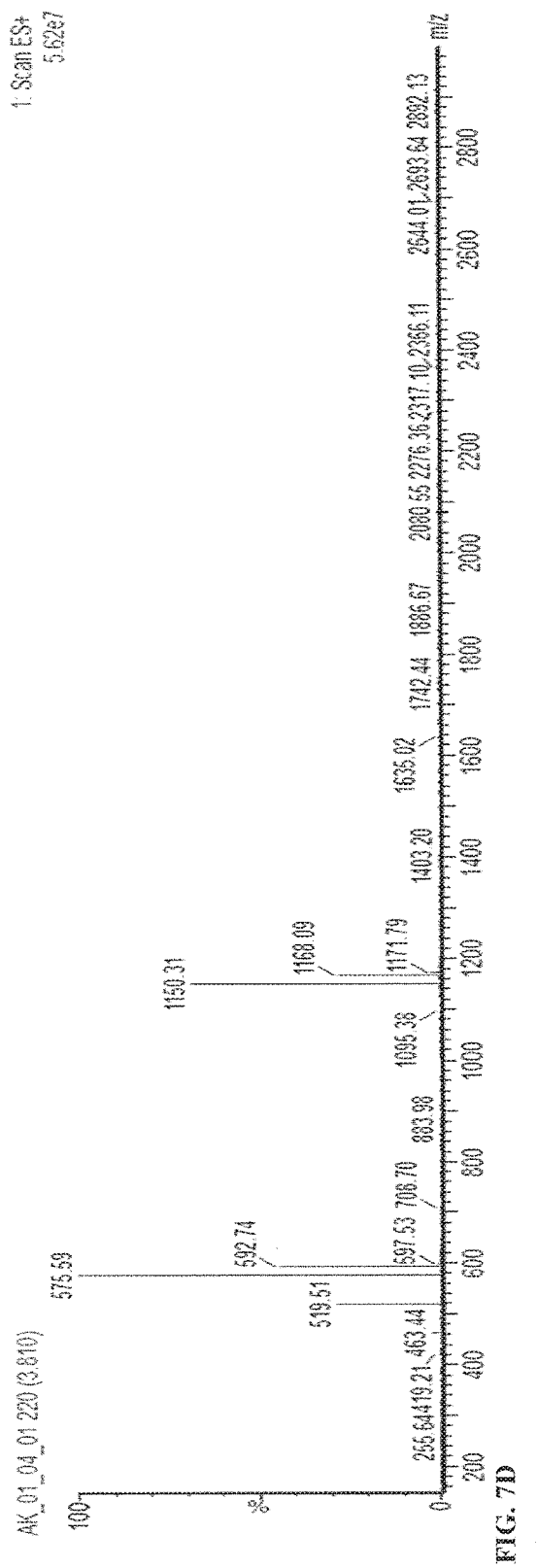
FIG. 7D depicts the mass spectra for crude compound 8 analyzed using positive mode electrospray ionization mass spectrometry illustrating crude compound 8+H (m/z 575.5) and its dimer (m/z 1150).

LC/MS method for crude compound 8: Instrument: Acquity UPLC, Waters Column: BEH C18, 1.7 μm, 2.1×50 mm. 95%-5%-95% ammonium acetate in 20 mM aqueous eluent with 5%-95%-5% acetonitrile in 7 minutes following the gradient program shown in Table 1. Flow rate is 0.35 mL/min. Detector is selected from the group consisting of 220 nm UV detector (FIG. 7A), 263 nm UV detector (FIG. 7B), a diode array (FIG. 7C).

TABLE 1

Eluent A: 20 mM aq. Ammonium Acetate (NH$_4$OAc); Eluent B: acetonitrile (ACN).

| Time | Flow rate mL/min | % A | % B |
|---|---|---|---|
| 0 | 0.35 | 95 | 5 |
| 2.2 | 0.35 | 25 | 75 |
| 2.8 | 0.35 | 5 | 95 |
| 4.0 | 0.35 | 5 | 95 |
| 4.6 | 0.35 | 95 | 5 |
| 7 | 0.35 | 95 | 5 |
| 7.01 | 0 | 95 | 5 |

Step II: Carboxybenzyl (Cbz) Deprotection

A 50 mL rb flask was charged with a stir bar, CbzNH-Phe-Tyr-(O$^t$Bu)-O$^t$Bu [(8), 1.5 g, 2.61 mmol], and DCM (9 mL). After dissolving the reaction mixture, Pd/C (10% Pd basis, 20% wt/wt, 300 mg) was added in portions to the round bottom flask followed by anhy. MeOH (18 mL). The reaction mixture was degassed three times and H2 gas was bubbled through the reaction mixture for 3 hours under stirring at room temperature.

Figure 8A:
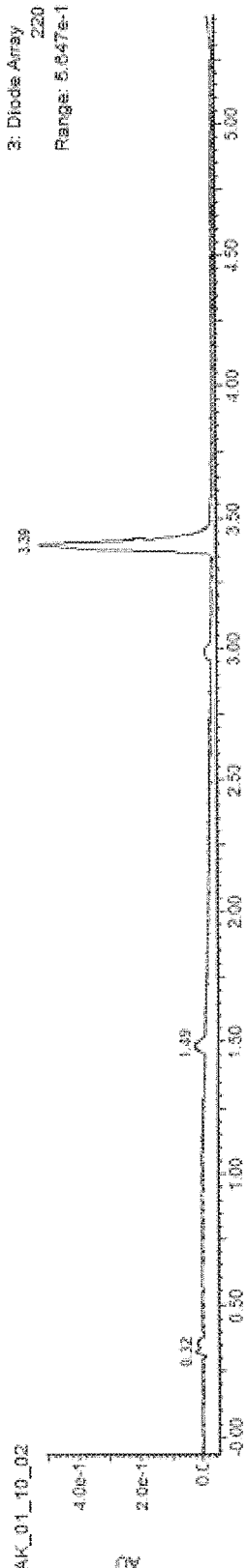
FIG. 8A illustrates LC/MS chromatogram for the crude compound 9: Same conditions of FIG. 7A.
Figure 8B:
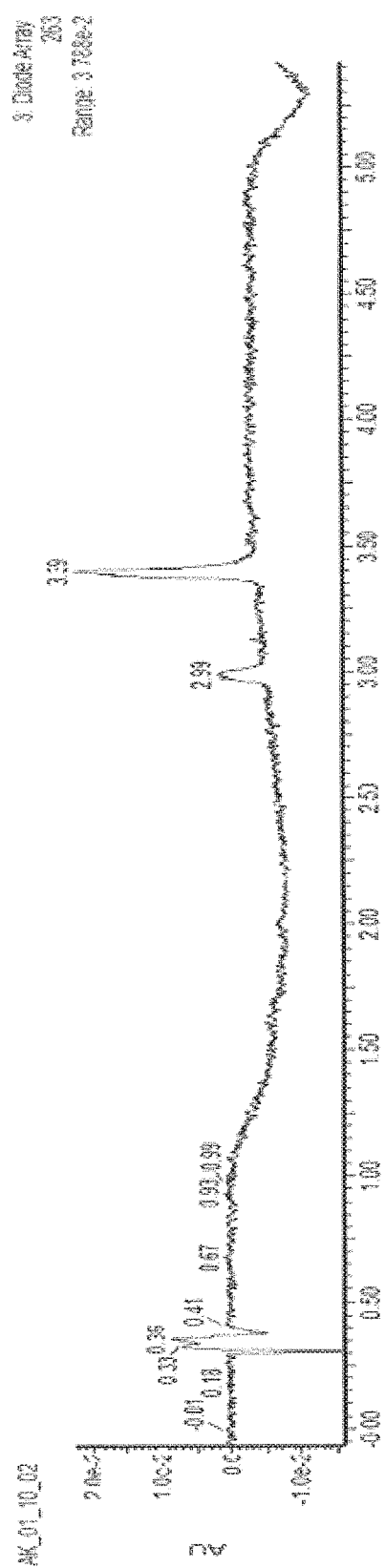
FIG. 8B shows the LC/MS chromatogram for the crude compound 9: Same conditions of FIG. 7B.
Figure 8C:
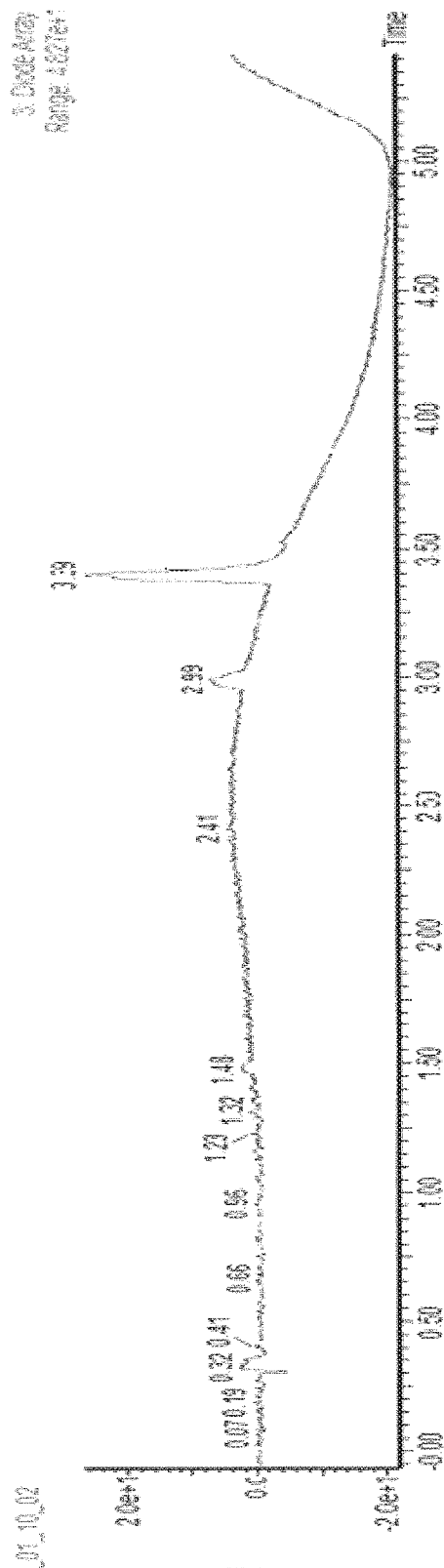
FIG. 8C depicts the LC/MS chromatogram for the crude compound 9: Same conditions of FIG. 7C.
Figure 8D:
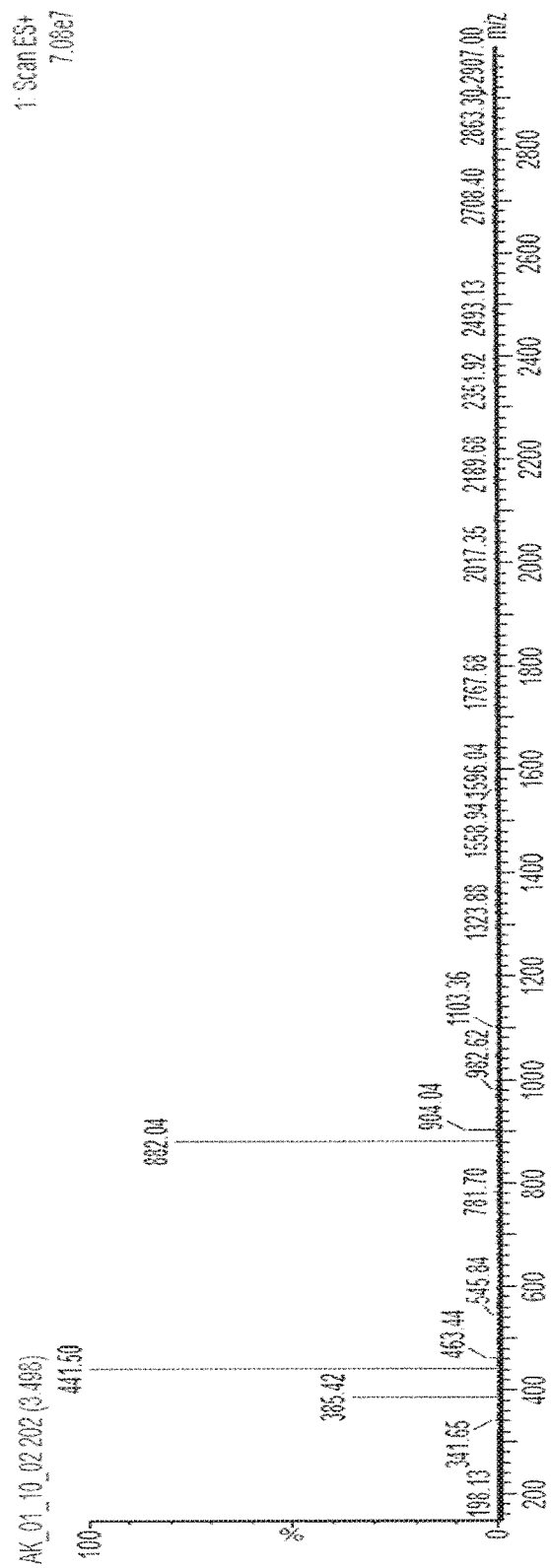
FIG. 8D illustrates the mass spectra for crude compound 9 analyzed using positive mode electrospray ionization mass spectrometry illustrating crude compound 9+H (m/z 441.5) and its dimer (m/z 882).

LC/MS method for crude compound 9 is the same as LC/MS method for crude compound 8. The detector is selected from the group consisting of 220 nm UV detector (FIG. 8A), 263 nm UV detector (FIG. 8B), a diode array (FIG. 8C) and a mass spectrometer (FIG. 8D).

Figure 9A:
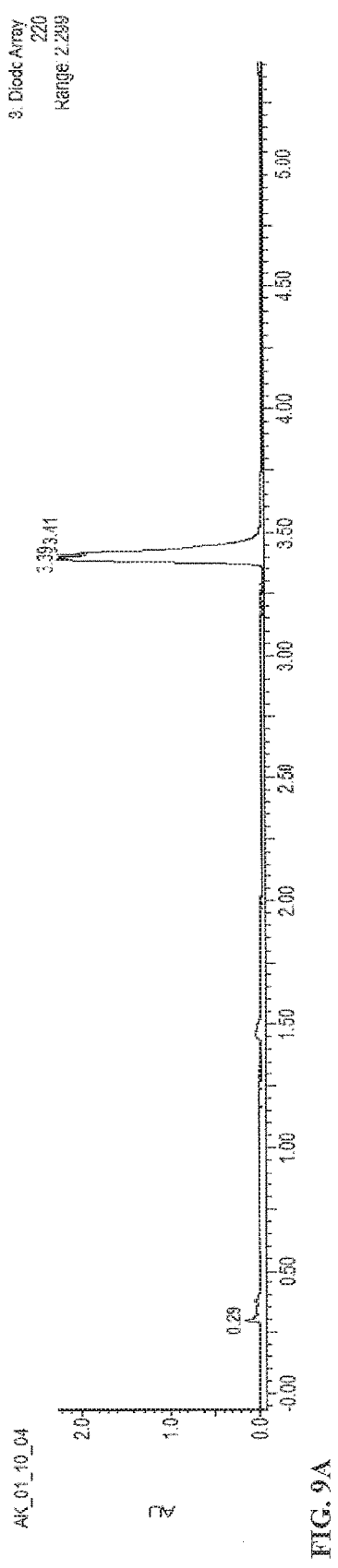
FIG. 9A shows the LC/MS chromatogram for the crude compound 11: Same conditions of FIG. 7A.
Figure 9B:
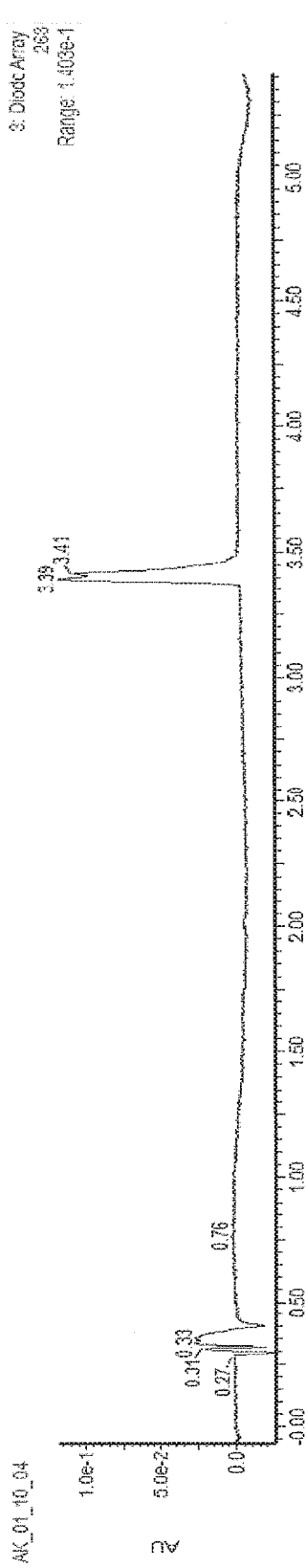
FIG. 9B depicts the LC/MS chromatogram for the crude compound 11: Same conditions of FIG. 7B.
Figure 9C:
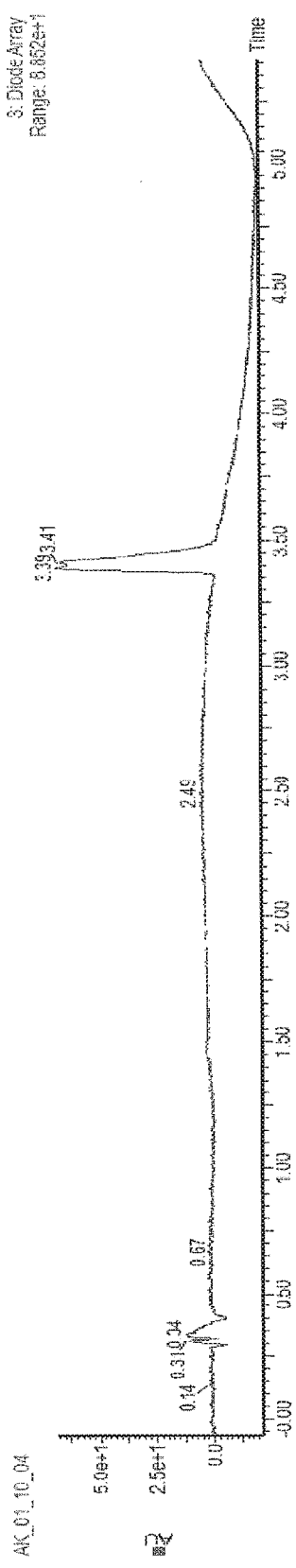
FIG. 9C illustrates the LC/MS chromatogram for the crude compound 11: Same conditions of FIG. 7C.
Figure 9D:
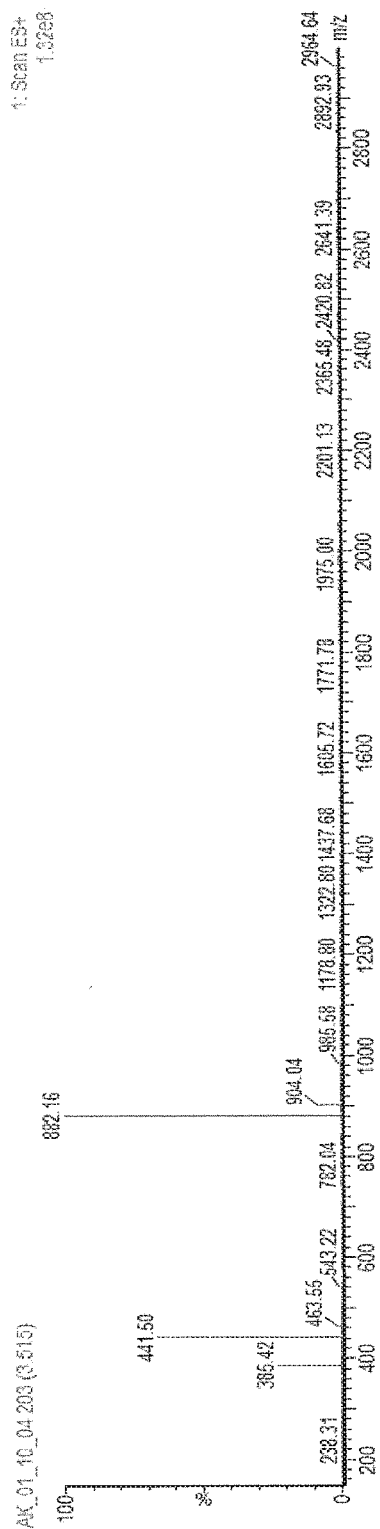
FIG. 9D shows the mass spectra for crude compound 11 analyzed using positive mode electrospray ionization mass spectrometry illustrating crude compound 11+H (m/z 734.86) and its dimer (m/z 1486.68).

The reaction mixture was filtered through a Celite plug, washed with methanol (MeOH), and the filtrate was concentrated under vacuum to afford crude compound 9. Crude compound 9 was analyzed by LC/MS and used for the next step without further purification. Compound 9 was isolated with 92% yield. LC/MS method after purification of compound 9 is the same as LC/MS method for crude compound 9. The detector is selected from the group consisting of 220 nm UV detector (FIG. 9A), 263 nm UV detector (FIG. 9B), a diode array (FIG. 9C) and a mass spectrometer (FIG. 9D).

Step III: PEG$_2$ Addition

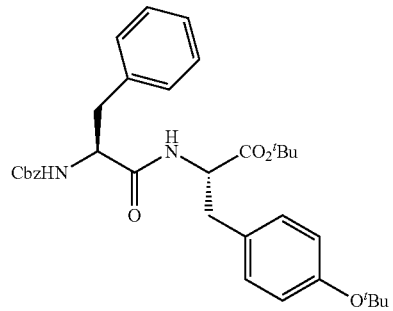

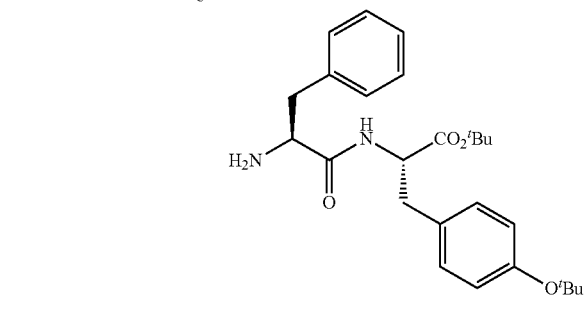

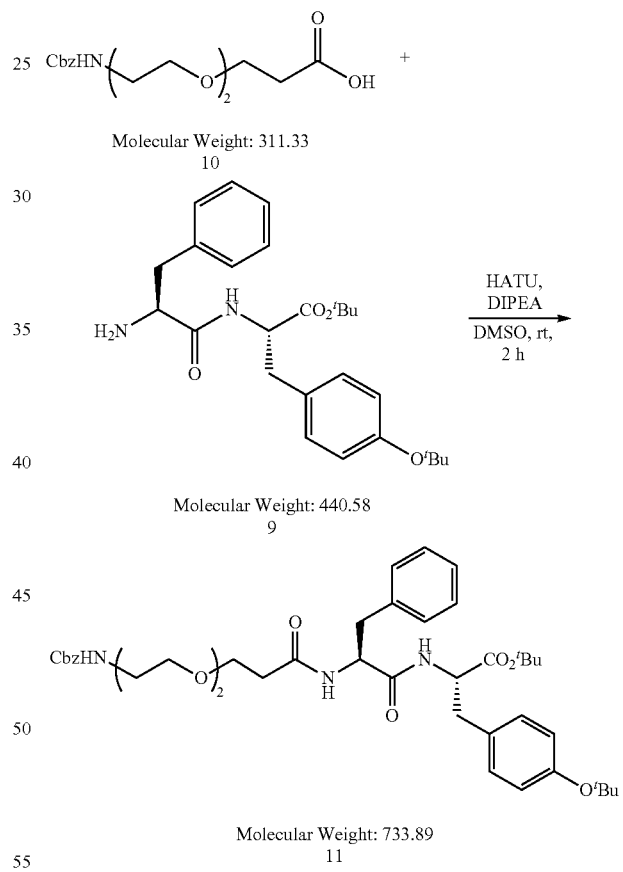

Reactants for Step II:

| Chemicals | M. W. (g/mol) | Density (g/mL) | Equiv | Qty. (g) | Qty. (mL) | mmol |
|---|---|---|---|---|---|---|
| CbzNH-Phe-Tyr-(O$^t$Bu)—O$^t$Bu (8) | 574.71 | | 1.0 | 1.50 g | | 2.61 |
| Pd/C | 10% Pd basis | | 20% wt/wt | 0.300 g | | |
| DCM:MeOH (1:2) | | | 0.1M | | 27 mL (9 mL:18 mL) | |

Reactants for Step III:

| Chemicals | M. W. (g/mol) | Density (g/mL) | Equiv | Qty. (g) | Qty. (mL) | mmol |
|---|---|---|---|---|---|---|
| CbzNH—PEG$_2$—CO$_2$H (10) | 311.33 | | 1.0 | 3.10 g | | 9.96 |
| NH$_2$-Phe-Tyr(O$^t$Bu)—O$^t$Bu (9) | 440.58 | | 1.0 | 4.39 g | | 9.96 |
| HATU | 380.24 | | 1.05 | 4.0 g | | 10.46 |
| DIPEA | 129.24 | 0.742 | 2.0 | | 3.48 mL | 19.92 |
| DMSO | | | 0.33M | | 20 mL | |

A 50 mL round bottom flask was charged with a stir bar, polyethylene glycol reactant with a carboxybenzyl (Cbz) protecting group on the amine (Cbz-NH-PEG2-CO2H [(10) 3.10 g, 9.96 mmol, 1 equiv.), NH2-Phe-Tyr(OtBu)-OtBu (9, 4.39 g, 9.96 mmol, 1.0 equiv.), and HATU (4.0 g, 10.46 mmol, 1.05 equiv.). DMSO (20 mL) was then added to the round bottom flask under argon and stirred to dissolve.

Figure 10A:
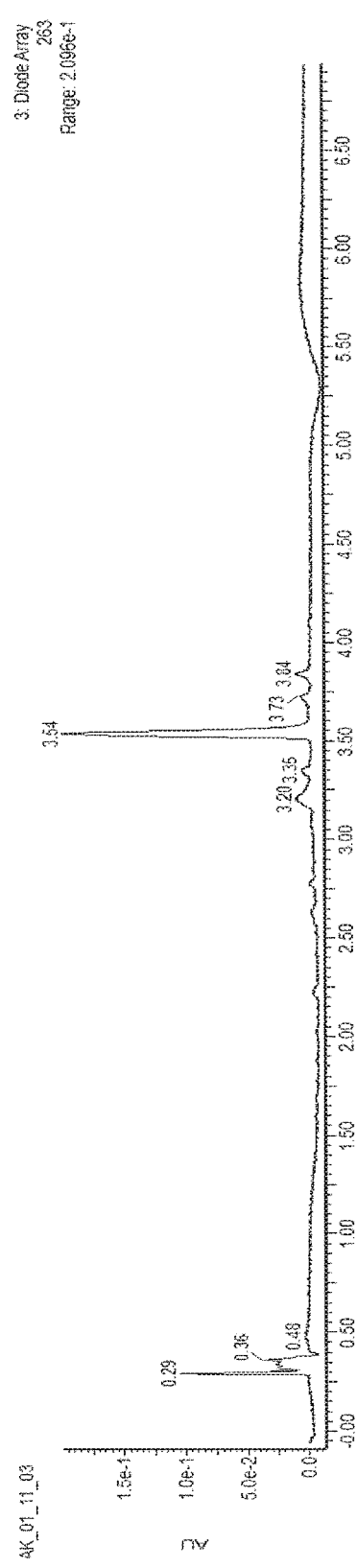
FIG. 10A depicts the LC/MS chromatogram for the crude compound 12: Same conditions of FIG. 7A.
Figure 10B:
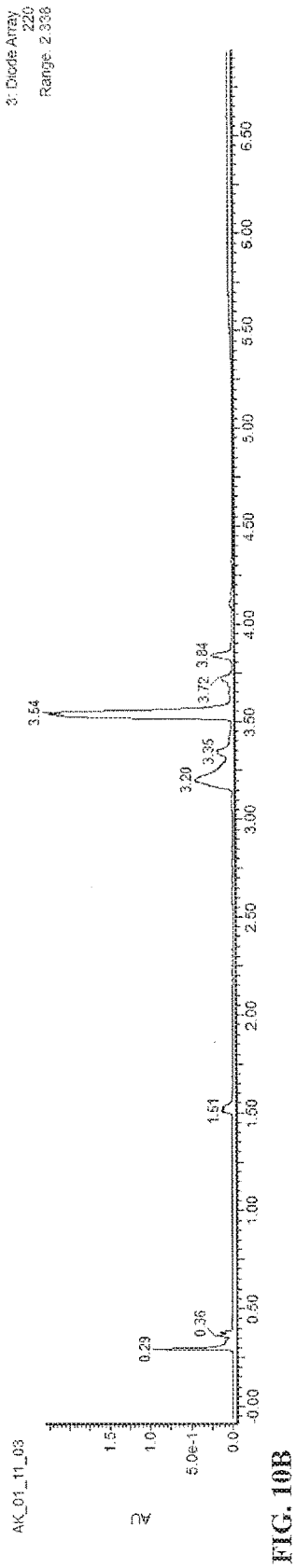
FIG. 10B illustrates the LC/MS chromatogram for the crude compound 12: Same conditions of FIG. 7B.
Figure 10C:
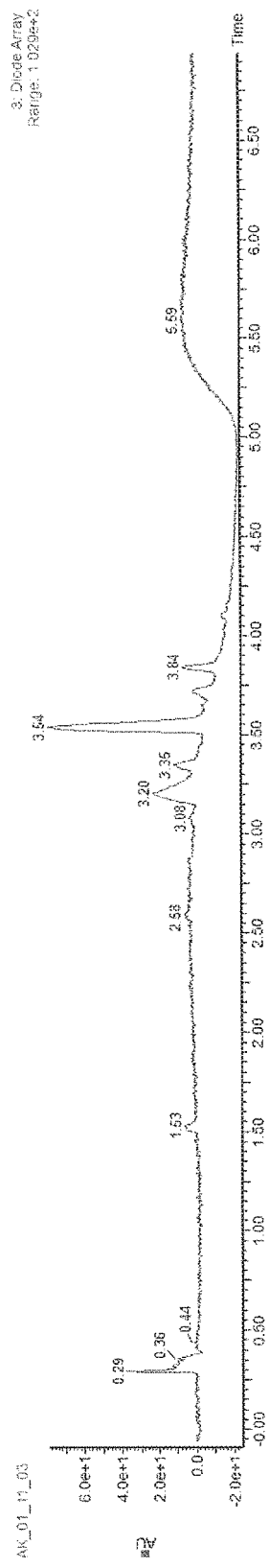
FIG. 10C shows the LC/MS chromatogram for the crude compound 12: Same conditions of FIG. 7C.
Figure 10D:
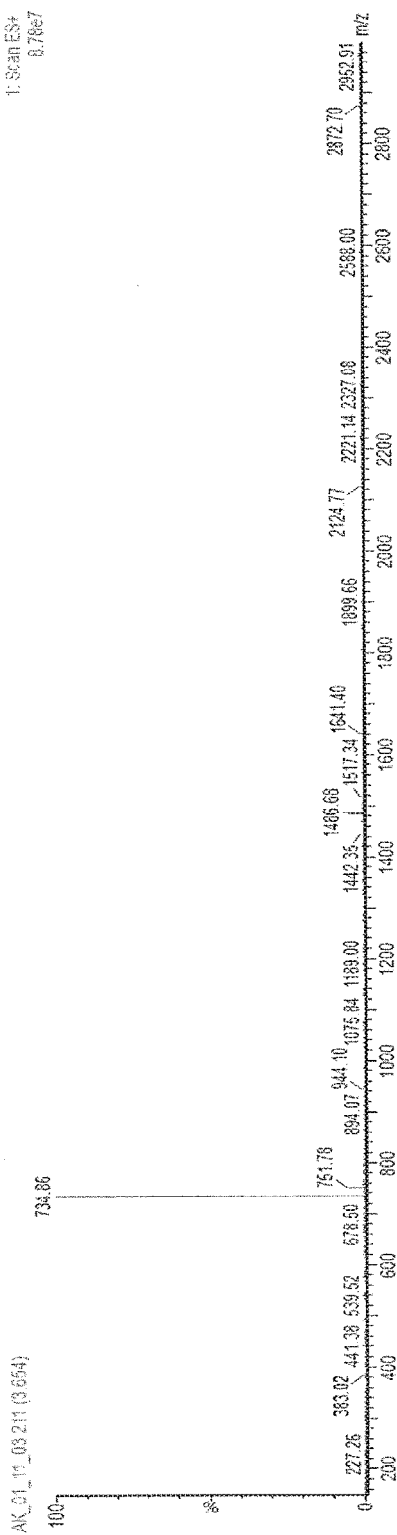
FIG. 10D depicts the mass spectra for crude compound 12 analyzed using positive mode electrospray ionization mass spectrometry illustrating crude compound 12+H (m/z 600.7) and its dimer (m/z 1200).

DIPEA (3.48 mL, 19.92 mmol, 2.0 equiv.) was added slowly to reaction mixture at 23° C., over 5 minutes. The reaction was stirred at 23° C. for 2 h and progress of the reaction was monitored by LC/MS. The detector is selected from the group consisting of 220 nm UV detector (FIG. 10A), 263 nm UV detector (FIG. 10B), a diode array (FIG. 10C) and a mass spectrometer (FIG. 10D).

The reaction mixture was added dropwise to a stirred 120 mL of cold 5% citric acid-1 N NaCl solution (prepared by adding 58.5 g of NaCl to 1000 mL of 5% Citric acid solution) to precipitate as a gummy solid.

Filtered the gummy residue after decanting water and dissolved it in EtOAc (150 mL). The EtOAc layer was washed with water (100 mL), followed by brine (100 mL), and then dried over anhydrous Na2SO4. The dried EtOAc layer was filtered and concentrated under vacuum.

The crude product was purified using a silica-gel column using DCM:EtOAc as a mobile phase. Product was eluted between 20-40% EtOAc in DCM. The combined pure fractions were concentrated under vacuum and used in the next step (crystallization methods to avoid silica-gel column chromatography in progress).

Figure 11A:
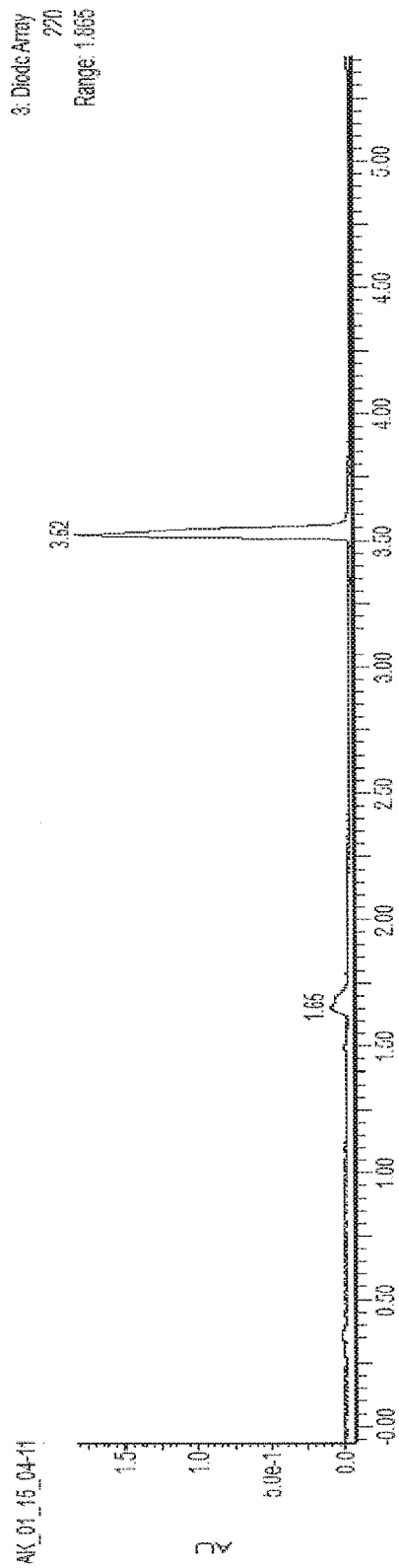
FIG. 11A illustrates the LC/MS chromatogram for the crude compound 13: Same conditions of FIG. 7A.
Figure 11B:
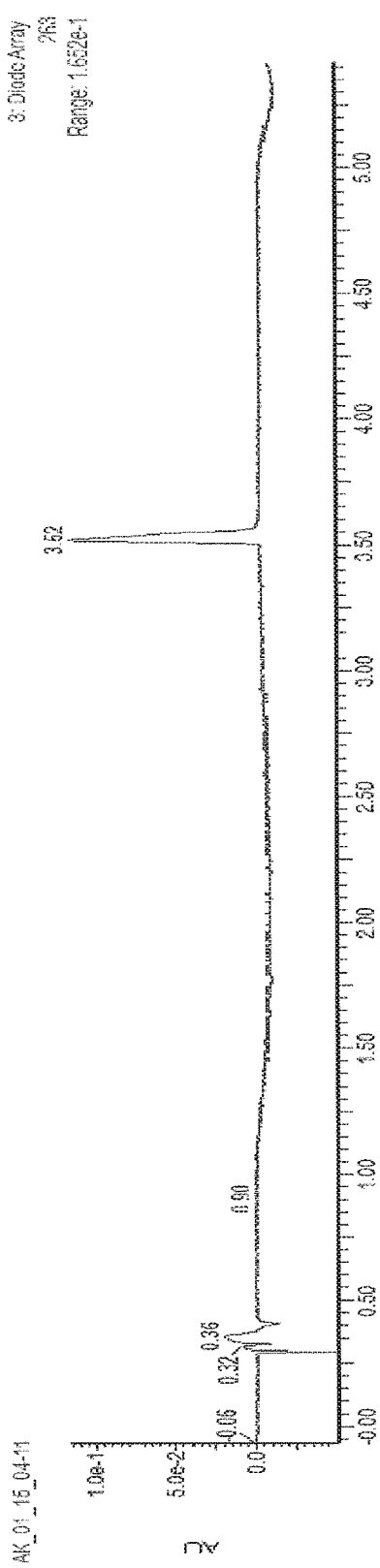
FIG. 11B shows the LC/MS chromatogram for the crude compound 13: Same conditions of FIG. 7B.
Figure 11C:
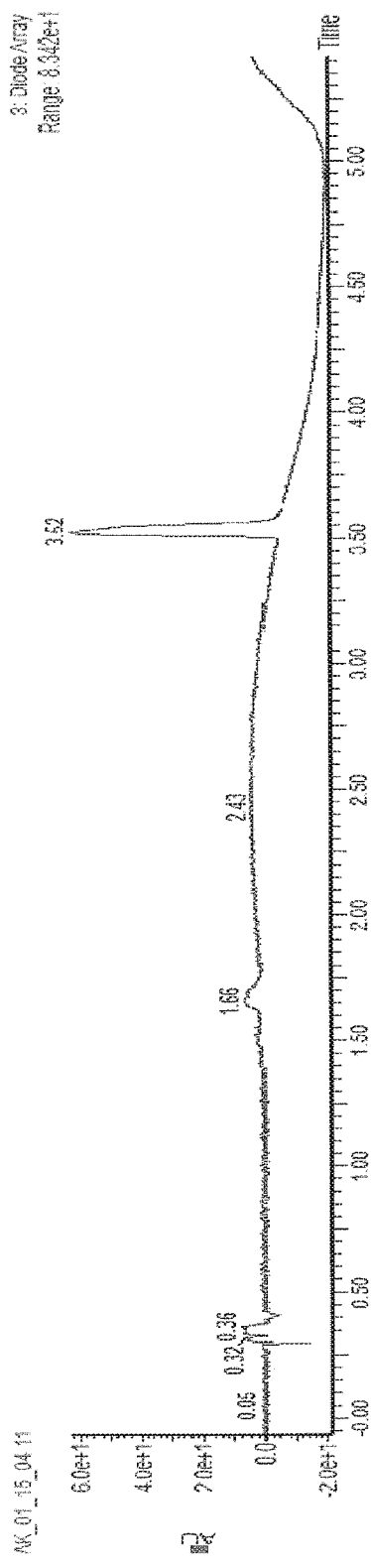
FIG. 11C depicts the LC/MS chromatogram for the crude compound 13: Same conditions of FIG. 7C.
Figure 11D:
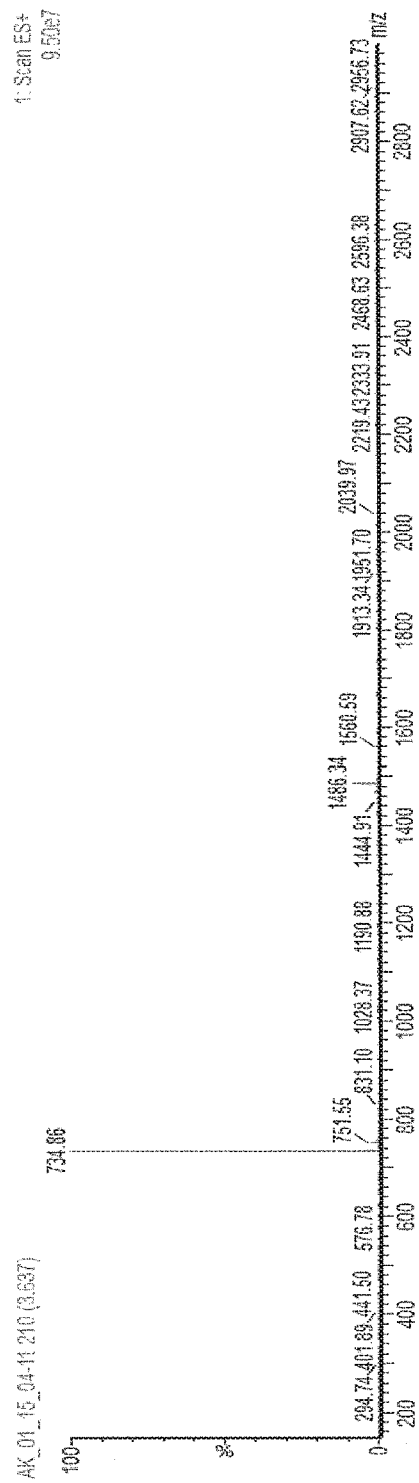
FIG. 11D illustrates the mass spectra for crude compound 13 analyzed using positive mode electrospray ionization mass spectrometry illustrating crude compound 13+H (m/z 1071.2) and its dimer (m/z 2142).

Purified compound 11 was isolated with 86% yield (reaction optimization in progress to improve yield). LC/MS method after purification of compound 11 is the same as LC/MS method for crude compound 9. The detector is selected from the group consisting of 220 nm UV detector (FIG. 11A), 263 nm UV detector (FIG. 11B), a diode array (FIG. 11C) and a mass spectrometer (FIG. 11D).

Step IV: Carboxybenzyl (Cbz) Deprotection

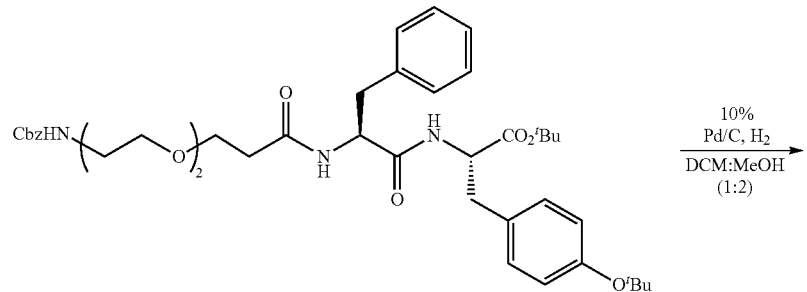

Molecular Weight: 733.89
11

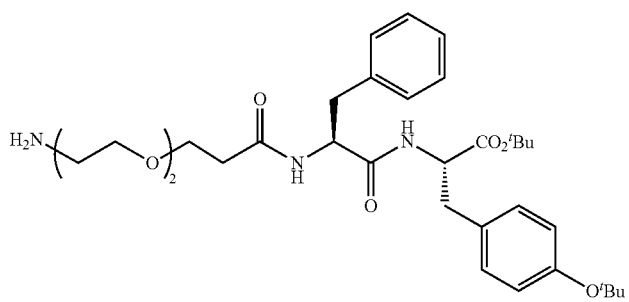

Molecular Weight: 599.76
12

Reactants for Step IV:

| Chemicals | M. W. (g/mol) | Density (g/mL) | Equiv | Qty. (g) | Qty. (mL) | mmol |
|---|---|---|---|---|---|---|
| CbzNH—PEG$_2$-Phe-Tyr(O$^t$Bu)—O$^t$Bu (11) | 733.89 | | 1.0 | 0.80 g | | 1.09 |
| Pd/C | | 10% Pd basis | 10% wt/wt | 0.08 g | | |
| DCM:MeOH (1:2) | | | | 0.1M | 10 mL | |

10

Figure 12A:
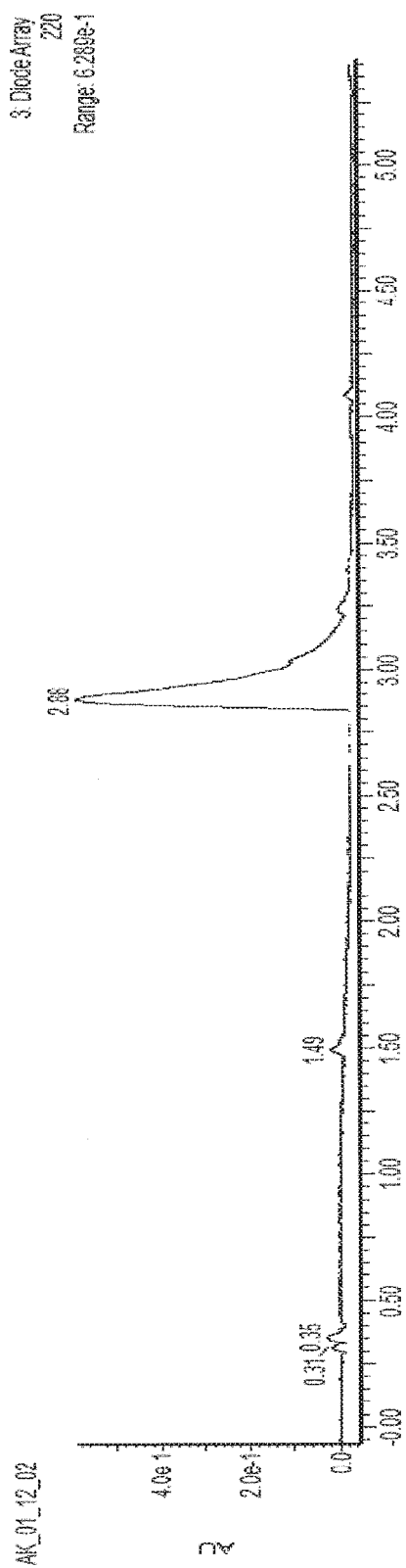
FIG. 12A shows the LC/MS chromatogram after purification of compound 5: Same conditions of FIG. 7A.
Figure 12B:
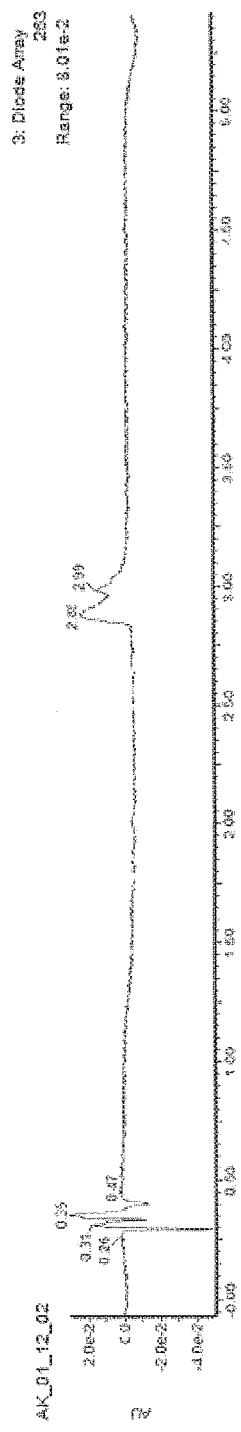
FIG. 12B depicts the LC/MS chromatogram after purification of compound 5: Same conditions of FIG. 7A.
Figure 12C:
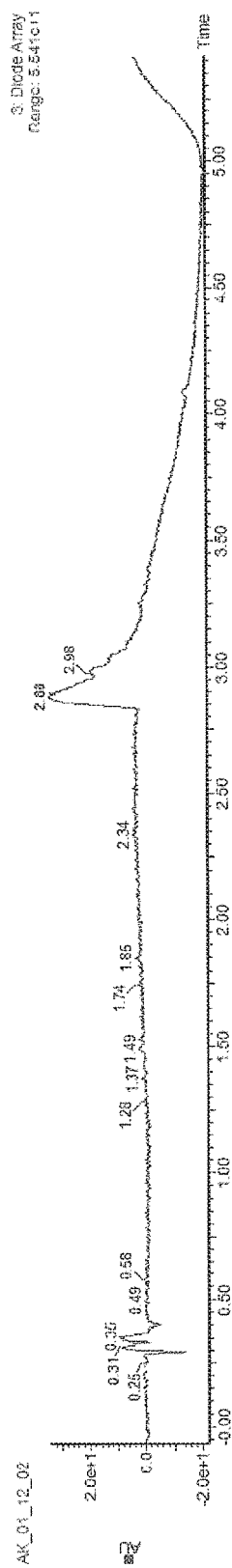
FIG. 12C illustrates the LC/MS chromatogram after purification of compound 5: Same conditions of FIG. 7C.
Figure 12D:
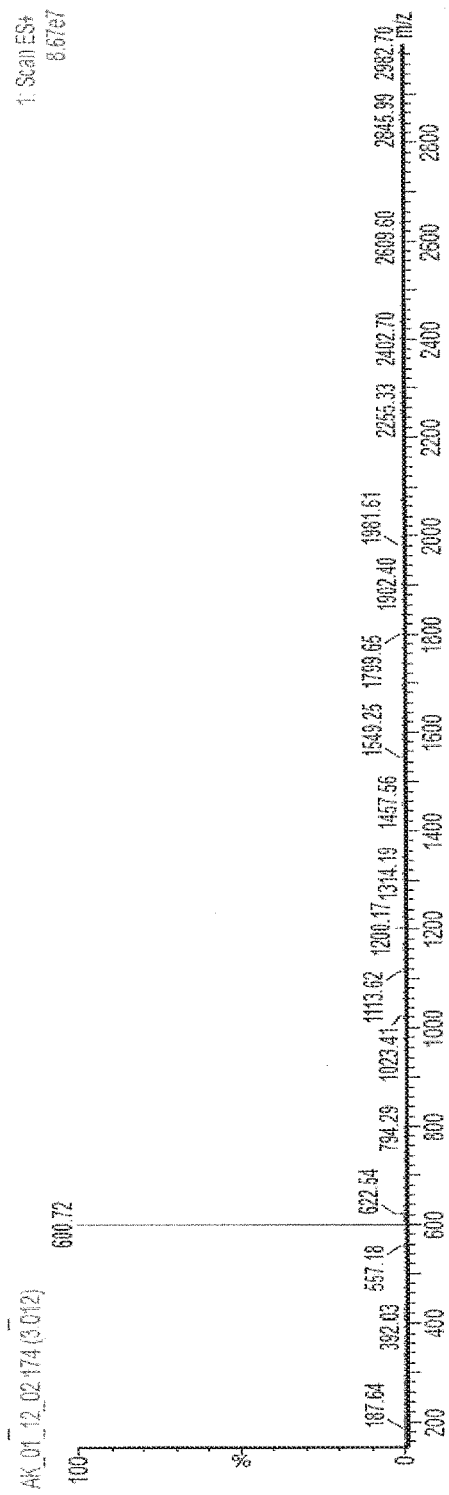
FIG. 12D shows the mass spectra after purification of compound 5 analyzed using positive mode electrospray ionization mass spectrometry illustrating compound 5+H (m/z 790.6).

A 50 mL round bottom flask was charged with a stir bar, CbzNH-PEG2-Phe-Tyr(OtBu)-OtBu [(11), 0.80 g, 1.09 mmol), and DCM (3 mL). After dissolving the reaction mixture, Pd/C (10% wt/wt, 0.08 g) was added in portions followed by anhydrous methanol (7 mL). The reaction mixture was degassed three times and hydrogen bubbled through reaction mixture for 3 hours under stirring at room temperature. Progress of the reaction was monitored by LC/MS. The detector is selected from the group consisting of 220 nm UV detector (FIG. 12A), 263 nm UV detector (FIG. 12B), a diode array (FIG. 12C) and a mass spectrometer (FIG. 12D).

The reaction mixture was filtered through a Celite plug, washed with MeOH, and concentrated under vacuum to afford the compound 12.

The crude product was used for the next step without further purification.

Compound 12 was isolated with quantitative yield.

Step V: DUPA addition

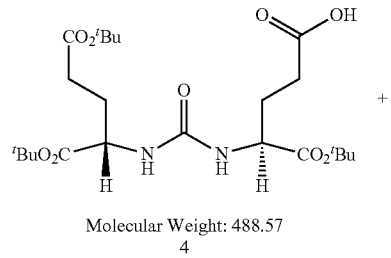

Molecular Weight: 488.57

4

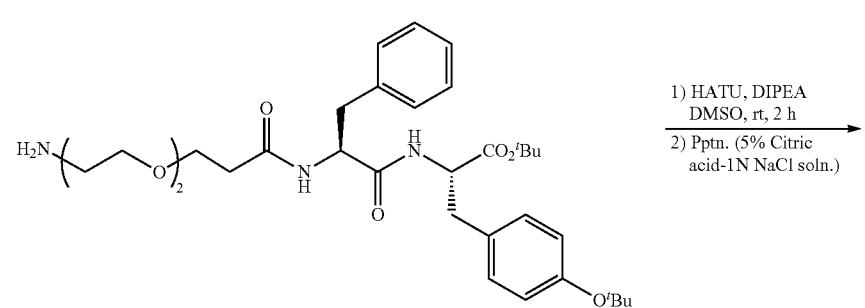

Molecular Weight: 599.76

12

1) HATU, DIPEA DMSO, rt, 2 h
2) Pptn. (5% Citric acid-1N NaCl soln.)

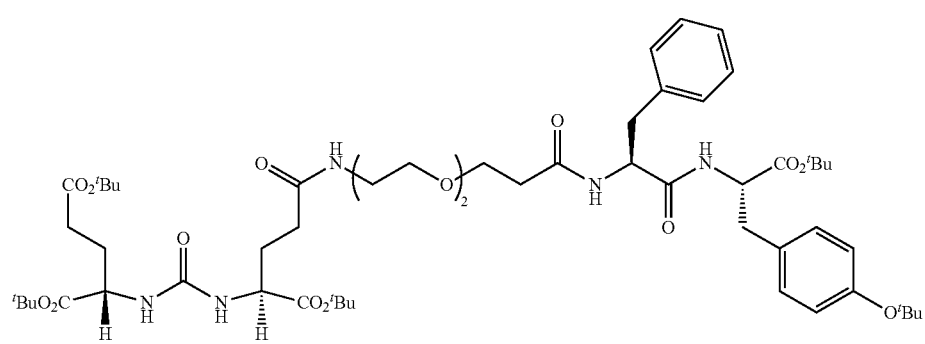

Molecular Weight: 1070.31

13

Reactants for Step V:

| Chemicals | M. W. (g/mol) | Density (g/mL) | Equiv | Qty. (g) | Qty. (mL) | mmol |
|---|---|---|---|---|---|---|
| DUPA—(O$^t$Bu)$_3$—OH (4) | 488.57 | | 1.0 | 0.46 g | | 0.95 |
| NH$_2$—PEG$_2$-Phe-Tyr-(O$^t$Bu)—O$^t$Bu (12) | 599.76 | | 1.05 | 0.60 g | | 1.0 |
| HATU | 380.24 | | 1.05 | 0.38 g | | 1.0 |
| DIPEA | 129.24 | 0.742 | 2.0 | | 0.33 mL | 1.90 |
| DMSO | | | 0.33M | | 3 mL | |

A 50 mL round bottom flask was charged with a stir bar, reactant 4, 2-[3-(1,3-dicarboxypropyl)ureido] pentanedioic acid (DUPA) with tert-butyl protecting groups on three of the four carboxylic acid groups (DUPA-(O$^t$Bu)$_3$-OH [0.46 g, 0.95 mmol, 1 equiv.], compound 12 (NH$_2$-PEG$_2$-Phe-Tyr-(O$^t$Bu)-O$^t$Bu [0.60 g, 1.0 mmol, 1.05 equiv.] and HATU (0.38 g, 1.0 mmol, 1.05 equiv.). DMSO (3 mL) was then added to the reaction flask under argon.

Figure 13A:
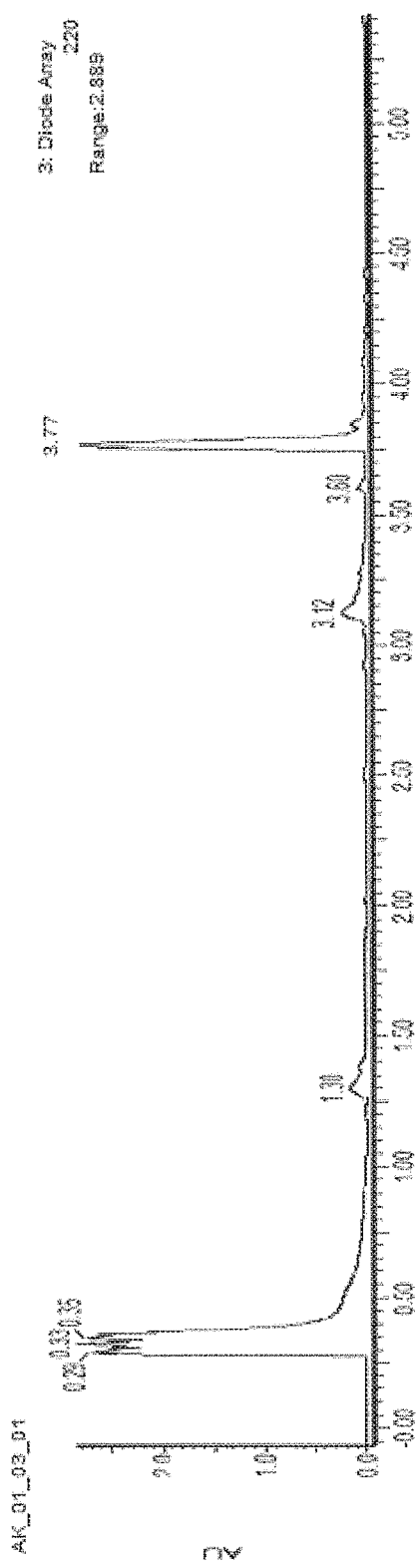
FIG. 13A illustrates the LC/MS Chromatogram profile of the reaction mixture at 1 hour time interval monitoring of the progress of the reaction up to four hours.
Figure 13B:
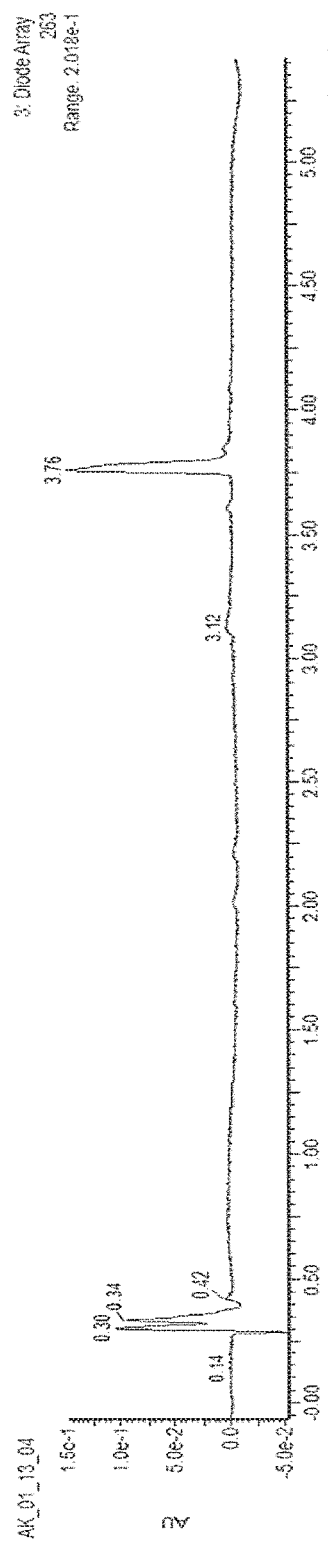
FIG. 13B shows the LC/MS Chromatogram profile of the reaction mixture at 2 hour time interval monitoring of the progress of the reaction up to four hours.
Figure 13C:
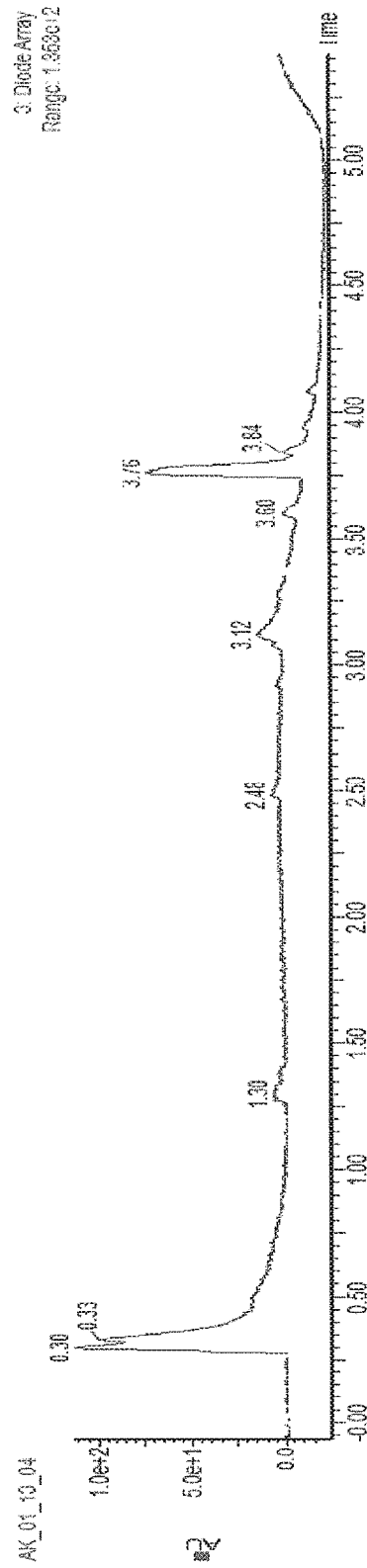
FIG. 13C depicts the LC/MS Chromatogram profile of the reaction mixture at 3 hour time interval monitoring of the progress of the reaction up to four hours.
Figure 13D:
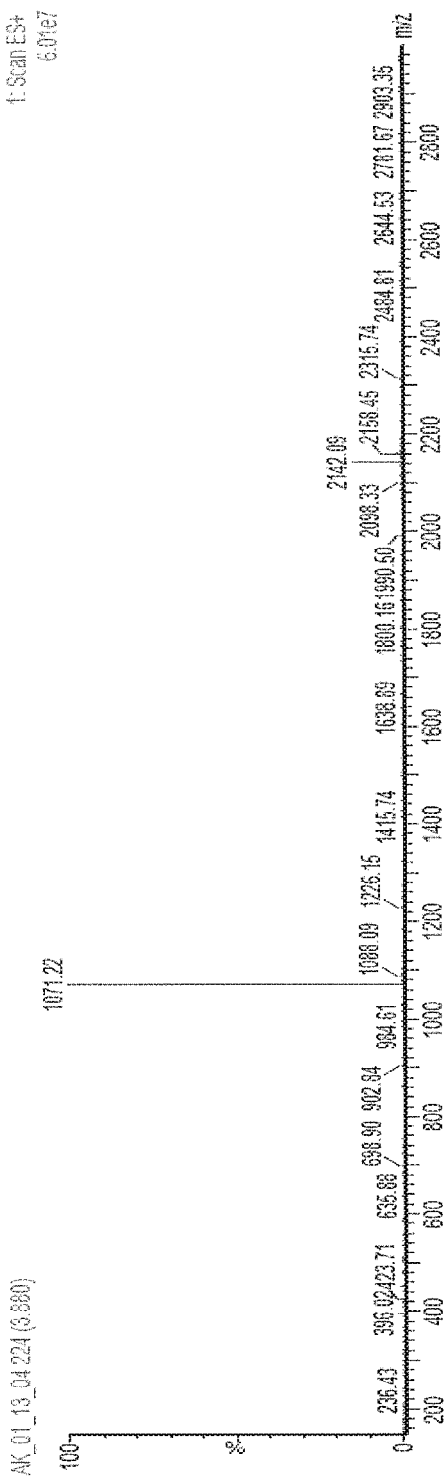
FIG. 13D illustrates the LC/MS Chromatogram profile of the reaction mixture at 4 hour time interval monitoring of the progress of the reaction up to four hours.

DIPEA (0.33 mL, 1.9 mmol, 2.0 equiv.) was added slowly to reaction mixture at 23° C., over 5 minutes. The reaction was stirred at 23° C. for 2 hours. The product formation was confirmed by LC/MS. The detector is selected from the group consisting of 220 nm UV detector (FIG. 13A), 263 nm UV detector (FIG. 13B), a diode array (FIG. 13C) and a mass spectrometer (FIG. 13D).

The reaction mixture was added drop wise to a stirred 18 mL of cold 5% citric acid-1 N NaCl solution (prepared by adding 5.85 g of NaCl to 100 mL of 5% Citric acid solution) to form a gummy solid. The residue gum was filtered and was dissolved in ethyl acetate (20 mL) and washed with water (15 mL), followed by brine (15 mL), and dried over anhydrous Na2SO4, filtered and concentrated.

Figure 14A:
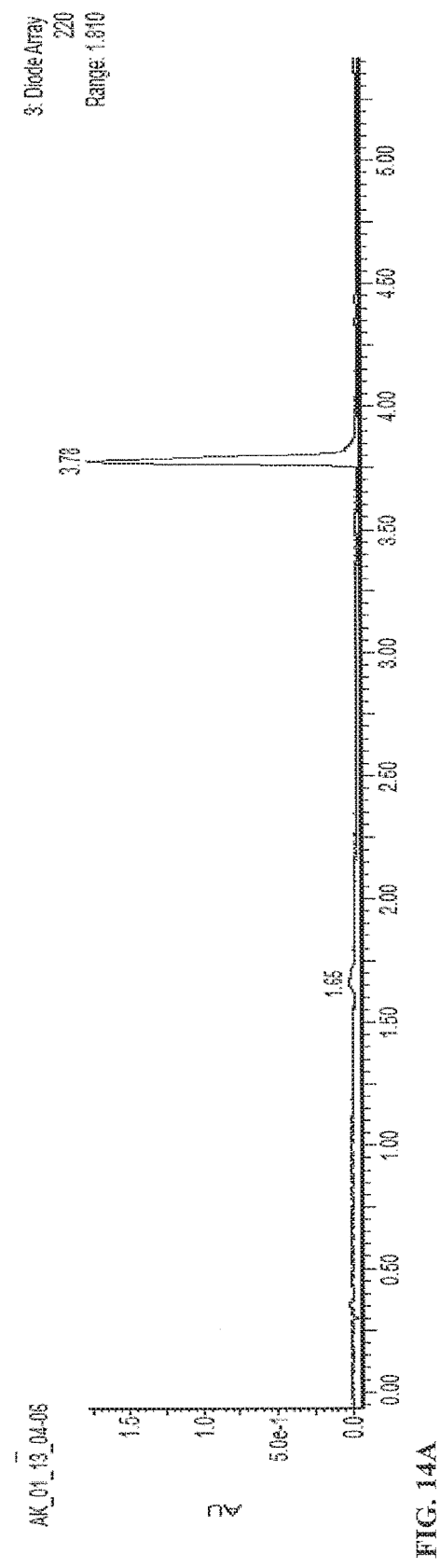
FIG. 14A shows the LC/MS Chromatogram profile of the reaction mixture at 4 h time point at 220 nm UV wavelength. LC/MS method same as in FIG. 7A.
Figure 14B:
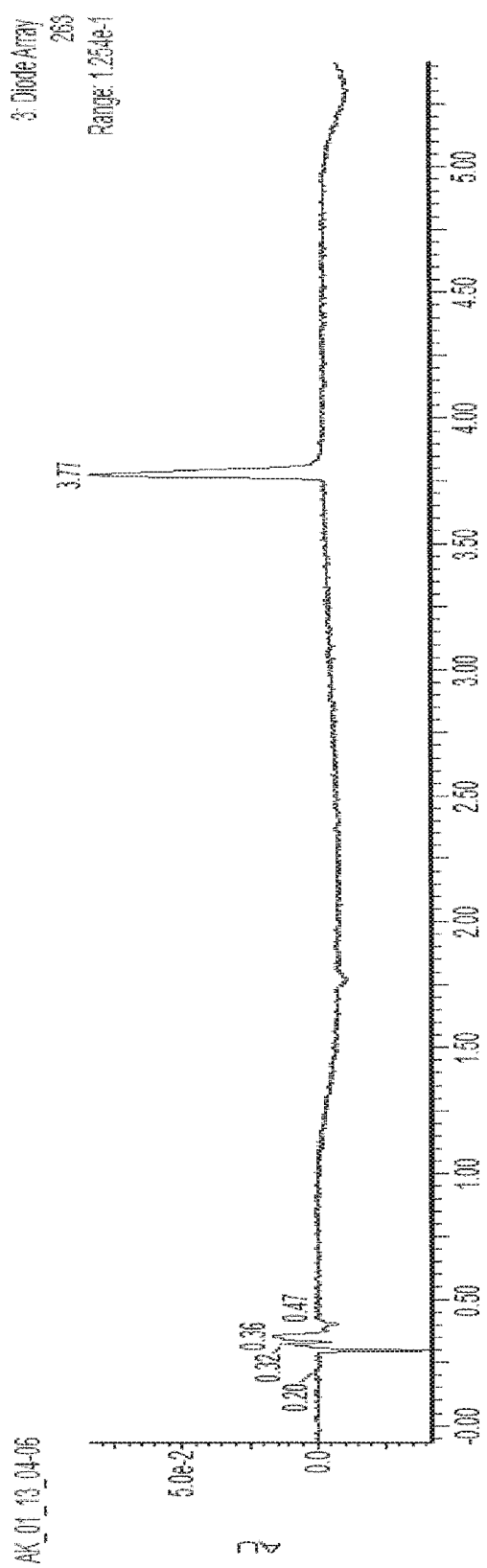
FIG. 14B depicts the LC/MS Chromatogram profile of the reaction mixture at 4 h time point at 490 nm UV wavelength. LC/MS method same as in FIG. 7A.
Figure 14C:
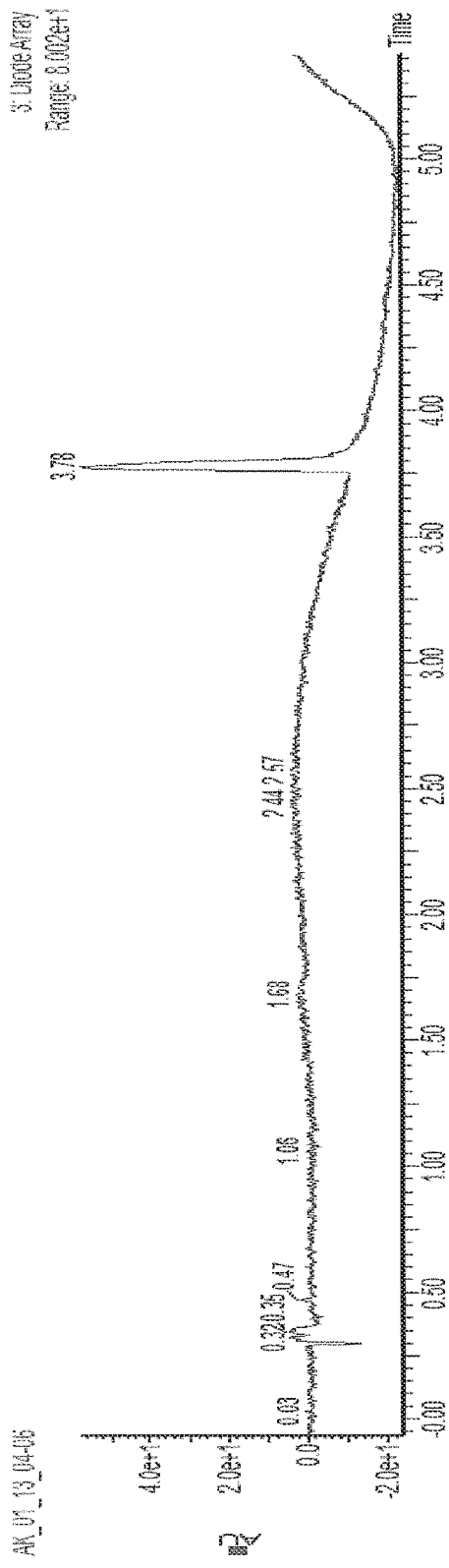
FIG. 14C illustrates the LC/MS Chromatogram profile of the reaction mixture at 4 h time point at 550 nm UV wavelength. LC/MS method same as in FIG. 7A.
Figure 14D:
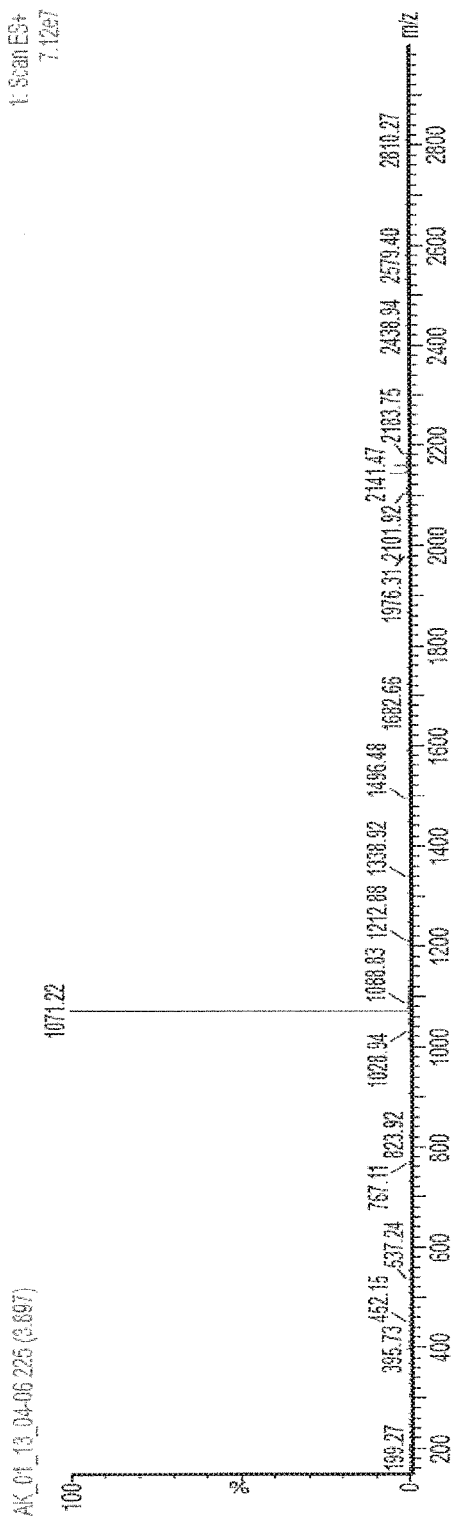
FIG. 14D shows the LC/MS Chromatogram profile of the reaction mixture at 4 h time point at 775 nm UV wavelength. LC/MS method same as in FIG. 7A.

Crude product was purified by silica-gel column chromatography using 60-80% EtOAc in dichloromethane (DCM) followed by 5% methanol in DCM. Purified compound 13 was isolated with 75% yield. The detector is selected from the group consisting of 220 nm UV detector (FIG. 14A), 263 nm UV detector (FIG. 14B), a diode array (FIG. 14C) and a mass spectrometer (FIG. 14D).

Step VI: Tert-Butyl Deprotection

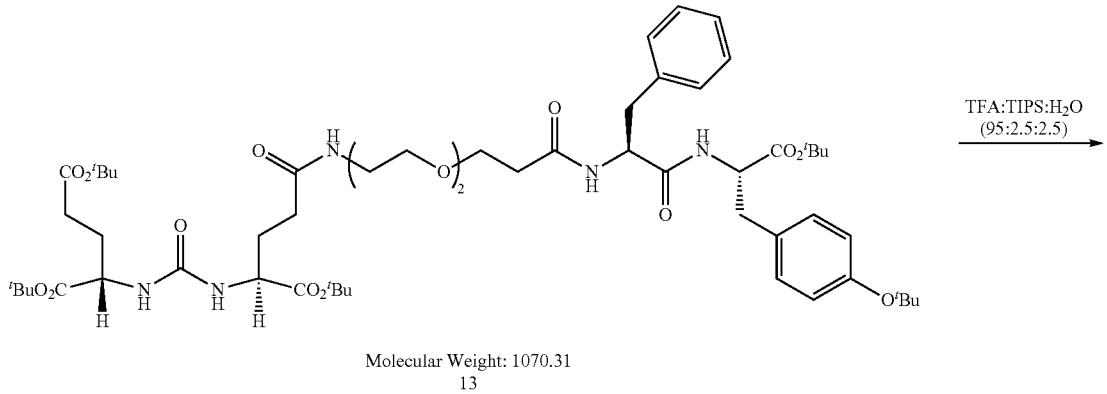

Molecular Weight: 1070.31
13

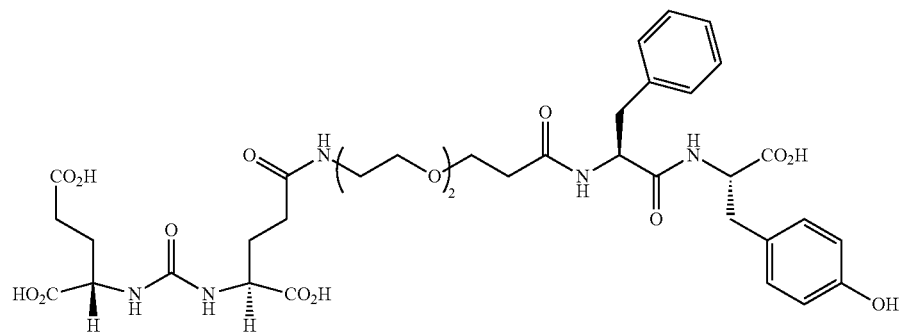

Molecular Weight: 789.78
5

Reactants for Step VI:

| Chemicals | M. W. (g/mol) | Density (g/mL) | Equiv | Qty. (g) | Qty. (mL) | Mmol |
|---|---|---|---|---|---|---|
| DUPA—(O$^t$Bu)$_3$—PEG$_2$-Phe-Tyr-(O$^t$Bu)—O$^t$Bu (13) | 1070.31 | | 1.0 | 0.6 g | | 0.56 |
| TFA:TIPS:H$_2$O 95:2.5:2.5 | | | Excess | | 3.0 mL | |

A 25 mL round bottom flask was charged with a stirring bar and compound 13 (DUPA-(O$^t$Bu)$_3$-PEG$_2$-Phe-Tyr-(O$^t$Bu)-O$^t$Bu [0.50 g, 0.56 mmol, 1 equiv]). A solution of TFA:TIPS:H$_2$O (95:2.5:2.5, 3.0 mL) was added to the reaction flask at room temperature. The reaction mixture was stirred at room temperature for 1 hour and the progress of the reaction was monitored by LC/MS.

Figure 15A:
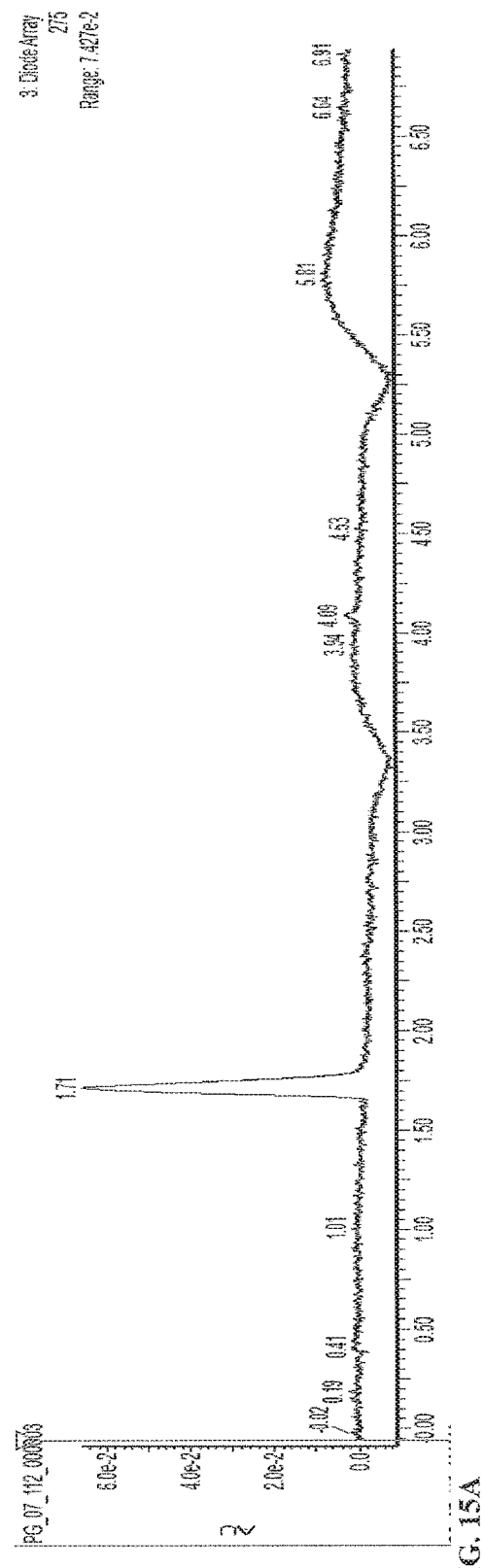
FIG. 15A depicts the LC/MS chromatogram after purification of compound 5: Same conditions of FIG. 7A.
Figure 15B:
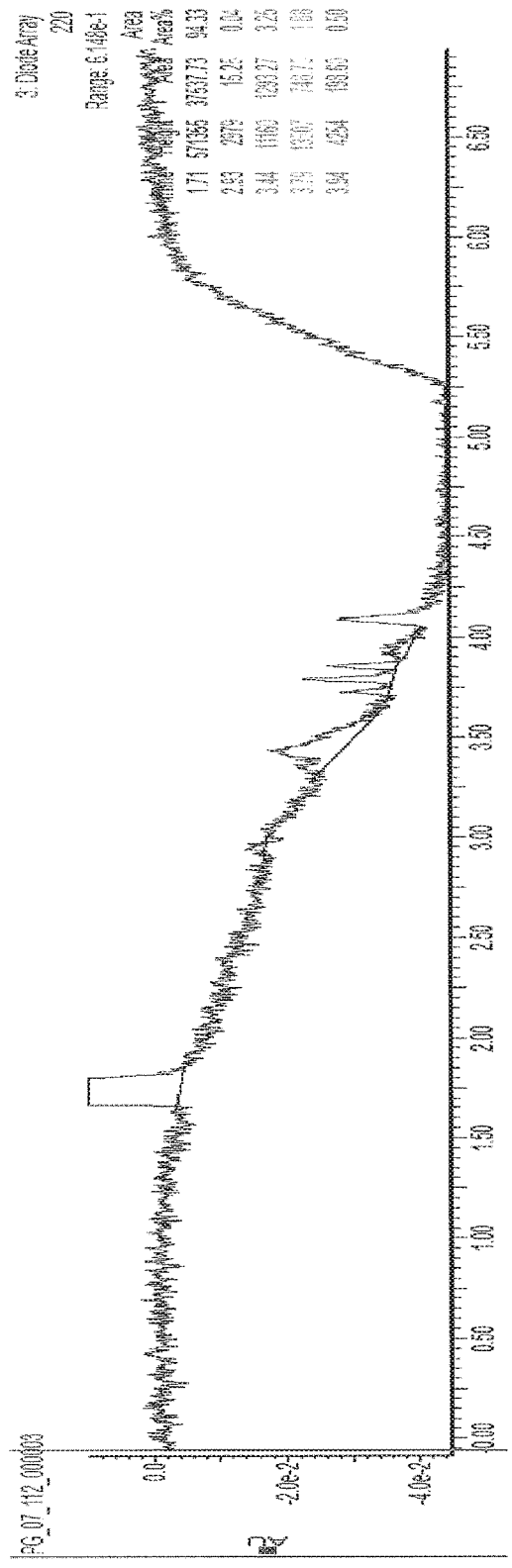
FIG. 15B illustrates the LC/MS chromatogram after purification of compound 5: Same conditions of FIG. 7A.
Figure 15C:
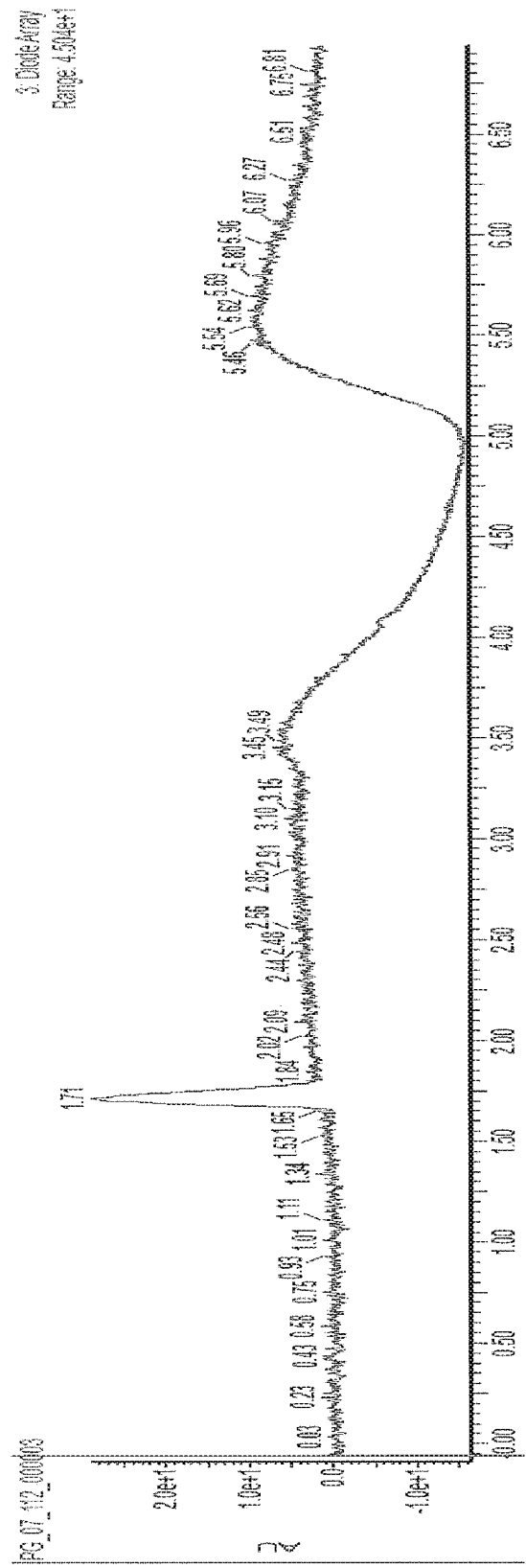
FIG. 15C shows the LC/MS chromatogram after purification of compound 5: Same conditions of FIG. 7C.
Figure 15D:
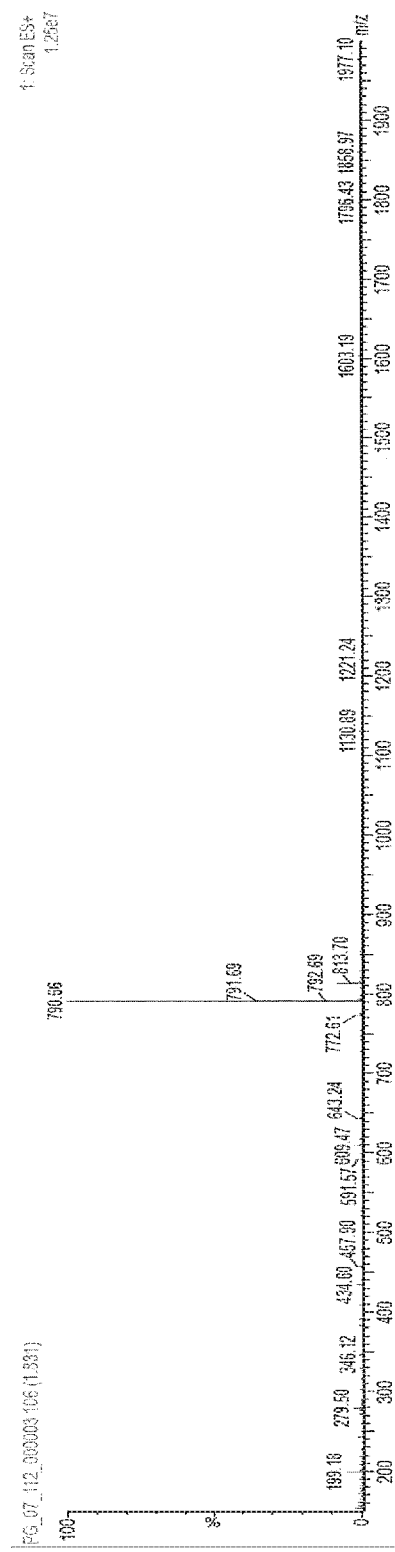
FIG. 15D depicts the mass spectra after purification of compound 5 analyzed using positive mode electrospray ionization mass spectrometry illustrating compound 5+H (m/z 790.6).
Figure 15E:
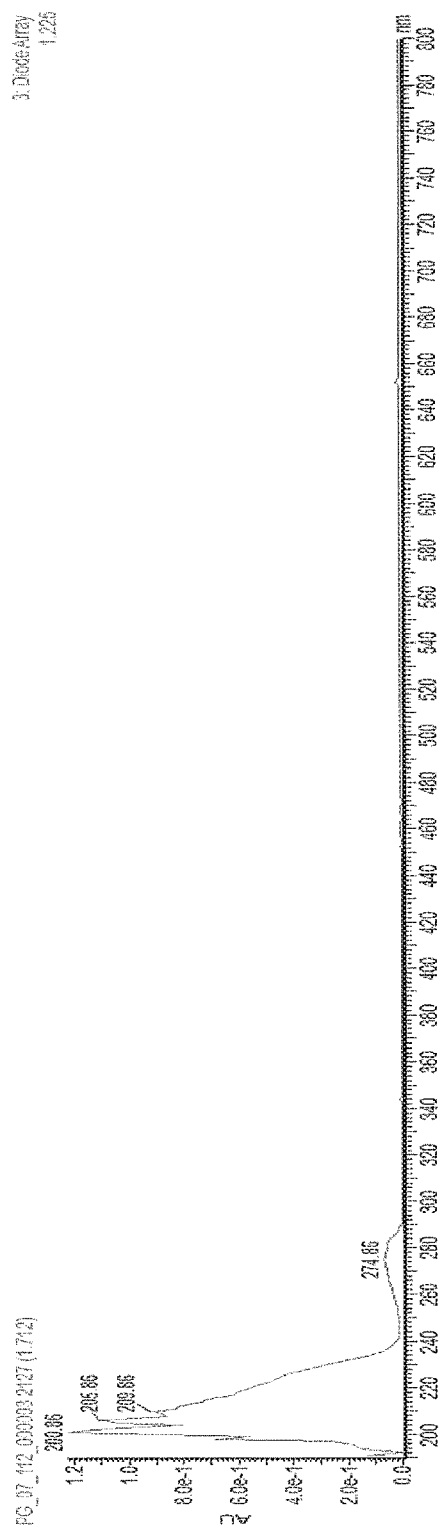
FIG. 15E illustrates the diode array wavelength chart after purification of compound 5.

The reaction mixture was evaporated under vacuum (rotavapor) and the concentrated reaction mixture was added drop wise to stirred cold ether (30 mL) to give white precipitate of compound 5 (DUPA_PEG$_2$_Phe_Tyr-S0456). The precipitated product was centrifuged, washed with cold ether (2×20 mL), and dried under high vacuum to afford compound 5 as a white solid. The compound 10 was isolated in quantitative yield. The detector is selected from the group consisting of 220 nm UV detector (FIG. 15A), 263 nm UV detector (FIG. 15B), a diode array (FIG. 15C) and a mass spectrometer (FIG. 15D).

Purification of compound 5

Sample Preparation:

2 grams of crude compound 5 was suspended in sodium phosphate buffer (pH 7.1, 30 mL) and the pH was adjusted to 7.5 using aqueous saturated NaHCO$_3$ under stirring to form clear pale yellow solution. The solution was filtered through 2 μm filter before injecting into HPLC.

LC/MS method for compound 10 purification: Instrument: Acquity UPLC, Waters Column: BEH C18, 10 μm, 250×50 mm. 40%-98% 10 mM sodium phosphate aqueous at pH 7.1 including monosodium phosphate monohydrate (0.051%)+disodium phosphate heptahydrate (0.169%) with 2%-60% acetonitrile in 45 minutes following the gradient program shown in Table 2. Flow rate is 50 mL/min. Detector is selected from the group consisting of 220 nm UV detector (FIG. 7A), 275 nm UV detector (FIG. 7B), a diode array (FIG. 7C).

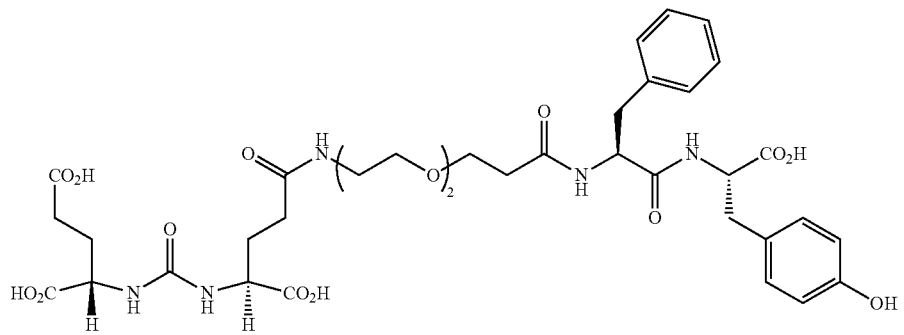

Molecular Weight: 789.78
5

HPLC purification
Na-Phophate buffer
pH 7.1

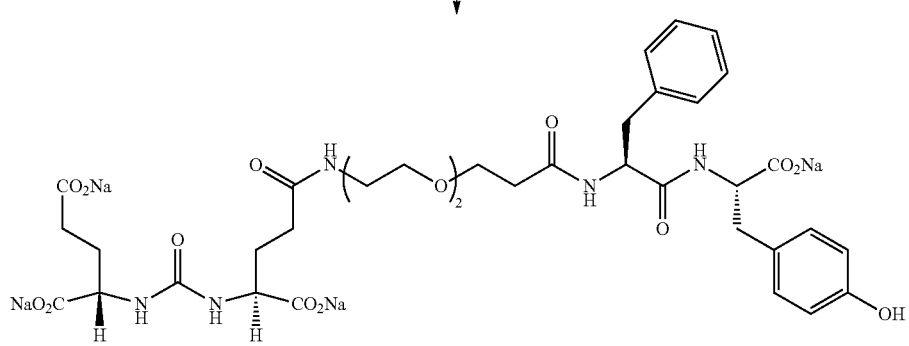

Molecular Weight: 877.71
14

TABLE 2

Eluent A: 10 mM sodium phosphate aqueous at pH 7.1 including monosodium phosphate monohydrate (0.051%) + disodium phosphate heptahydrate (0.169%); Eluent B: acetonitrile:

| Time | Flow rate mL/min | % A | % B |
|---|---|---|---|
| 0 | 50 | 98 | 2 |
| 15 | 50 | 75 | 25 |
| 22 | 50 | 40 | 60 |
| 30 | 50 | 40 | 60 |
| 45 | 50 | 98 | 2 |
| 55 | 50 | 98 | 2 |
| 55.01 | 50 | 98 | 2 |

Desalting method of 14 by HPLC

Figure 16A:
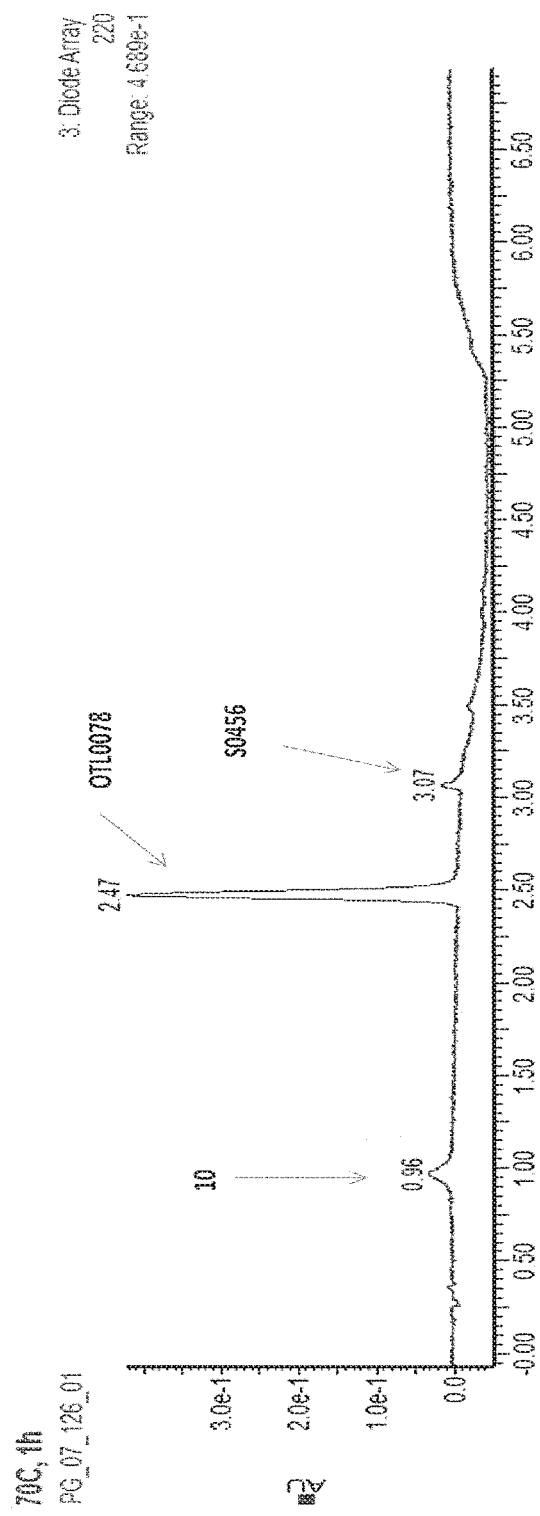
FIG. 16A shows the LC/MS Chromatogram profile of the reaction mixture at 1 hour time interval monitoring of the progress of the reaction at 220 nm UV wavelength. LC/MS method same as in FIG. 7A.
Figure 16B:
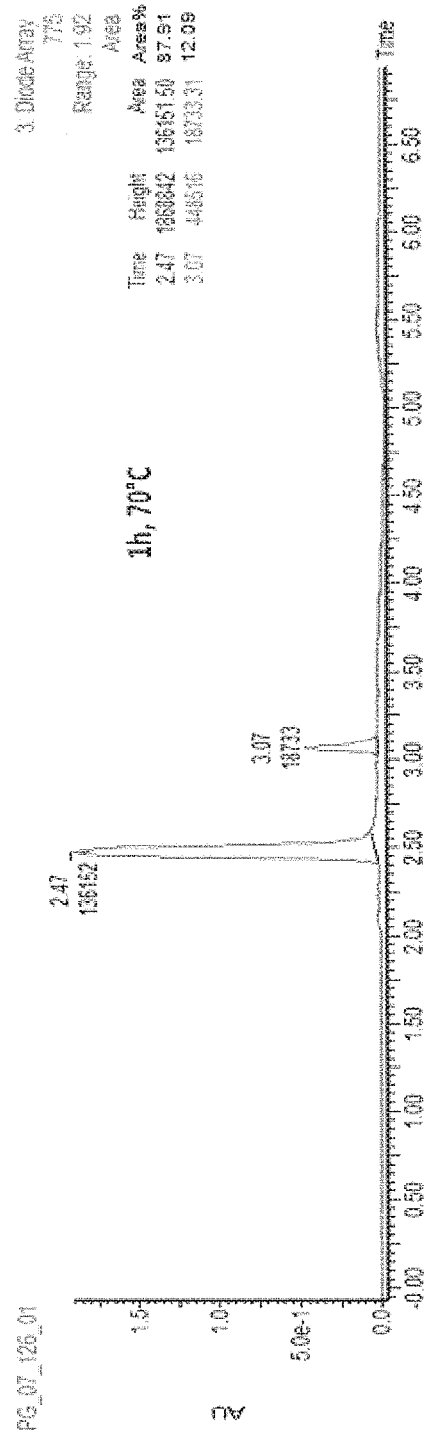
FIG. 16B depicts the LC/MS Chromatogram profile of the reaction mixture at 1 hour time interval monitoring of the progress of the reaction at 775 nm UV wavelength. LC/MS method same as in FIG. 7A.
Figure 16C:
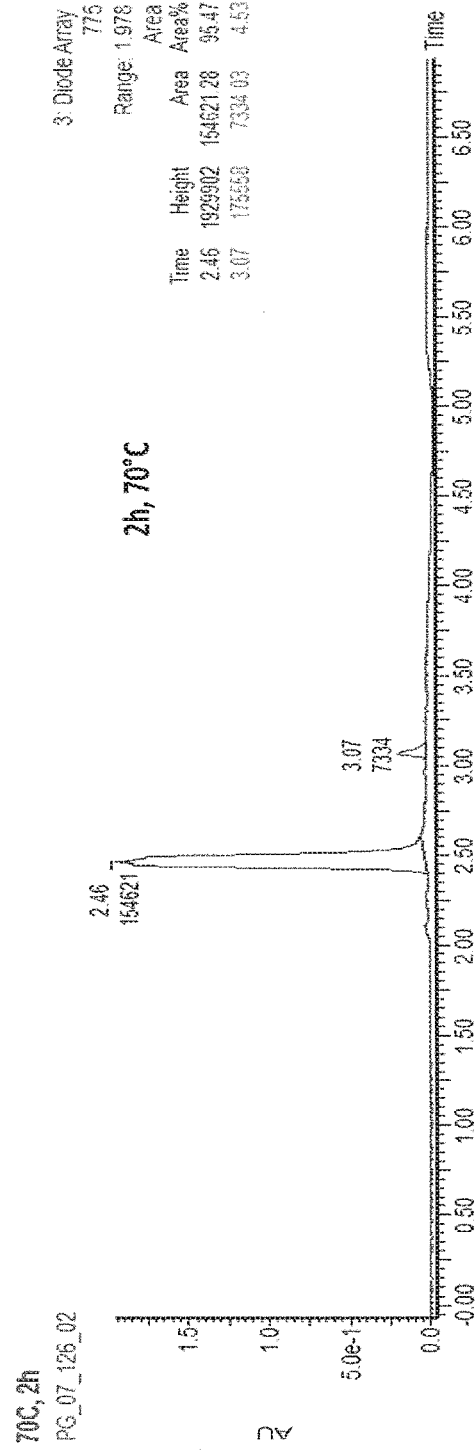
FIG. 16C illustrates the LC/MS Chromatogram profile of the reaction mixture at 2 hour time interval monitoring of the progress of the reaction at 775 nm UV wavelength. LC/MS method same as in FIG. 7A.
Figure 16D:
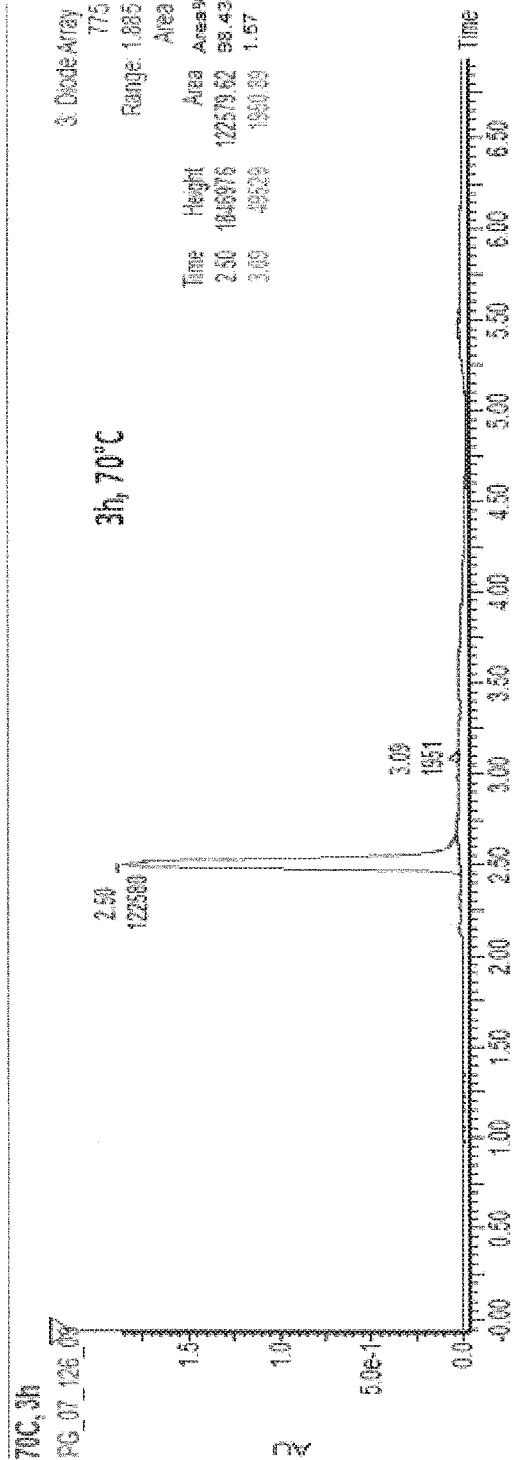
FIG. 16D shows the LC/MS Chromatogram profile of the reaction mixture at 3 hour time interval monitoring of the progress of the reaction at 775 nm UV wavelength. LC/MS method same as in FIG. 7A.
Figure 16E:
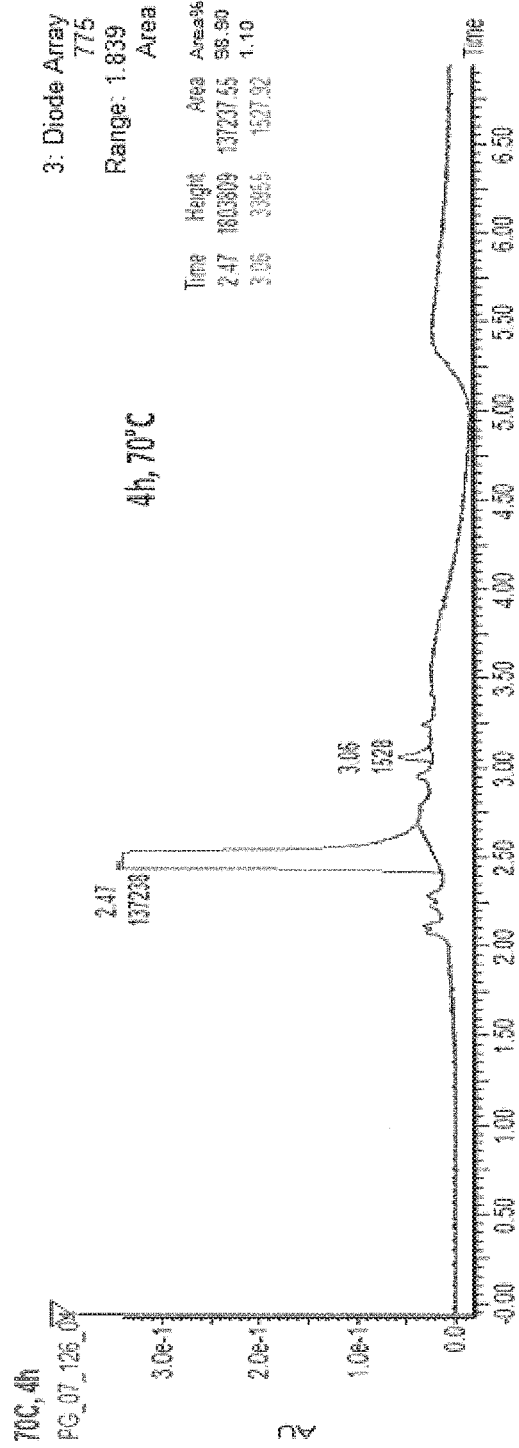
FIG. 16E depicts the LC/MS Chromatogram profile of the reaction mixture at 4 hour time interval monitoring of the progress of the reaction at 775 nm UV wavelength. LC/MS method same as in FIG. 7A.

LC/MS method for compound 10 purification: Instrument: Acquity UPLC, Waters Column: BEH C18, 10 μm, 250×50 mm. 10%-99% water with 1%-90% acetonitrile in 45 minutes following the gradient program shown in Table 3. Flow rate is 50 mL/min. Detector is selected from the group consisting of 220 nm UV detector (FIG. 13A), 275 nm UV detector (FIG. 16B), a diode array (FIG. 16C), a mass spectrometer (FIG. 16D) and a diode array (FIG. 16E).

TABLE 3

Eluent A: water; Eluent B: acetonitrile:

| Time | Flow rate mL/min | % A | % B |
|---|---|---|---|
| 0 | 50 | 99 | 1 |
| 15 | 50 | 99 | 1 |
| 25 | 50 | 10 | 90 |
| 28 | 50 | 10 | 90 |
| 35 | 50 | 99 | 1 |
| 45 | 50 | 99 | 1 |
| 45.01 | 50 | 99 | 1 |

The combined pure fractions of 14 were evaporated under vacuum (on rotavapor @37° C. water bath temperature) to evaporate acetonitrile and to bring the total volume to 50 mL and injected on HPLC to remove phosphate salts. The pure fractions were concentrated under vacuum (on rotavapor @37° C. water bath temperature) and lyophilized after freezing to afford white solid of compound 10.

Step VII: S0456 Addition

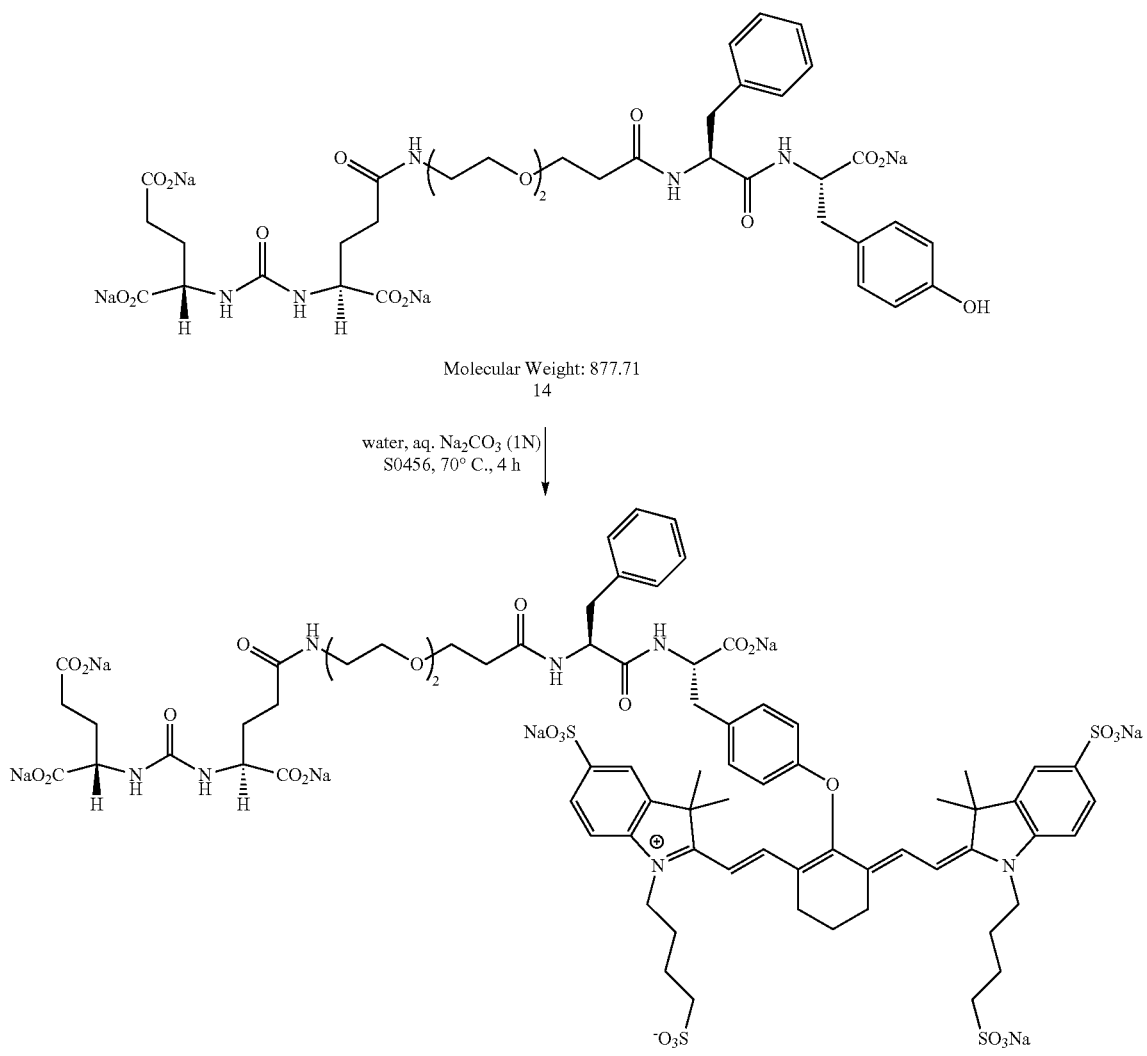

Molecular Weight: 877.71
14 water, aq. Na₂CO₃ (1N)
S0456, 70° C., 4 h

Molecular Weight: 1794.69
1

Reactants for Step VII:

| Chemicals | M. W. (g/mole) | Density (g/mL) | Equiv | Qty. (g) | Qty. (mL) | mmol |
|---|---|---|---|---|---|---|
| DUPA_PEG$_2$_Phe_Tyr-OH (14) | 877.71 | | 1.00 | 5.00 g | | 5.697 |
| S0456 (sodium salt) | 953.44 | | 1.00 | 5.431 g | | 5.697 |
| Na$_2$CO$_3$ (aq. 1.0M) | 10598 | | 1.10 | | 6.27 mL | 6.266 |
| H$_2$O | | 1.0 | [0.1M]* | | 50.73 mL | |
| Silica | 200-400 mesh, 40-70 μm | | | 60 + 60 g | | |
| Acetone | | | | | 500 mL | |
| 10% Water + 90% Acetone | | | | | 15 L | |
| 10% water + 90% Acetonitrile | | | | | 12 L | |
| 30% water + 70% Acetonitrile | | | | | 2 L | |

*1.0M Na2CO3 aq. solution + water, together makes 0.1M concentration with respect to 14.

A 200 mL round bottom flask was charged with a stirring bar and compound 14 (DUPA_PEG2_Phe_Tyr-OH) [5.0 g, 5.697 mmol, 1 equiv]). Water (50.73 mL) was added to the round bottom flask and stirred the suspension to give a clear colorless solution, solution VII-A.

A freshly prepared solution of aq. 1.0 M Na2CO3 (6.27 mL, 6.697 mmol, 1.1 equiv) was added to solution VII-A slowly at 23° C. over 5 min to reach pH 10.4. The pH of the solution was recorded using pH meter.

Sodium salt of S0456 (5.431 g, 5.697 mmol, 1.0 equiv) was added to solution VII-B and the content was stirred until a uniform green suspension is formed, suspension VII-C.

The flask containing suspension VII-C was assembled with a condenser, immersed in a 70° C. oil bath, and stirred for 4 hours. The reaction was monitored by LC/MS at every hour until the conversion was >98% @ 775 nm (formation of OTL0078 compared to consumption of S0456).

The reaction mixture was cooled to room temperature using a water bath.

A 1 L beaker was charged with 60 g silica and the reaction mixture from step 5 was transferred into the silica. The reaction mixture was mixed using a spatula till the silica gets a uniform dark green.

Acetone (250 mL) was added the dark green silica and agitated with the spatula. The silica was allowed to settle and the supernatant was decanted. This step was repeated with another 250 mL of acetone followed by 250 ml of 10% Water+90% Acetone mixture.

A column was packed using 60 g silica in acetone (600 mL) and pressurized till the acetone level was just above the silica. The green silica mixture (~60 g) from the step 7 was added on top of the packed silica bed by suspending it in 10% Water+90% Acetone mixture. The green silica bed was topped with some sand to prevent damage to the silica bed. The column bed (60 g of silica and ~60 g of silica+green reaction mixture from the Step 7) was washed with 10% Water+90% Acetone mixture (15 L) followed by, 10% water+90% Acetonitrile (12 L).

Then column was washed with 30% water+70% acetonitrile (2 L) till all the green material is eluted from the silica column and collected into fractions. After evaluating the purity of the fractions by LC/MS, the pure fractions were combined together. The combined fractions were filtered through 0.2 micron filter to remove trace silica particles (if present) and concentrated under vacuum (on rotavapor @37° C. water bath temperature) to remove acetonitrile.

Figure 17:
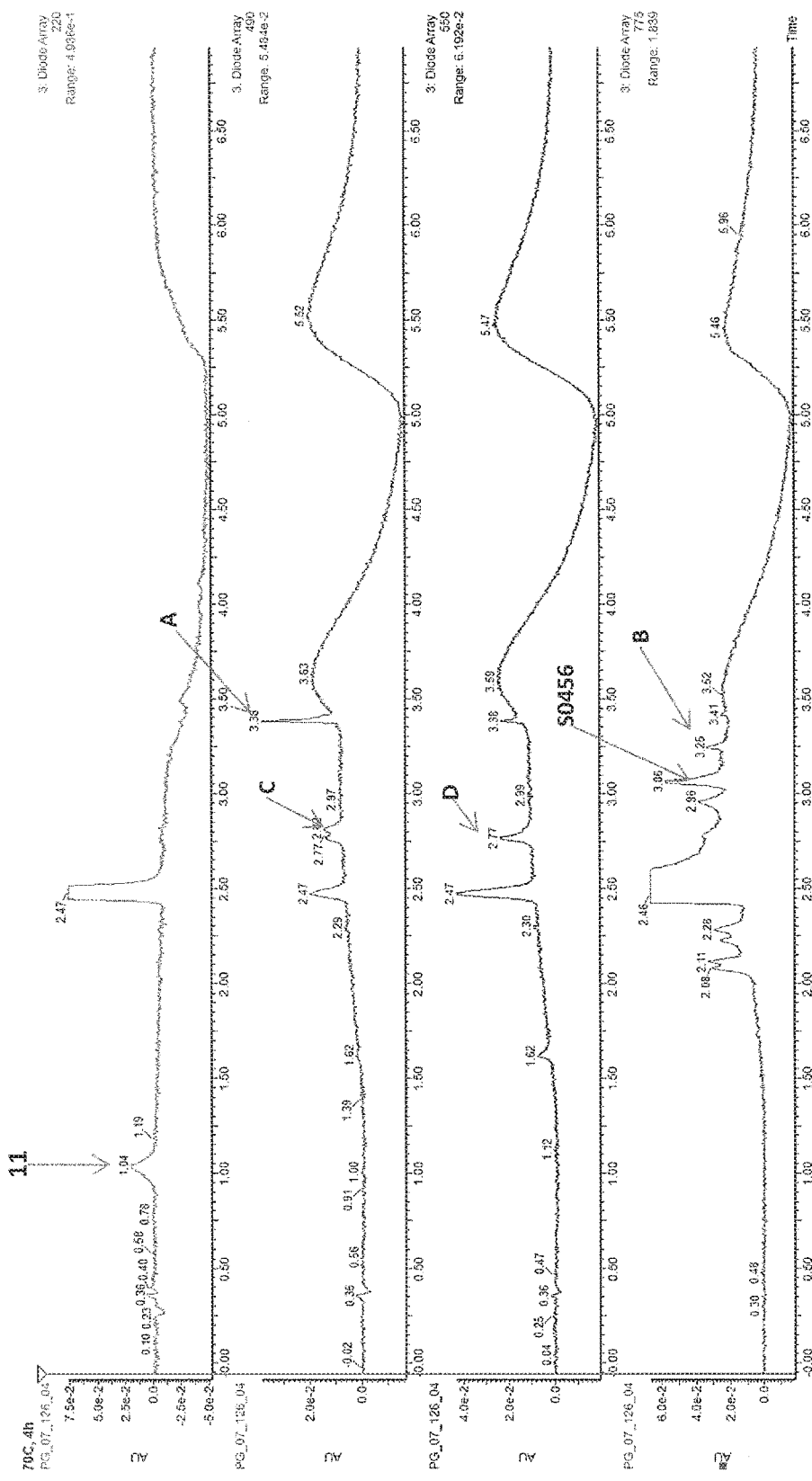
FIG. 17 illustrates the LC/MS Chromatogram profile of the reaction mixture at 4 h time point at 220 nm UV wavelength, the LC/MS Chromatogram profile of the reaction mixture at 4 h time point at 490 nm UV wavelength; the LC/MS Chromatogram profile of the reaction mixture at 4 h time point at 550 nm UV wavelength; and the LC/MS Chromatogram profile of the reaction mixture at 4 h time point at 775 nm UV wavelength. LC/MS method same as in FIG. 7A.
Figure 18A:
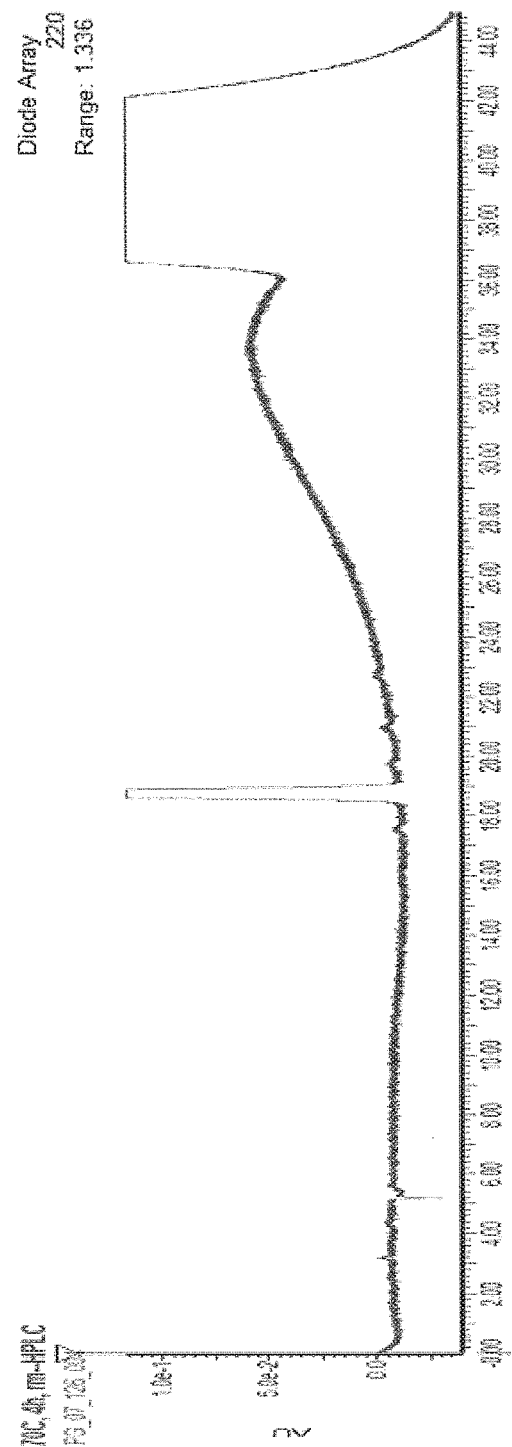
FIG. 18A shows the UPLC/MS chromatogram profiles of the reaction mixture at 4 hour time point at 220 nm UV wavelength.
Figure 18B:
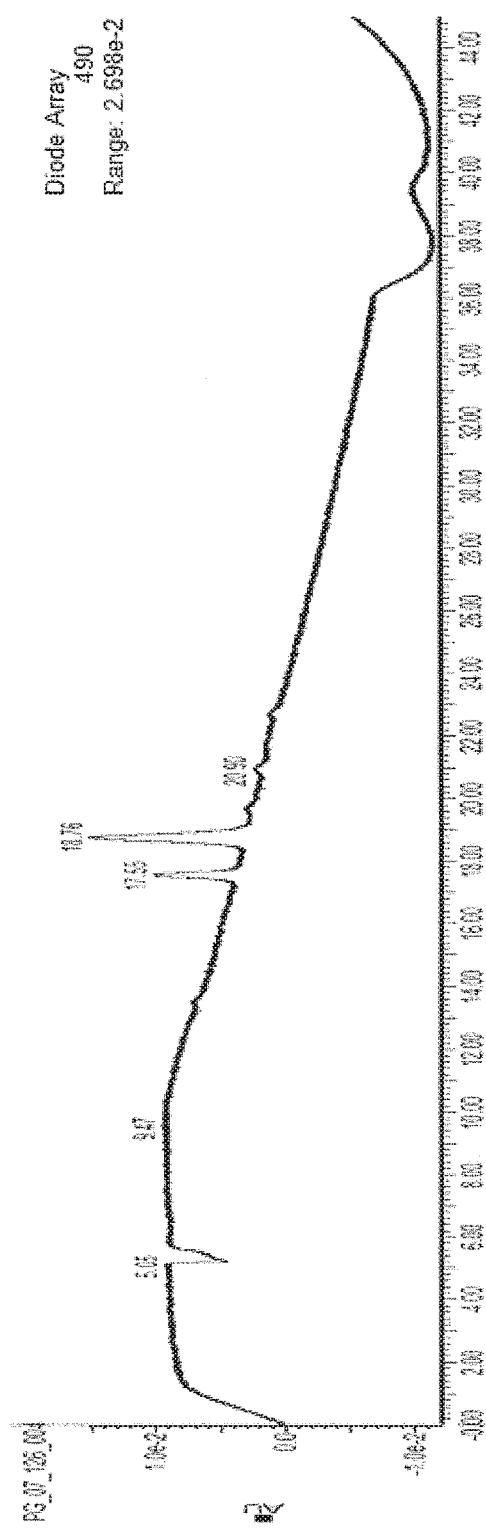
FIG. 18B depicts the UPLC/MS chromatogram profiles of the reaction mixture at 4 hour time point at 490 nm UV wavelength.
Figure 18C:
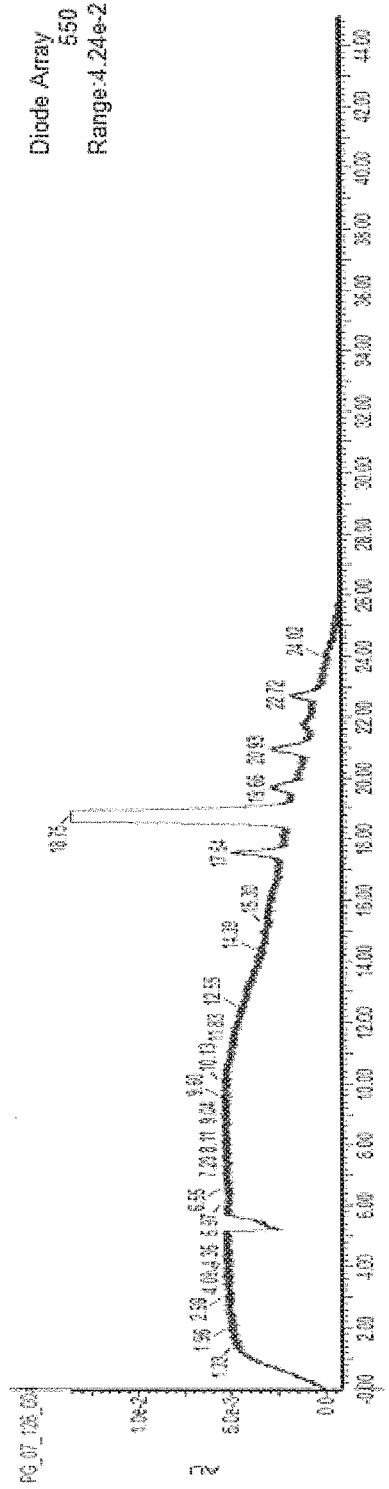
FIG. 18C illustrates the UPLC/MS chromatogram profiles of the reaction mixture at 4 hour time point at 550 nm UV wavelength.
Figure 18D:
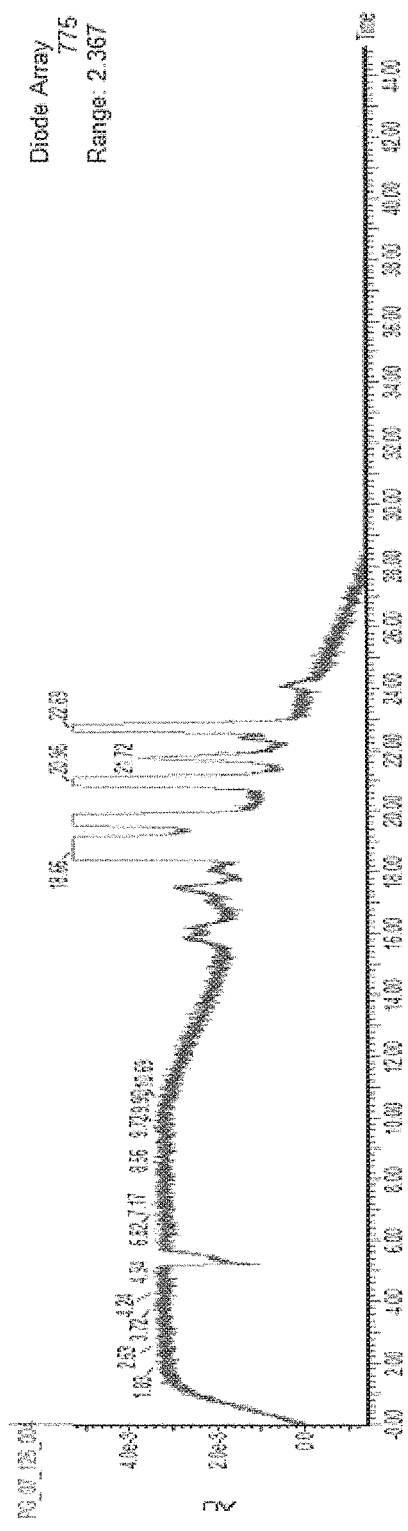
FIG. 18D shows the UPLC/MS chromatogram profiles of the reaction mixture at 4 hour time point at 775 nm UV wavelength.
Figure 19A:
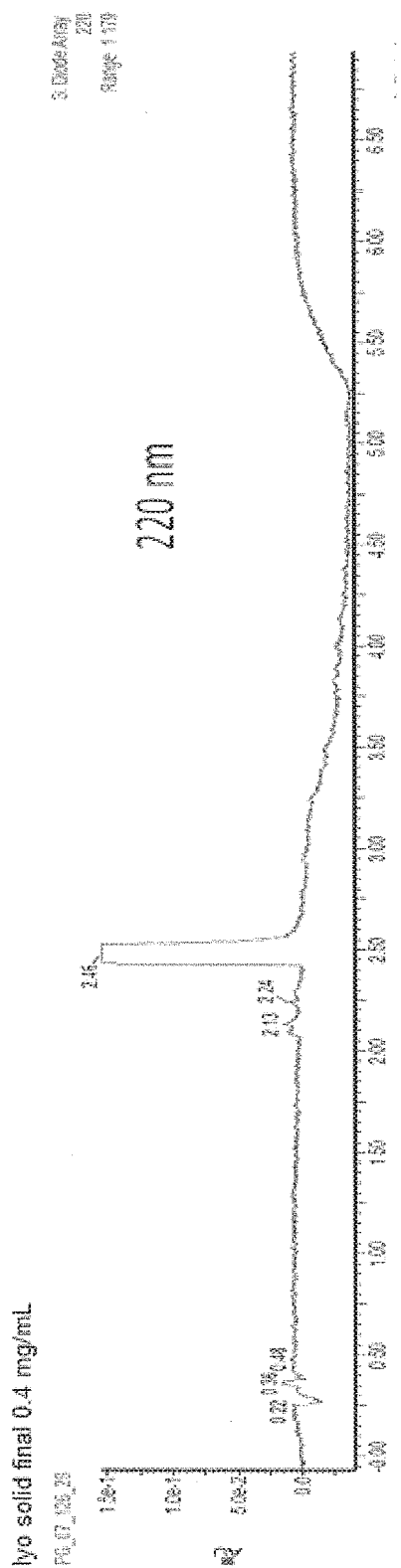
FIG. 19A depicts the LC/MS Chromatogram profiles of compound 1: OTL78 at 220 nm UV wavelength after silica column purification and lyophilization.
Figure 19B:
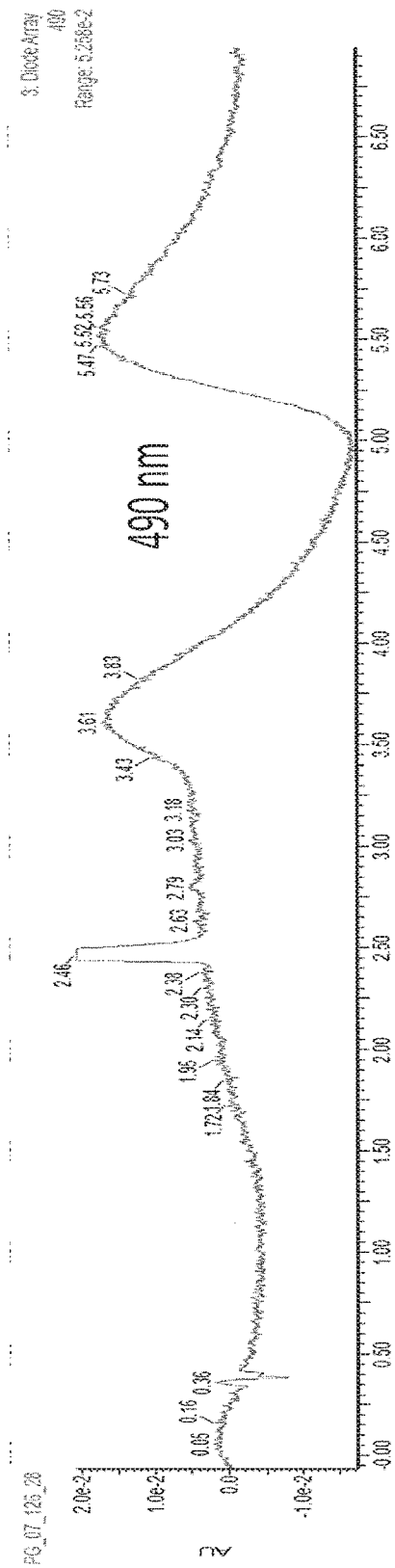
FIG. 19B illustrates the LC/MS Chromatogram profiles of compound 1: OTL78 at 490 nm UV wavelength after silica column purification and lyophilization.
Figure 19C:
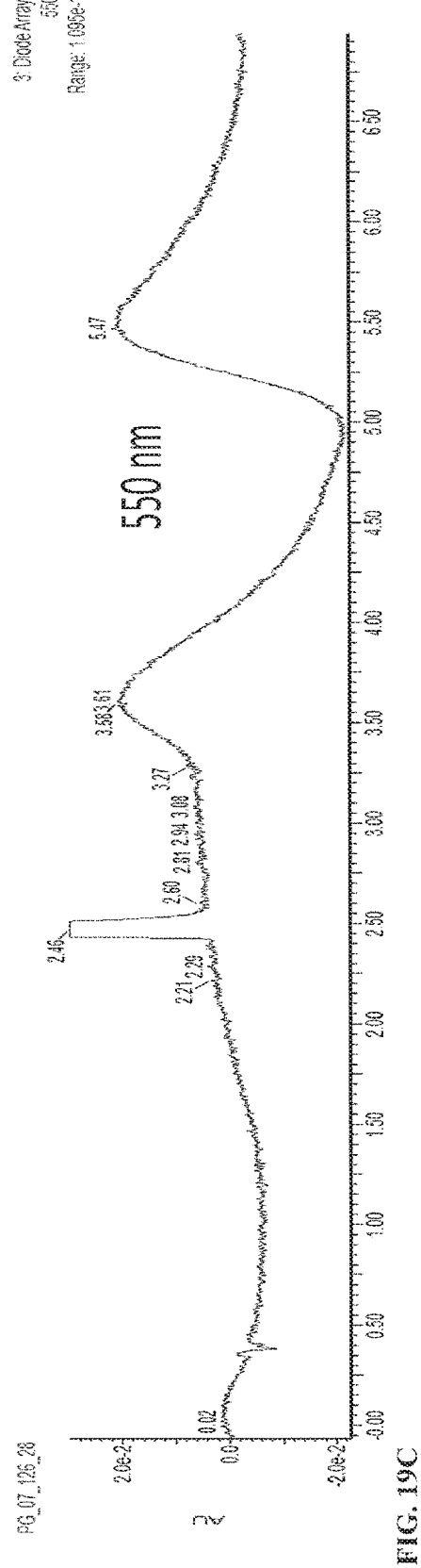
FIG. 19C shows the LC/MS Chromatogram profiles of compound 1: OTL78 at 550 nm UV wavelength after silica column purification and lyophilization.
Figure 19D:
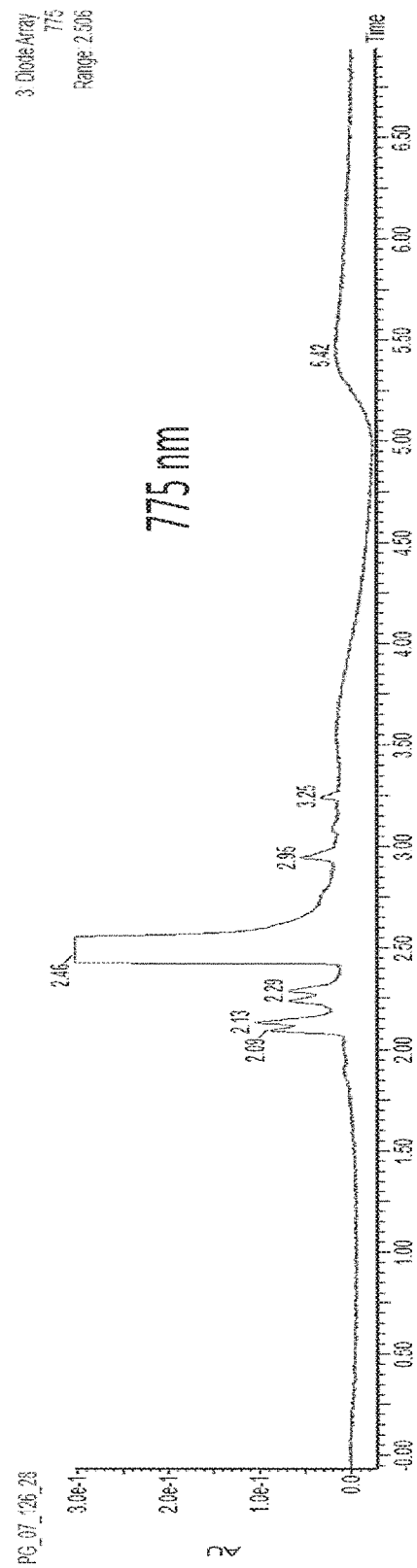
FIG. 19D depicts the LC/MS Chromatogram profiles of compound 1: OTL78 at 775 nm UV wavelength after silica column purification and lyophilization.
Figure 20A:
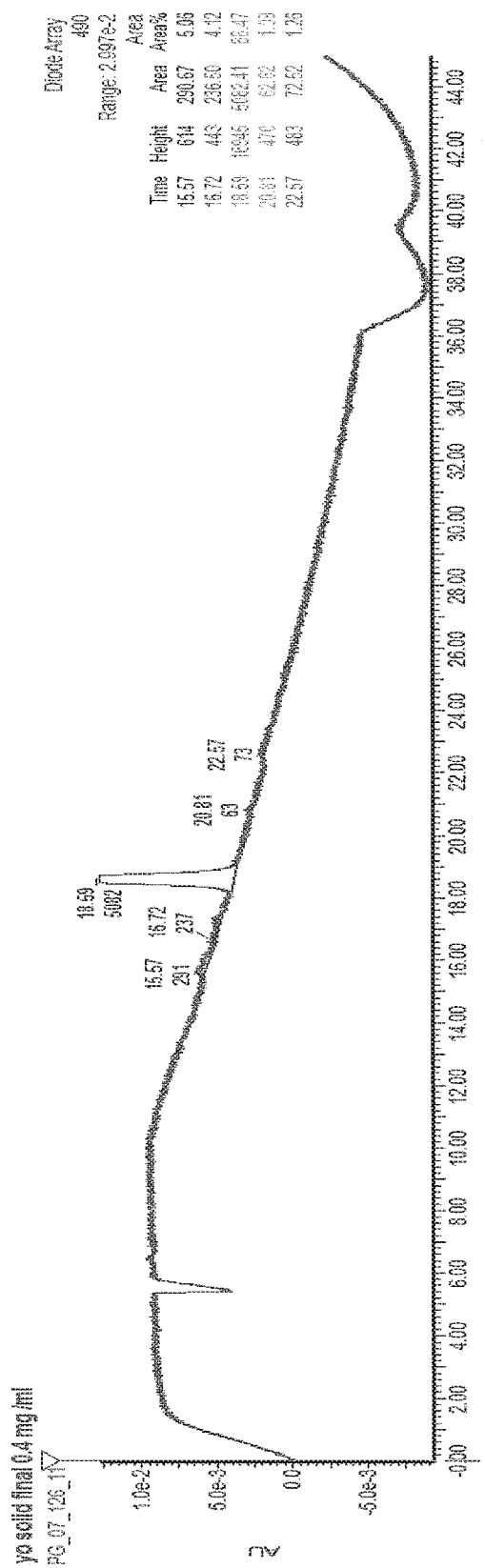
FIG. 20A illustrates the UPLC with HPLC column Chromatogram profiles of compound 1: OTL78 at 490 nm UV wavelength after silica column purification and lyophilization.
Figure 20B:
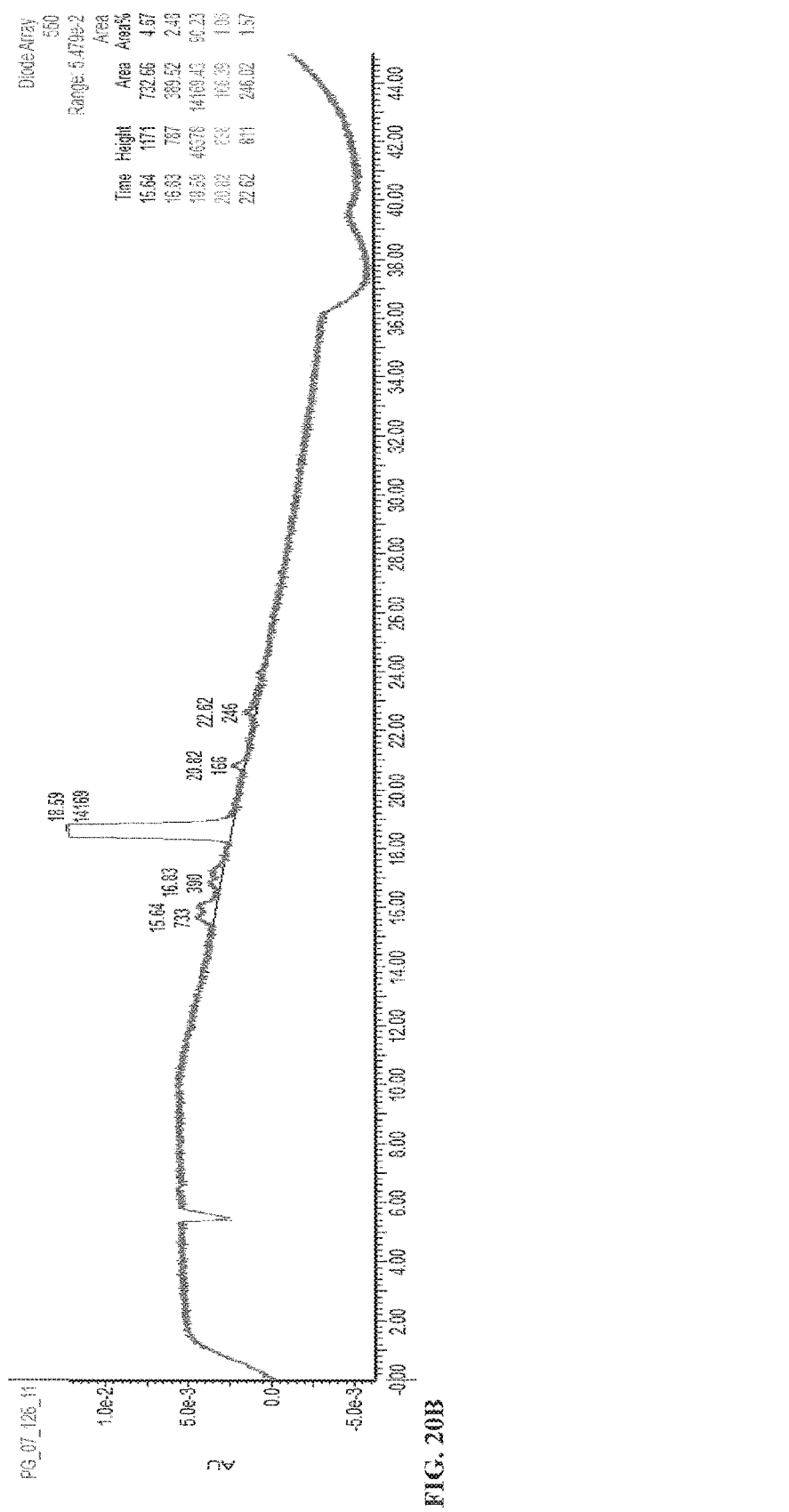
FIG. 20B shows the UPLC with HPLC column Chromatogram profiles of compound 1: OTL78 at 550 nm UV wavelength after silica column purification and lyophilization.
Figure 20C:
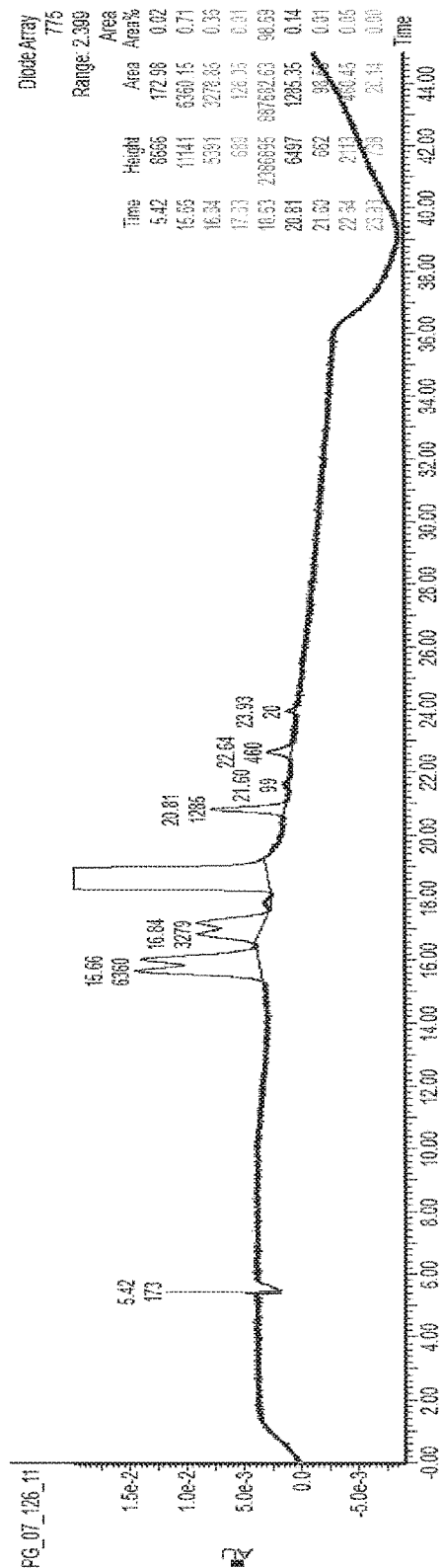
FIG. 20C depicts the UPLC with HPLC column Chromatogram profiles of compound 1: OTL78 at 775 nm UV wavelength after silica column purification and lyophilization.
Figure 20D:
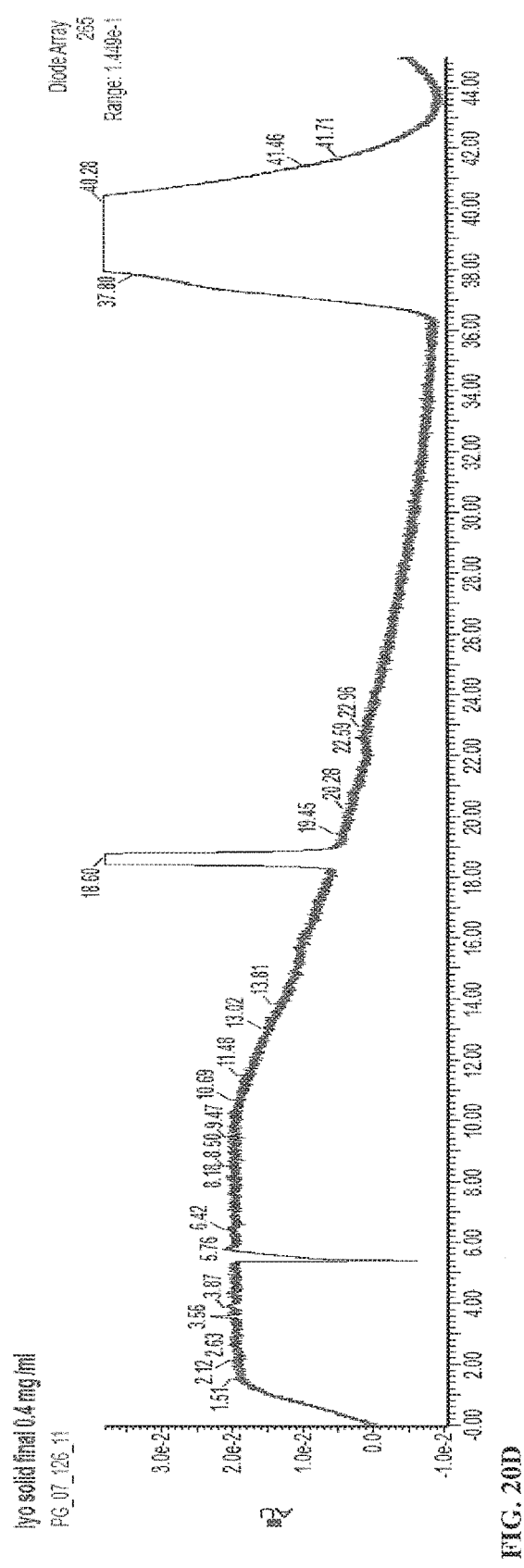
FIG. 20D illustrates the UPLC with HPLC column Chromatogram profiles of compound 1: OTL78 at 265 nm UV wavelength after silica column purification and lyophilization.

After freezing aqueous residue it was subjected to lyophilization for 48 hours. Detector is selected from the group consisting of 220 nm diode array (FIG. 17A), 490 nm diode array (FIG. 17B), 550 nm diode array (FIG. 17C), 775 nm diode array (FIG. 17D).

After reevaluating the purity of the material using LC/MS, the dried green solid was stored in amber colored bottles.

Purified compound 1 (OTL78) was isolated with 72.3% yield (7.4 g).

Figure 25:
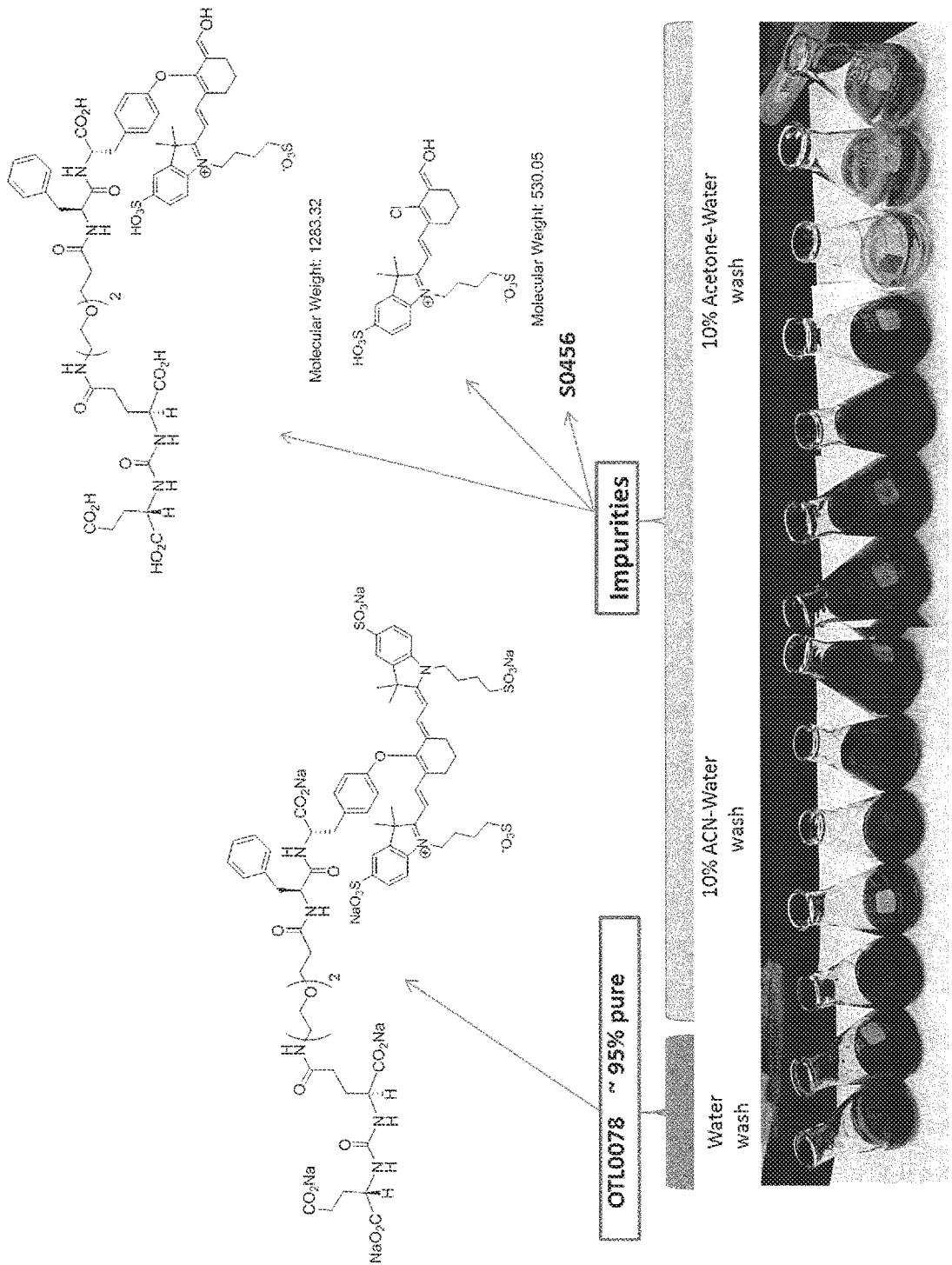
FIG. 25 shows the fractions of silica gel column of crude 1: OTL78 purification following LC/MS conditions of FIG. 4A.

Table 4 includes possible impurities:

| FIG. 25 Peak Label/Retention time (min) | Probable structure |
|---|---|
| A/3.38 | 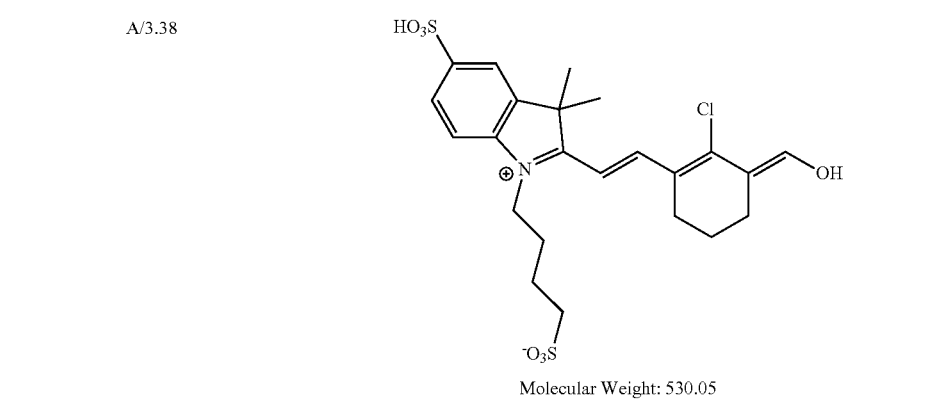 Molecular Weight: 530.05 |
| B/3.25 | Unknown |

| FIG. 25 Peak Label/Retention time (min) | Probable structure |
|---|---|
| C/2.82 | 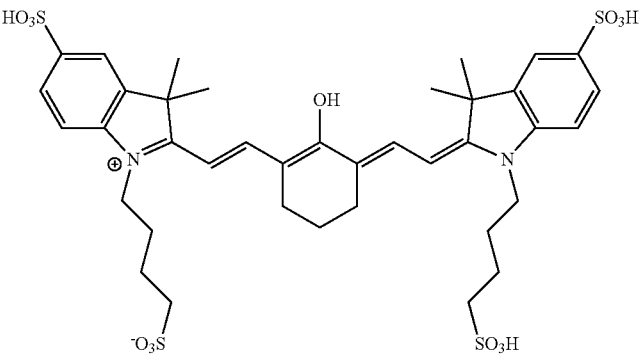 Molecular Weight: 869.05 |
| 1.04 3.06 | compound 11 S0456 |

UPLC/MS method with HPLC column for compound 1 purification: Instrument: Acquity UPLC, Waters. Column: Silica Chrome® PPF nec, 3 μm, 4.6×150 mm. 30%-97% 10 mM sodium phosphate aqueous at pH 7.1 including monosodium phosphate monohydrate (0.051%)+disodium phosphate heptahydrate (0.169%) with 3%-70% acetonitrile in 45 minutes following the gradient program shown in Table 5. Flow rate is 0.4 mL/min. Detector is selected from the group consisting of 220 nm UV detector (FIG. 7A), 275 nm UV detector (FIG. 7B), a diode array (FIG. 7C).

TABLE 5

Eluent A: 10 mM sodium phosphate aqueous at pH 7.1 including monosodium phosphate monohydrate (0.051%) + disodium phosphate heptahydrate (0.169%); Eluent B: acetonitrile:

| Time | Flow rate mL/min | % A | % B |
|---|---|---|---|
| 0 | 0.45 | 97 | 3 |
| 30 | 0.45 | 70 | 30 |
| 35 | 0.45 | 30 | 70 |
| 40 | 0.45 | 97 | 3 |
| 45 | 0.45 | 97 | 3 |
| 45.01 | 0.45 | 97 | 3 |

Figure 21A:
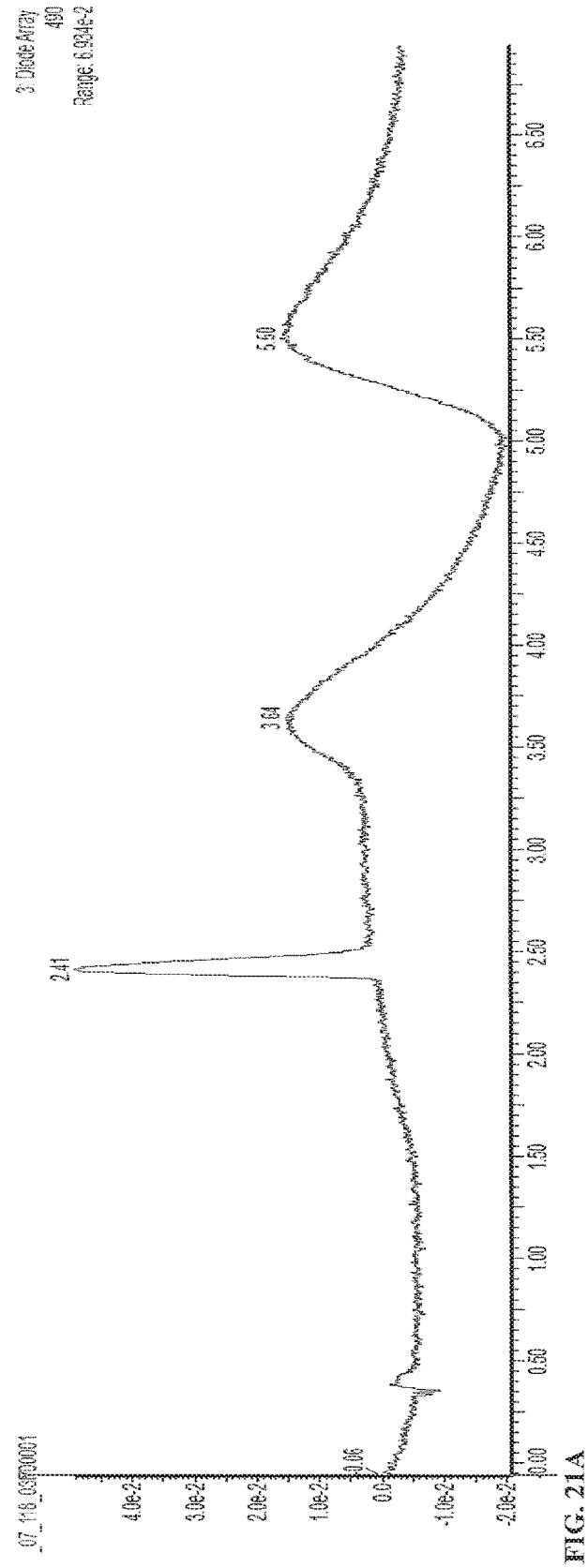
FIG. 21A shows the LC/MS Chromatogram profiles of compound 1: OTL78 at 490 nm UV wavelength after HPLC purification.
Figure 21B:
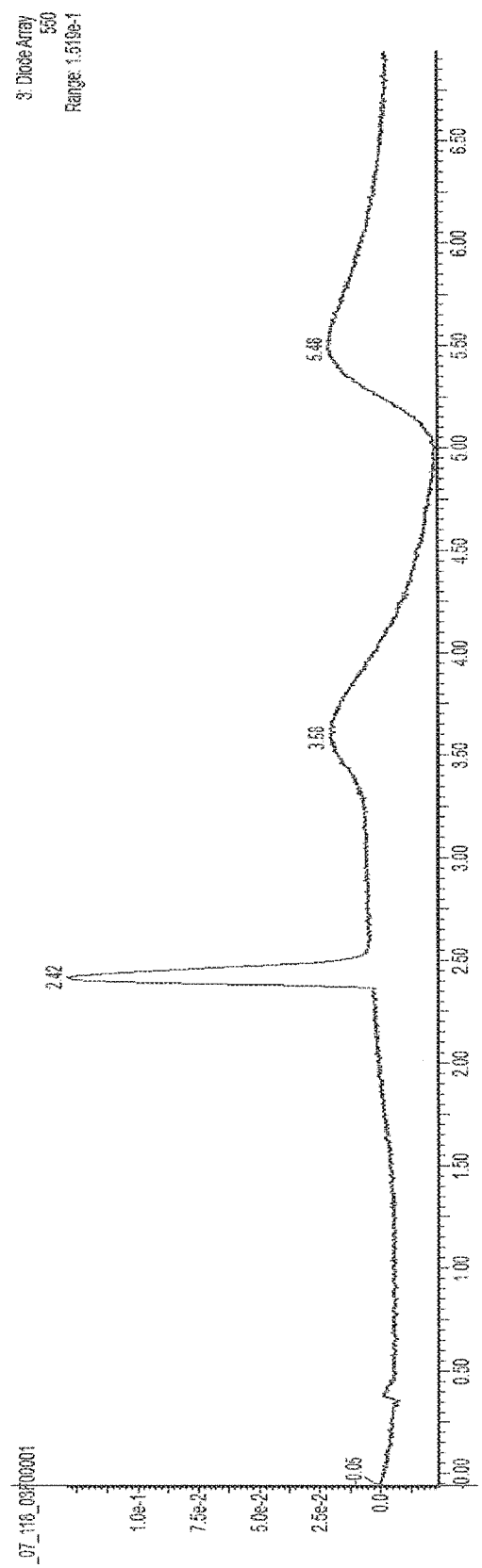
FIG. 21B depicts the LC/MS Chromatogram profiles of compound 1: OTL78 at 550 nm UV wavelength after HPLC purification.
Figure 21C:
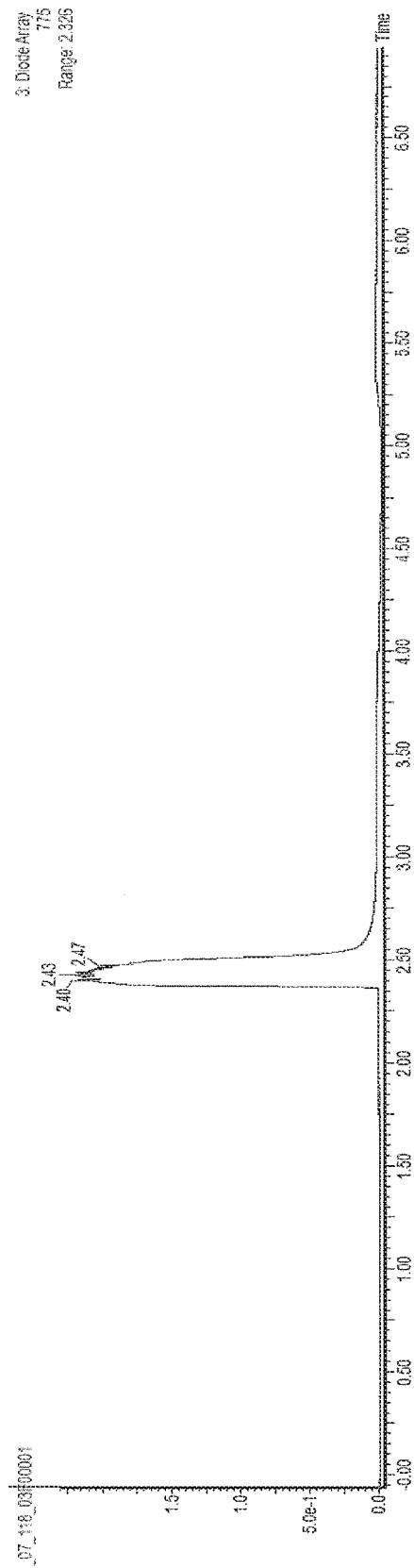
FIG. 21C illustrates the LC/MS Chromatogram profiles of compound 1: OTL78 at 775 nm UV wavelength after HPLC purification.
Figure 22A:
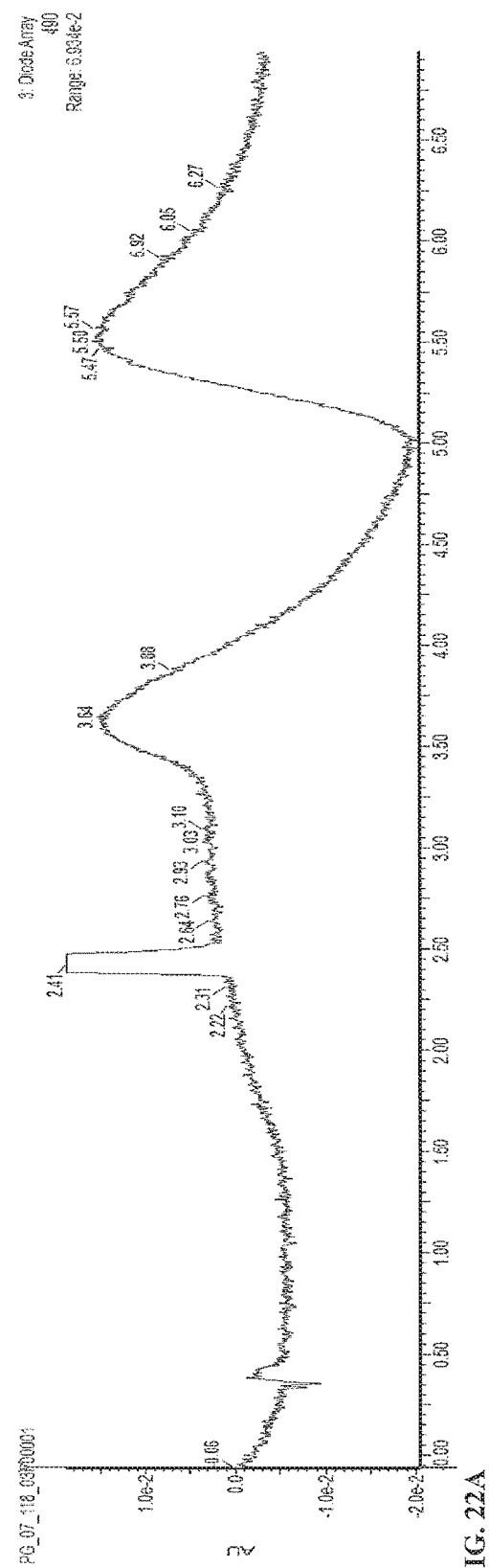
FIG. 22A shows the magnified view of FIG. 21A for impurity analysis.
Figure 22B:
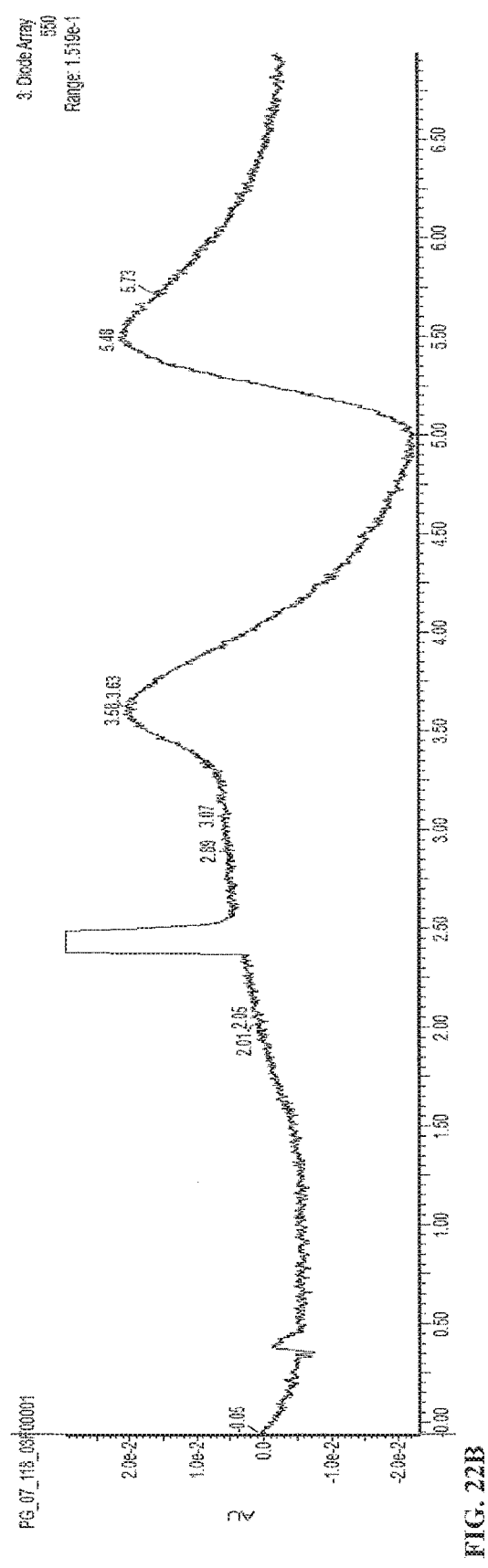
FIG. 22B depicts the magnified view of FIG. 21B for impurity analysis.
Figure 22C:
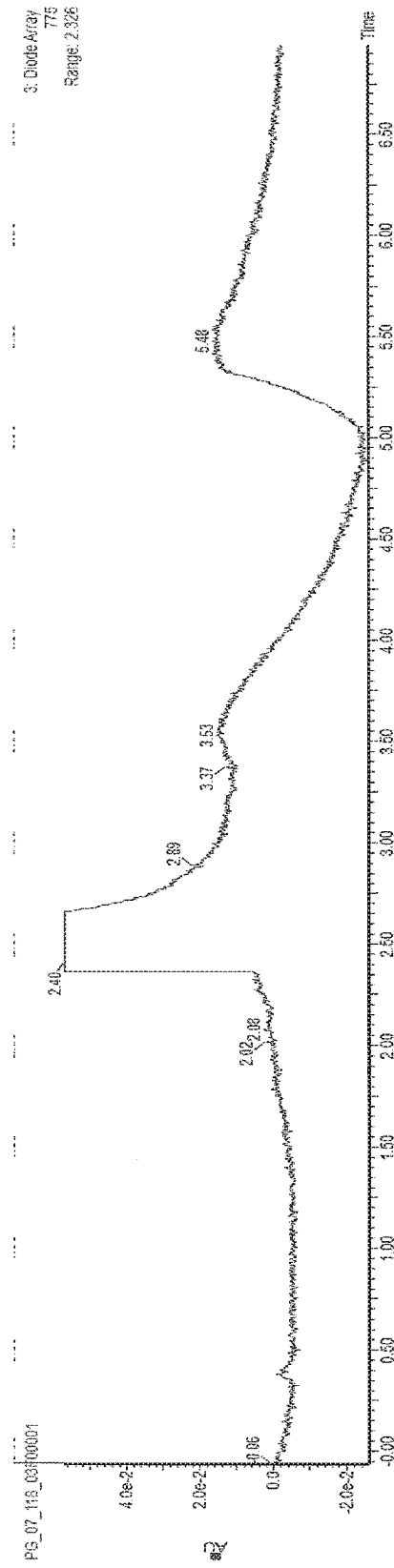
FIG. 22C illustrates the magnified view of FIG. 21C for impurity analysis.
Figure 23A:
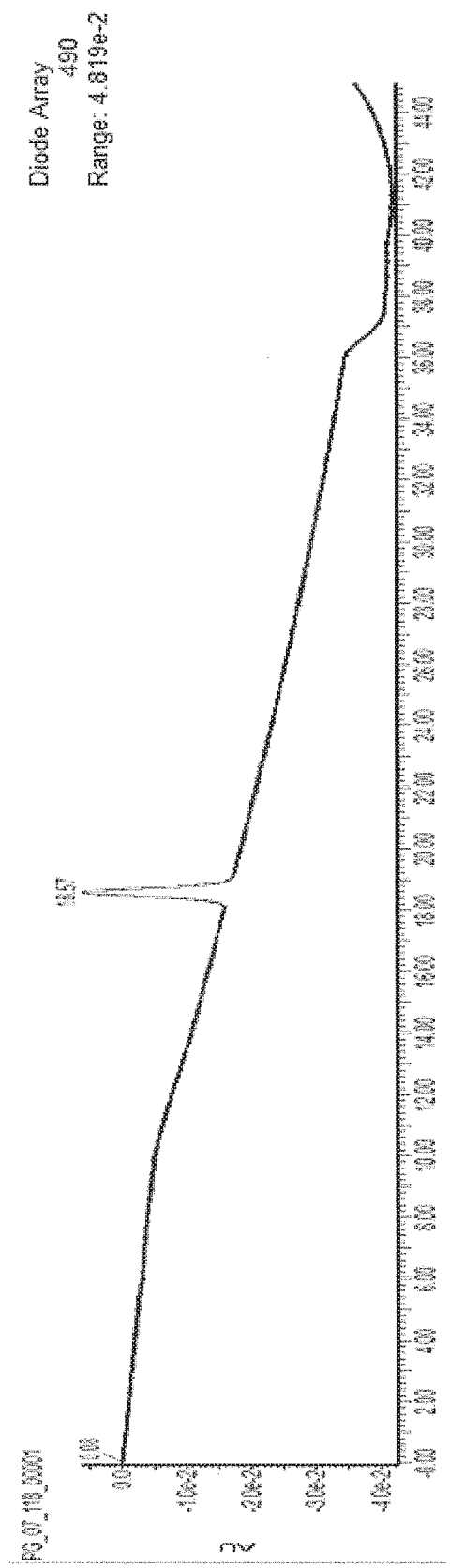
FIG. 23A shows the UPLC with HPLC column Chromatogram profiles of compound 1: OTL78 at 490 nm UV wavelength after HPLC purification.
Figure 23B:
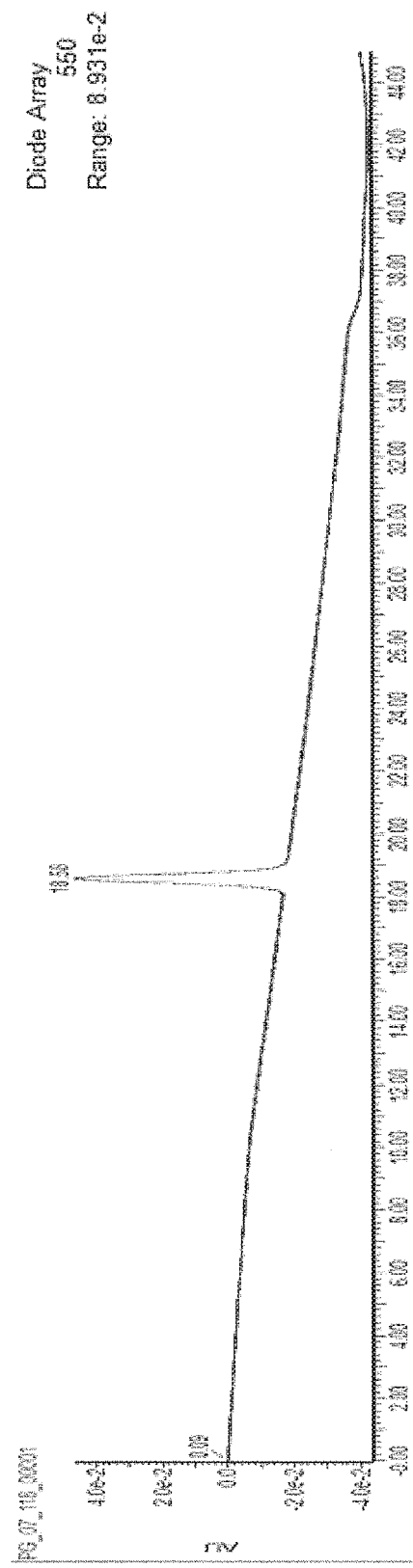
FIG. 23B depicts the UPLC with HPLC column Chromatogram profiles of compound 1: OTL78 at 550 nm UV wavelength after HPLC purification.
Figure 23C:
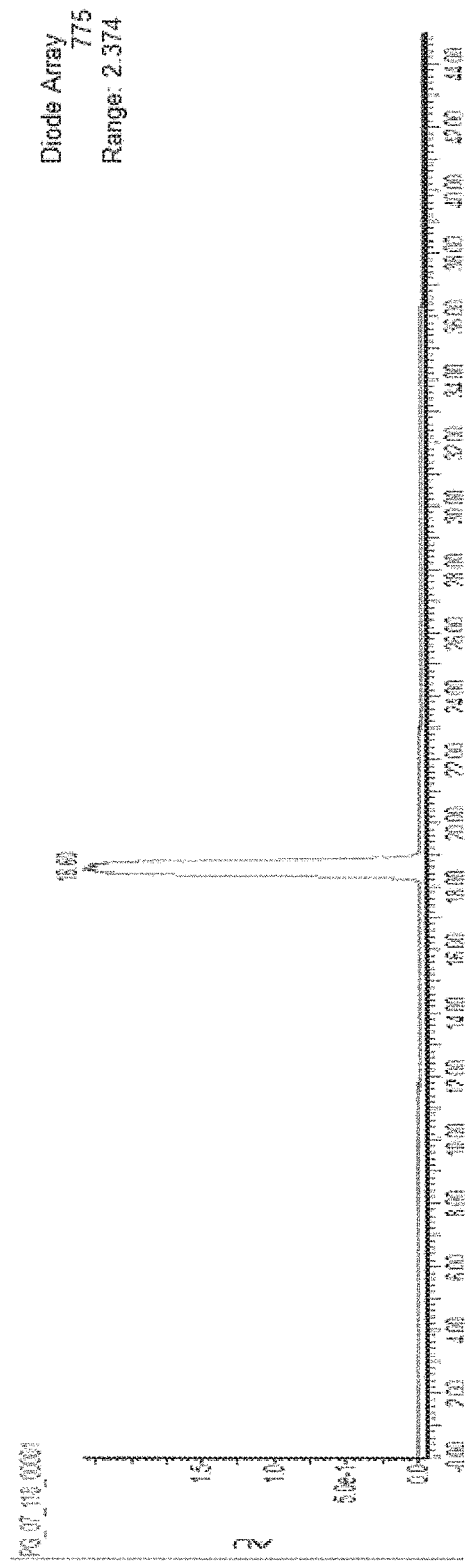
FIG. 23C illustrates the UPLC with HPLC column Chromatogram profiles of compound 1: OTL78 at 775 nm UV wavelength after HPLC purification.
Figure 24A:
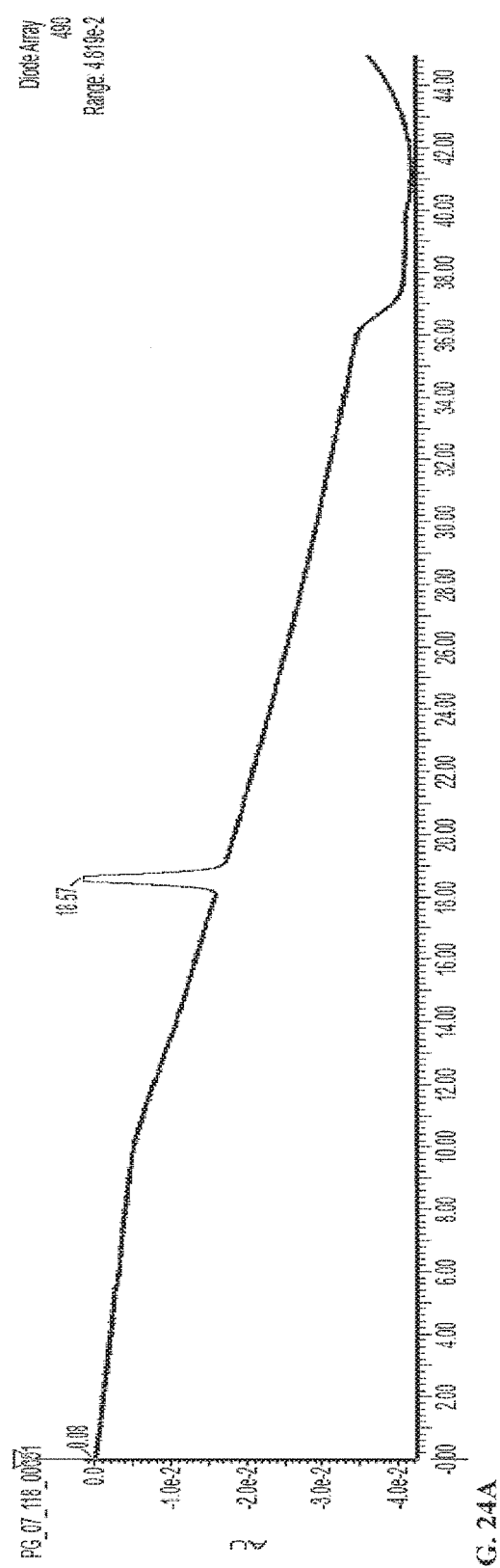
FIG. 24A shows the magnified view of FIG. 23A.
Figure 24B:
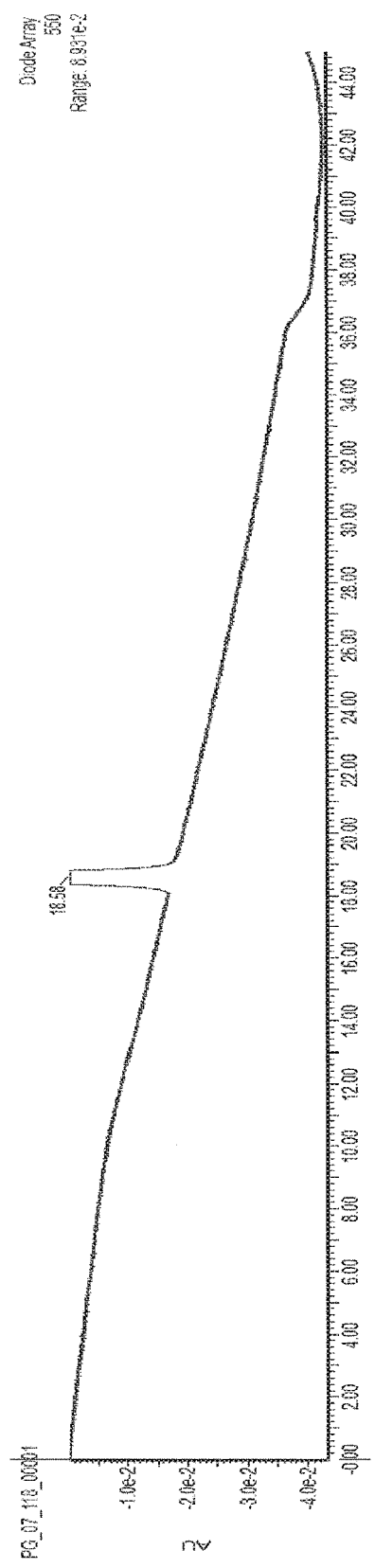
FIG. 24B depicts the magnified view of FIG. 23B.
Figure 24C:
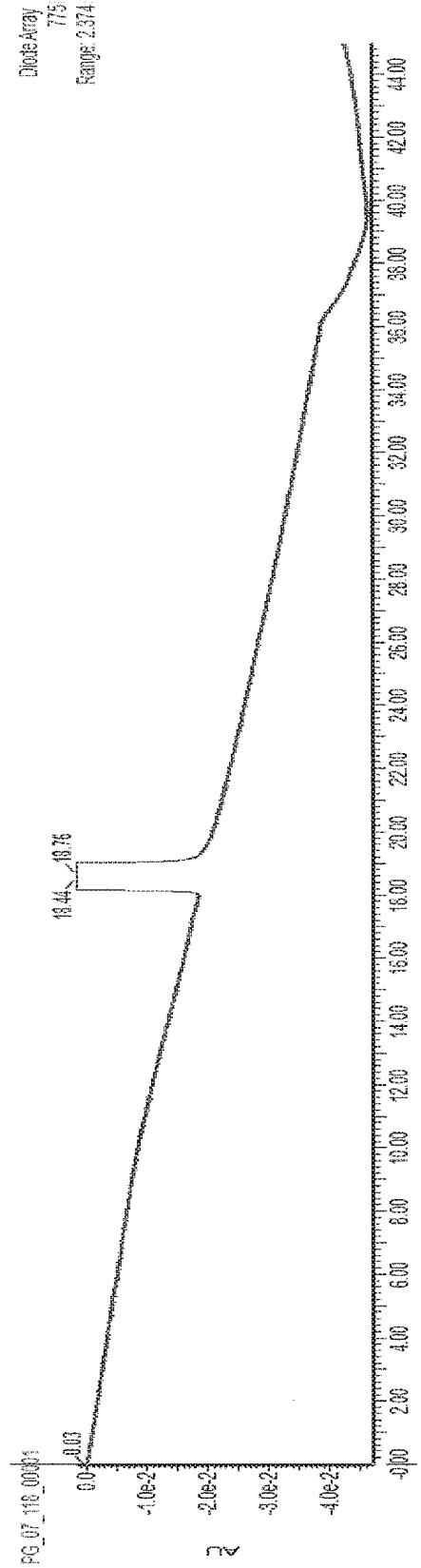
FIG. 24C illustrates the magnified view of FIG. 23C.

FIGS. 19A-D illustrate compound 1 detection at 220 nm (FIG. 19A), 490 nm (FIG. 19B), 550 nm (FIG. 19C), and 775 nm (FIG. 19D) wavelengths after Step VII LC/MS Method silica column purification and lyophilization. FIGS. 20A-D illustrate compound 1 detection at 490 nm (FIG. 20A), 550 nm (FIG. 20B), 775 nm (FIG. 20C), and 265 nm (FIG. 20D) wavelengths after UPLC/MS Method silica column purification and lyophilization. FIGS. 21A-C illustrate compound 1 detection at 490 nm (FIG. 21A), 550 nm (FIG. 21B), and 775 nm (FIG. 21C) wavelengths after HPLC purification. FIGS. 22A-C are magnified views of FIGS. 21A-C, respectively. FIGS. 23A-D illustrate compound 1 detection at 490 nm (FIG. 23A), 550 nm (FIG. 23B), 775 nm (FIG. 23C) and 265 nm (FIG. 20D) wavelengths after UPLC with HPLC column after HPLC purification. FIGS. 24A-C are magnified views of FIGS. 23A-C, respectively.

Step VIII

Synthesis of (S)-5-benzyl-1-tert-butyl 2-(3-((S)-1,5-di-tert-butoxy-1,5-dioxopentan-2-yl)ureido)pentanedioate (15)

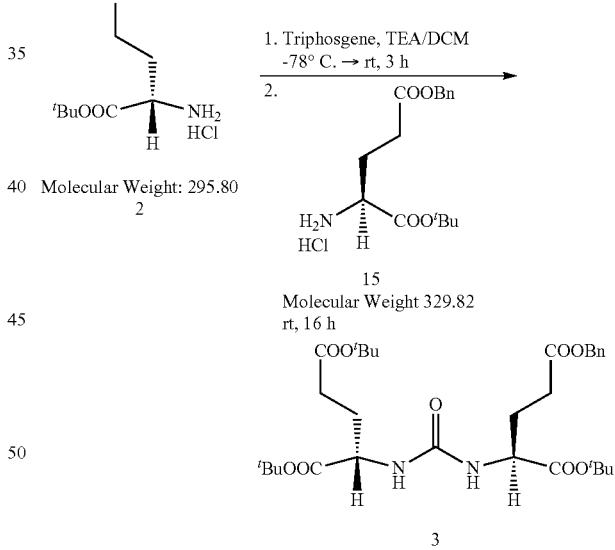

A 500 mL round bottom flask was charged with compound 2, glutamic acid with tert-butyl protection groups on each hydroxyl group of each carboxylic acid group (6.0 g, 20.28 mmol, 1 equiv) and triphosgene (1.805 g, 6.69 mmol, 0.333 equiv) under an argon atmosphere. Approximatley 210 mL of dichloromethane was added under inert atmosphere to give a clear solution and cooled to −78° C. in dry ice/acetone bath (Suspension VIII-A). Triethylamine (9.9 mL, 8.19 mmol, 3.5 equiv) was added drop wise to the reaction mixture (Suspension VIII-A) in 10 minutes to form a thick white suspension. Reaction mixture was allowed to warm to room temperature and stirred for 3 hours at room temperature (Suspension VIII-A). Another 100 mL round bottom flask was charged with compound 15, glutamic acid with a tert-butyl protection group on the hydroxyl group of the alpha carboxylic acid group and a benzyl group on the hydroxyl of the side chain carboxylic acid (6.69 g, 20.28 mmol, 1.0 equiv) and dissolved in 40 mL of DCM (Solution VIII-B). Triethylamine (5.65 mL, 40.56 mmol, 2.0 equiv) was added to the suspension VIII-B in 2 minutes followed by drop wise addition of suspension VIII-B to suspension VIII-A via cannula over the period of 30 minutes to give a white suspension. The reaction was stirred at 23° C. for 12 hours. 400 mL of 1 M aqueous HCl was added to the reaction and stirred for additional 1 hour. The reaction mixture was extracted using EtOAc three 200 mL extractions.

The combined organic extracts were washed with 100 mL of water two times followed by 100 mL of brine, dried over anhydrous $Na_2SO_4$, filtered, and concentrated under vacuum to obtain compound 3 as clear thick oil (14.10 g), which was subjected to the next step without further purification.

Synthesis of (S)-5-(tert-butoxy)-4-(3-((S)-1,5-di-tert-butoxy-1,5-dioxopentan-2-yl)ureido)-5-oxopentanoic acid (compound 4, DUPA)

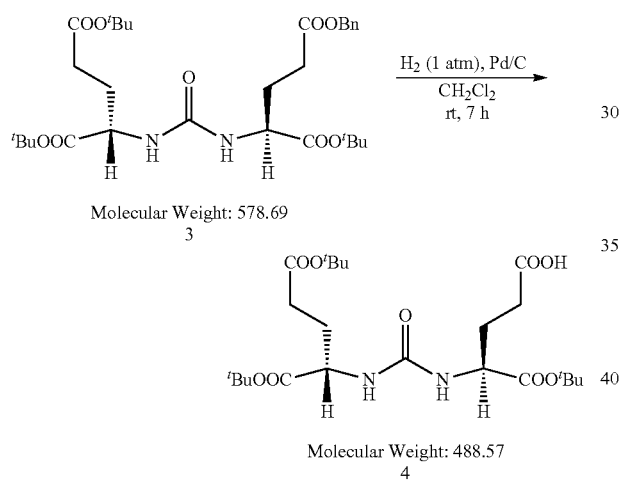

In a 500 mL round bottom flask, 14.1 grams of compound 3 was dissolved in 200 mL of DCM. 6 grams of 10% Pd/C was added under argon atmosphere. The reaction mixture was stirred under atmospheric hydrogen pressure for 7 hours. Reaction was monitored by TLC. Upon completion of the reaction, Pd/C was removed by filtration through a Celite pad and which was then washed with DCM and the filtrate was concentrated. The crude product was purified using flash chromatography (hexane:EtOAc, 40:60) to yield compound 4 as a colorless oil. Crystallized using hexane:DCM gave a white solid (8.01 g, 80% yield over two steps).

What is claimed is:

1. A method for synthesizing a compound of the formula:

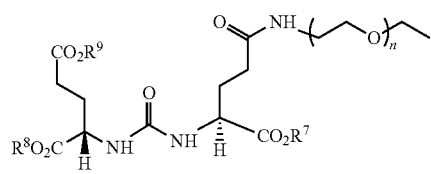

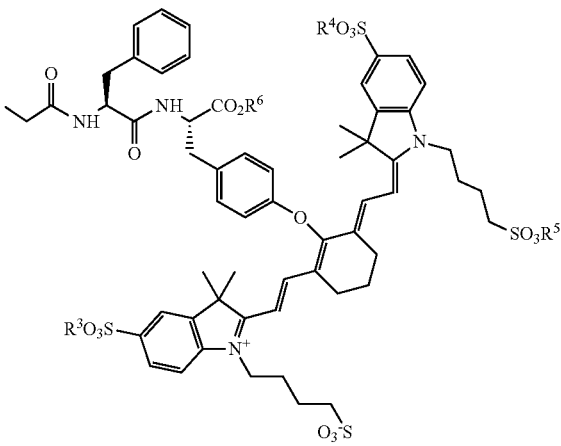

wherein n is 0, 1, 2, 3, or 4;

further wherein $R^3$, $R^4$, and $R^5$ are independently selected from the group consisting of $H^+$, $Na^+$, $K^+$, and $NH_4^+$; $R^6$, $R^7$, $R^8$, and $R^9$ are independently selected from the group consisting of $H^+$, $Na^+$, $K^+$, and $NH_4^+$; and $R^{10}H^+$;

comprising the steps of:

(a) reacting a compound of formula I:

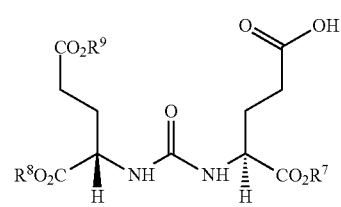

with a compound of formula:

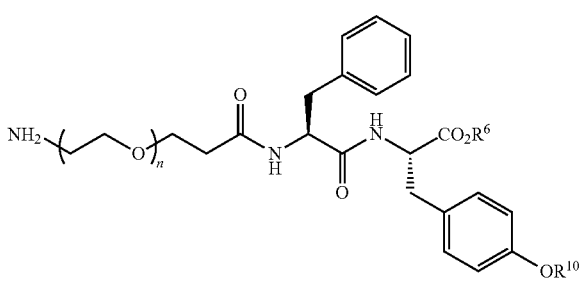

in the presence of a polar organic solvent, 1-[Bis(dimethylamino)methylene]-1H-1,2,3-triazolo[4,5-b]pyridinium 3-oxid hexafluorophosphate and N,N-Diisopropylethylamine under argon and (b) reacting the resulting compound with sodium carbonate and a dye compound of the formula

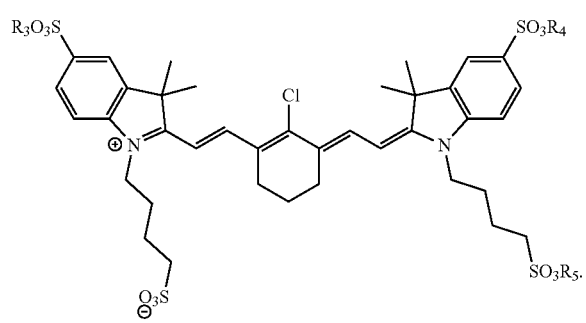

2. The method of claim 1, wherein the polar organic solvent is selected from the group consisting of dimethyl sulfoxide, dimethylformamide, and water.

3. A method for synthesizing an isotopic form of a compound of the formula:

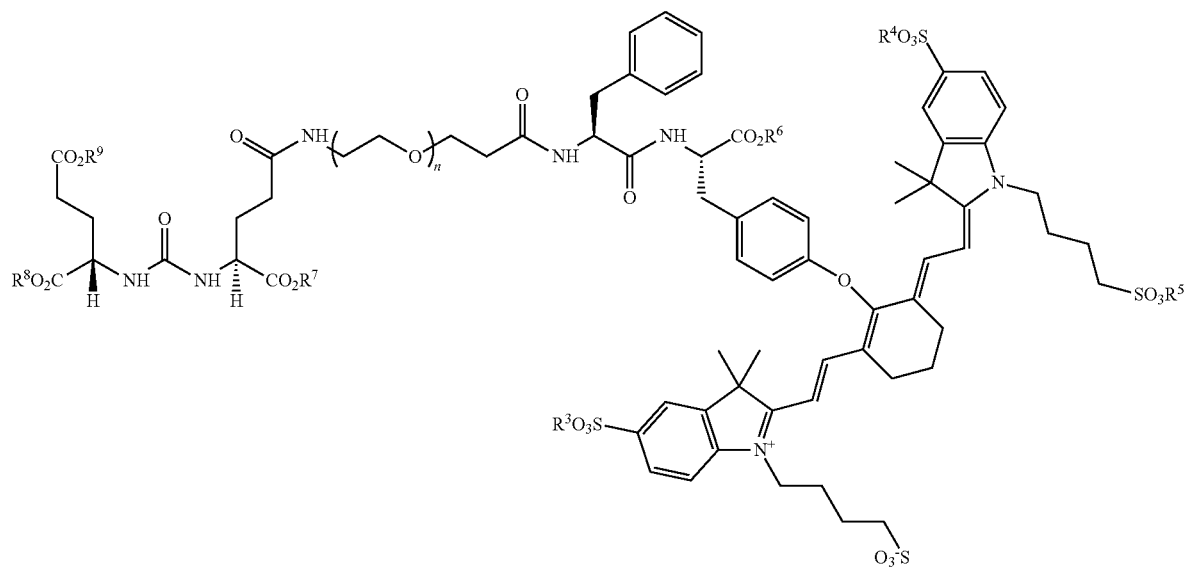

wherein said isotopic form comprises one or more carbon and/or hydrogen isotopes selected from the group consisting of $H^2$, $H^3$, $C^{13}$ and $C^{14}$;

further wherein n is 0, 1, 2, 3, or 4;

further wherein $R^3$, $R^4$, and $R^5$ are independently selected from the group consisting of $H^+$, $Na^+$, $K^+$, and $NH_4^+$; $R^6$, $R^7$, $R^8$, and $R^9$ are independently selected from the group consisting of $H^+$, $Na^+$, $K^+$, and $NH_4^+$; and $R^{10}H^+$;

comprising the steps of:

(a) reacting an isotopic form of a compound of formula:

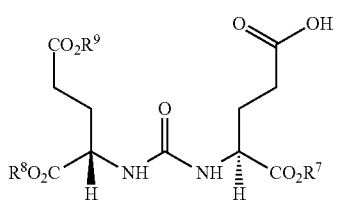

wherein said isotopic form comprises one or more carbon and/or hydrogen isotopes selected from the group consisting of $H^2$, $H^3$, $C^{13}$ and $C^{14}$, with an isotopic form of a compound of formula:

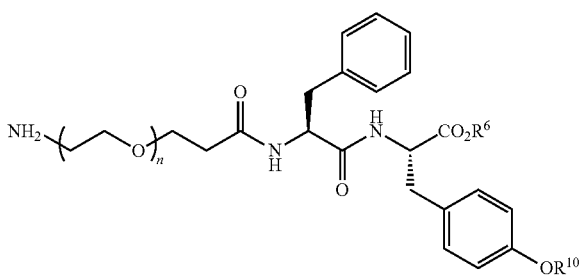

wherein said isotopic form comprises one or more carbon and/or hydrogen isotopes selected from the group consisting of $H^2$, $H^3$, $C^{13}$ and $C^{14}$, in the presence of a polar organic solvent, 1-[Bis(dimethylamino)methylene]-1H-1,2,3-triazolo[4,5-b]pyridinium 3-oxid hexafluorophosphate and N,N-Diisopropylethylamine under argon to provide an isotopic form of a compound that comprises one or more carbon and/or hydrogen isotopes selected from the group consisting of $H^2$, $H^3$, $C^{13}$ and $C^{14}$, (b) reacting the isotopic form of the compound obtained in step (a) with sodium carbonate and an isotopic form of a dye compound of the formula:

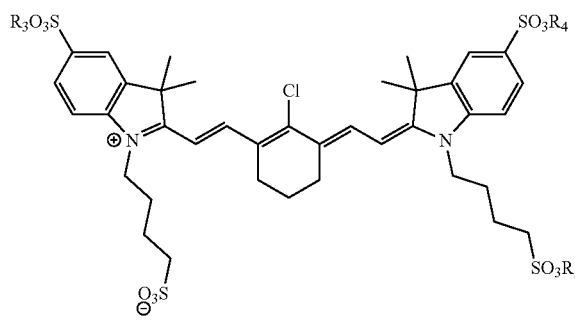

wherein said isotopic form comprises one or more carbon and/or hydrogen isotopes selected from the group consisting of $H^2$, $H^3$, $C^{13}$ and $C^{14}$.

4. A method for synthesizing a compound of the formula:

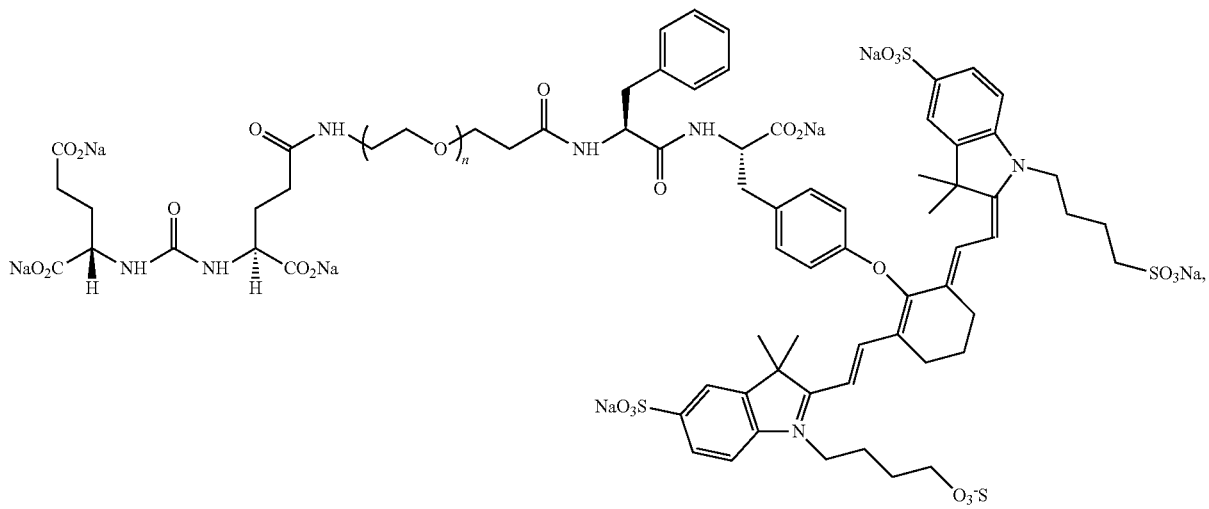

wherein n is 0, 1, 2, 3, or 4

(a) reacting a compound of formula

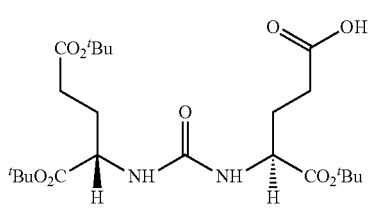 [SMILES: CC(C)(C)OC(=O)CC[C@H](NC(=O)N[C@@H](CCC(=O)O)C(=O)OC(C)(C)C)C(=O)OC(C)(C)C]

with a compound of formula:

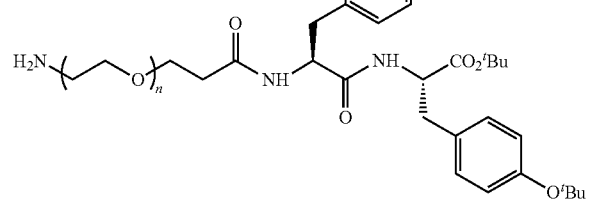

in the presence of a polar organic solvent, 1-[Bis(dimethylamino)methylene]-1H-1,2,3-triazolo[4,5-b]pyridinium 3-oxid hexafluorophosphate and N,N-Diisopropylethylamine under argon (b) reacting the resulting compound thereof with sodium carbonate and a dye compound of the formula:

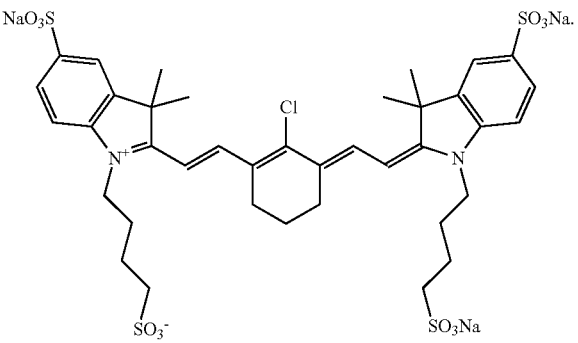

* * * * *